US012780776B2

(12) United States Patent
Pinto et al.

(10) Patent No.: US 12,780,776 B2
(45) Date of Patent: Nov. 3, 2026

(54) NAPHTHALENE AND QUINOLINE ANALOGS AS RXFP1 AGONISTS

(71) Applicant: BRISTOL-MYERS SQUIBB COMPANY, Princeton, NJ (US)

(72) Inventors: Donald J. P. Pinto, Churchville, PA (US); Michael J. Orwat, New Hope, PA (US); Leon M. Smith, II, Somerset, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 312 days.

(21) Appl. No.: 18/718,470

(22) PCT Filed: Dec. 14, 2022

(86) PCT No.: PCT/US2022/081514
§ 371 (c)(1),
(2) Date: Jun. 11, 2024

(87) PCT Pub. No.: WO2023/114818
PCT Pub. Date: Jun. 22, 2023

(65) Prior Publication Data
US 2025/0100960 A1 Mar. 27, 2025

Related U.S. Application Data

(60) Provisional application No. 63/289,822, filed on Dec. 15, 2021.

(51) Int. Cl.

| | |
|---|---|
| ***C07C 235/56*** | (2006.01) |
| ***A61K 31/167*** | (2006.01) |
| ***A61K 31/27*** | (2006.01) |
| ***A61K 31/351*** | (2006.01) |
| ***A61K 31/423*** | (2006.01) |
| ***A61K 31/425*** | (2006.01) |
| ***A61K 31/50*** | (2006.01) |
| ***C07C 271/24*** | (2006.01) |
| ***C07C 317/22*** | (2006.01) |
| ***C07D 237/14*** | (2006.01) |
| ***C07D 261/20*** | (2006.01) |
| ***C07D 275/02*** | (2006.01) |
| ***C07D 309/08*** | (2006.01) |

(52) U.S. Cl.
CPC .......... *C07C 235/56* (2013.01); *A61K 31/167* (2013.01); *A61K 31/27* (2013.01); *A61K 31/351* (2013.01); *A61K 31/423* (2013.01); *A61K 31/425* (2013.01); *A61K 31/50* (2013.01); *C07C 271/24* (2013.01); *C07C 317/22* (2013.01); *C07D 237/14* (2013.01); *C07D 261/20* (2013.01); *C07D 275/02* (2013.01); *C07D 309/08* (2013.01)

(58) Field of Classification Search
CPC combination set(s) only.
See application file for complete search history.

(56) References Cited

FOREIGN PATENT DOCUMENTS

| | | |
|---|---|---|
| EP | 1614576 | 1/2006 |
| WO | 2013165606 A1 | 11/2013 |
| WO | 2023/076626 A1 | 5/2023 |
| WO | 2023077040 A1 | 5/2023 |
| WO | 2023077041 A1 | 5/2023 |
| WO | 2023077070 A1 | 5/2023 |
| WO | 2023/114819 A1 | 6/2023 |
| WO | 2023/114822 A1 | 6/2023 |
| WO | 2023/114823 A1 | 6/2023 |
| WO | 2023/114824 A1 | 6/2023 |

OTHER PUBLICATIONS

Garber_2001, "Relaxin decreases renal interstitial fibrosis and slows progression of renal disease", Kidney International, vol. 59 (2001), pp. 876-882.
Ludwig_2004, "Convenient Synthesis of Pyrrole- and Indolecarboxylic Acid tert-Butylesters", Synthetic Communications, 34:20, 3691-3695.
Mohammed et al., "Coronary Microvascular Rarefaction and Myocardial Fibrosis in Heart Failure With Preserved Ejection Fraction", Circulation, vol. 131, pp. 550-559 (2015).

(Continued)

*Primary Examiner* — Umamaheswari Ramachandran
(74) *Attorney, Agent, or Firm* — Hong Liu

(57) ABSTRACT

The disclosure relates to compounds of Formula (I), which are RXFP1 receptor agonists, compositions containing them, and methods of using them, for example, in the treatment of heart failure, fibrotic diseases, and related diseases such as lung disease (e.g., idiopathic pulmonary fibrosis), kidney disease (e.g., chronic kidney disease), or hepatic disease (e.g., non-alcoholic steatohepatitis and portal hypertension).

(I)

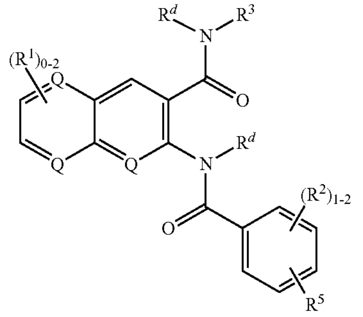

14 Claims, No Drawings

(56) References Cited

OTHER PUBLICATIONS

Roger et al., "Heart Disease and Stroke Statistics—2012 Update", Circulation, vol. 125, e2-220 (2012).
Teerlink_2013, "Serelaxin, recombinant human relaxin-2, for treatment of acute heart failure (RELAX-AHF): a randomised, placebo-controlled trial", The Lancet, vol. 381, Issue 9860 p. 29-39 Jan. 5, 2013.
Agoulnik,A.I., Synthetic non-peptide low molecular weight agonists of the relaxin receptor 1, British Journal of Pharmacology, 2017 174 pp. 977-989.
Allen, Jr., Loyd V., "Remington: The Science and Practice of Pharmacy, vol. I and vol. II. Twenty-second edition", Pharmaceutical Press, 2012, p. 2724.
Bennett_2014 "Relaxin decreases the severity of established hepatic fibrosis in mice", Liver International 34: 416-426.
Borlaug, et al. "Heart failure with preserved ejection fraction: pathophysiology, diagnosis, and treatment", European Heart Journal (2011) 32, 670-679.
Borlaug_2011 "Diastolic and Systolic Heart Failure Are Distinct Phenotypes Within the Heart Failure Spectrum", vol. 123, Issue 18, May 10, 2011; pp. 2006-2014.
Clapp et al., "Cardiovascular Function Before, During, and After the First and Subsequent Pregnancies", Am J Cardiol, vol. 80, pp. 1469-1473 (1997).
Conrad et al., "Maternal vasodilation in pregnancy: the emerging role of relaxin", Regul. Integr. Comp. Physiol., vol. 301, pp. R267-R275 (2011).
Dahlke et al "Safety and Tolerability of Serelaxin, a Recombinant Human Relaxin-2 in Development for the Treatment of Acute Heart Failure, inHealthy Japanese Volunteers and a Comparison of Pharmacokinetics and Pharmacodynamics in Healthy Japanese and Caucasian Populations", The Journal of Clinical Pharmacology , 55(4) 415-422, 2015.
Damman et al., "The Cardiorenal Syndrome in Heart Failure", Progress in Cardiovascular Diseases, vol. 54, pp. 144-154 (2011).
De Keulenaer_2011_"Systolic and Diastolic Heart Failure Are Overlapping Phenotypes Within the Heart Failure Spectrum"; vol. 123, Issue 18, May 10, 2011; pp. 1996-2005.
Greene, T.W. et al., Protecting Groups in Organic Synthesis, 4th Edition, Wiley (2007)).
Halls et al., "Relaxin Family Peptide Receptors—former orphans reunite with their parent ligands to activate multiple signalling pathways", British J of Pharmacology, vol. 150, pp. 677-691 (2007).
Halls ML., et al. "Relaxin Activates Multiple CAMP Signaling Pathway Profiles in Different Target Cells", Ann. N Y Acad. Sci., vol. 1160, 108-111 (2009).
Halls, et al., "Relaxin Family Peptide Receptors RXFP1 and RXFP2 Modulate CAMP Signaling by Distinct Mechanisms", vol. 70, pp. 214-226 (2006).
Halls_2009, "RXFP1 Couples to the Gαi3-Gβγ-PI3K-PKCζ Pathway via the Final 10 Amino Acids of the Receptor C-terminal Tail", Annals of the New York Academy of Sciences, 1160, 117-120.
Heidenreich et al., "Forecasting the Future of Cardiovascular Disease in the United States", Circulation, vol. 123, pp. 933-944 (2011).
Hisaw_1926 , "Experimental relaxation of the pubic ligament of the guinea pig", Proc Soc Exp Biol Med 23:661-663.
Hsu et al., "Activation of Orphan Receptors by the Hormone Relaxin", Science, vol. 295, pp. 671-674 (2002).
IUPAC 1996, Basic Terminology of Stereochemistry, Pure & Appl. Chem., vol. 68, No. 12, pp. 2193-2222, 1996.
Jessup et al., "Medical Progress. Heart Failure", The New England Journal of Medicine, vol. 348, pp. 3007-3018 (2003).
Jeyabalan_2010, "Renal Physiology and Pathophysiology in Pregnancy", Renal and Electrolyte Disorders, 2010, pp. 462-518.
Kemp et al., "The pathophysiology of heart failure", Cardiovascular Pathology, vol. 21, pp. 365-371 (2012).
Lewis, R.J., ed., Hawley's Condensed Chemical Dictionary, 13th Edition, John Wiley & Sons, Inc., New York 1997.
Matsushita, et al.,"The Association of Hemoglobin A1c With Incident Heart Failure Among People Without Diabetes: The Atherosclerosis Risk in Communities Study", Diabetes, vol. 59, pp. 2020-2026 (2010).
Millane et al ., "ABC of heart failure. Acute and chronic management strategies", BMJ, vol. 320 pp. 559-562 (2000).
Physicians' Desk Reference.
Ponikowski_2014, "A randomized, double-blind, placebo-controlled, multicentre study to assess haemodynamic effects of serelaxin in patients with acute heart failure", European Heart Journal (2014) 35, 431-441.
Poppas et al., "Serial Assessment of the Cardiovascular System in Normal Pregnancy" Circulation, vol. 95(10) pp. 2407-2415 (1997).
Roger V. et al., "Trends in Heart Failure Incidence and Survival in a Community-Based Population", JAMA, vol. 292, pp. 344-350 (2004).
Roger, V.L., "Epidemiology of Heart Failure", Circulation Research, vol. 113(6), pp. 646-659 (2013).
Sherwood et al., "Relaxin's Physiological Roles and Other Diverse Actions", Endocr. Rev. vol. 25, pp. 205-234 2004.
Smith_2006 "Influence of Recombinant Human Relaxin on Renal Hemodynamics in Healthy Volunteers", J Am Soc Nephrol 17: 3192-3197, 2006.
Teichman et al., "Relaxin, a pleiotropic vasodilator for the treatment of heart failure", Heart Fail. Rev., vol. 14, pp. 321-329 (2009).
Torikai K, Design and synthesis of benzoacridines as estrogenic and anti estrogenic agents, vol. 25, Iss 20, 2017 pp. 5216-5237 Abstract only.
Unemori_1996, "Relaxin Induces an Extracellular Matrix-degrading Phenotype in Human Lung Fibroblasts In Vitro and Inhibits Lung Fibrosis in a Murine Model In Vivo", J. Clin. Invest, vol. 98, No. 12, Dec. 1996, 2739-2745.
Voors_2014, "Renal Hemodynamic Effects of Serelaxin in Patients With Chronic Heart Failure", vol. 7, Issue 6, Nov. 2014; pp. 994-1002.
Wilson_2018, Optimization of the first small molecule relaxin/insulin like family peptide receptor (RXFP1) agonists: Activation results in an antifibrotic gene expression profile, European Journal of Medicinal Chemistry, 156 pp. 79-92.
Wohlfahrt et al., "Impact of chronic changes in arterial compliance and resistance on left ventricular ageing in humans", Eur. J. Heart Fail., vol. 17, pp. 27-34 (2015).

NAPHTHALENE AND QUINOLINE ANALOGS AS RXFP1 AGONISTS

CROSS-REFERENCE TO RELATED APPLICATIONS

This application is a 371 application of PCT/US2022/081514, filed Dec. 14, 2022, which claims the benefit of U.S. Provisional Application No. 63/289,822, filed Dec. 15, 2021, the disclosure of which is incorporated herein by reference in its entirety.

BACKGROUND OF THE INVENTION

The present disclosure relates to novel compounds which are relaxin family peptide receptor 1 (RXFP1) agonists, compositions containing them, and methods of using them, for example in the treatment of heart failure, fibrotic diseases, and related diseases such as lung disease (e.g., idiopathic pulmonary fibrosis), kidney disease (e.g., chronic kidney disease), and hepatic disease (e.g., non-alcoholic steatohepatitis and portal hypertension).

The human relaxin hormone (also called relaxin or H2 relaxin) is a 6-kDa peptide composed of 53 amino acids whose activity was initially discovered when Frederick Hisaw in 1926 injected crude extracts from swine corpus luteum into virgin guinea pigs and observed a relaxation of the fibrocartilaginous pubic symphysis joint (Hisaw F L., *Proc. Soc. Exp. Biol. Med.,* 1926, 23, 661-663). The relaxin receptor was previously known as Lgr7 but is now officially termed the relaxin family peptide receptor 1 (RXFP1) and was deorphanized as a receptor for relaxin in 2002 (Hsu S Y., et al., *Science,* 2002, 295, 671-674). RXFP1 is reasonably well conserved between mouse and human with 85% amino acid identity and is essentially ubiquitously expressed in humans and in other species (Halls M L., et al., *Br. J. Pharmacol.,* 2007, 150, 677-691). The cell signaling pathways for relaxin and RXFP1 are cell type dependent and quite complex (Halls M L., et al., *Br. J. Pharmacol.,* 2007, 150, 677-691; Halls M L., et al. *Ann. N Y Acad. Sci.,* 2009, 1160, 108-111; Halls M L., *Ann N Y Acad Sci.,* 2007, 1160, 117-120). The best studied pathway is the relaxin-dependent increase in cellular levels of cAMP in which relaxin functions as an RXFP1 agonist to promote GαS coupling and activation of adenylate cyclase (Halls M L., et al., *Mol. Pharmacol.,* 2006, 70, 214-226).

Since the initial discovery of relaxin much experimental work has focused on delineating the role relaxin has played in female reproductive biology and the physiological changes that occur during mammalian pregnancy (Sherwood O D., *Endocr. Rev.,* 2004, 25, 205-234). During human gestation, in order to meet the nutritional demands imposed upon it by the fetus, the female body undergoes a significant ~30% decrease in systemic vascular resistance (SVR) and a concomitant ~50% increase in cardiac output (Jeyabalan A C., K. P., *Reanl and Electolyte Disorders.* 2010, 462-518), (Clapp J F. & Capeless E., *Am. J. Cardio.,* 1997, 80, 1469-1473). Additional vascular adaptations include an ~30% increase in global arterial compliance that is important for maintaining efficient ventricular-arterial coupling, as well as an ~50% increase in both renal blood flow (RBF) and glomerular filtration rate (GFR), important for metabolic waste elimination (Jeyabalan A C., K. P., *Reanl and Electolyte Disorders.* 2010, 462-518), (Poppas A., et al., *Circ.,* 1997, 95, 2407-2415). Both pre-clinical studies in rodents as well as clinical studies performed in a variety of patient settings, provide evidence that relaxin is involved, at least to some extent, in mediating these adaptive physiological changes (Conrad K P., *Regrd. Integr. Comp. Physiol.,* 2011, 301, R267-275), (Teichman S L., et al., *Heart Fail. Rev.,* 2009, 14, 321-329). Importantly, many of these adaptive responses would likely be of benefit to HF patients in that excessive fibrosis, poor arterial compliance, and poor renal function are all characteristics common to heart failure patients (Mohammed S F., et al., *Circ.,* 2015, 131, 550-559), (Wohlfahrt P., et al., *Eur. J. Heart Fail.,* 2015, 17, 27-34), (Damman K., et al., *Prog. Cardiovasc. Dis.,* 2011, 54, 144-153).

Heart failure (HF), defined hemodynamically as "systemic perfusion inadequate to meet the body's metabolic demands as a result of impaired cardiac pump function", represents a tremendous burden on today's health care system with an estimated United States prevalence of 5.8 million and greater than 23 million worldwide (Roger V L., et al., *Circ. Res.,* 2013, 113, 646-659). It is estimated that by 2030, an additional 3 million people in the United States alone will have HF, a 25% increase from 2010. The estimated direct costs (2008 dollars) associated with HF for 2010 was $25 billion, projected to grow to $78 B by 2030 (Heidenreich P A., et al., *Circ.,* 2011, 123, 933-944). Astoundingly, in the United States, 1 in 9 deaths has HF mentioned on the death certificate (Roger V L., et al., Circ., 2012, 125, e2-220) and, while survival after HF diagnosis has improved over time (Matsushita K., et al., *Diabetes,* 2010, 59, 2020-2026), (Roger V L., et al., *JAMA,* 2004, 292, 344-350), the death rate remains high with ~50% of people with HF dying within 5 years of diagnosis (Roger V L., et al., *Circ.,* 2012, 125, e2-220), (Roger V L., et al., *JAMA,* 2004, 292, 344-350).

The symptoms of HF are the result of inadequate cardiac output and can be quite debilitating depending upon the advanced stage of the disease. Major symptoms and signs of HF include: 1) dyspnea (difficulty in breathing) resulting from pulmonary edema due to ineffective forward flow from the left ventricle and increased pressure in the pulmonary capillary bed; 2) lower extremity edema occurs when the right ventricle is unable to accommodate systemic venous return; and 3) fatigue due to the failing heart's inability to sustain sufficient cardiac output (CO) to meet the body's metabolic needs (Kemp C D., & Conte J V., *Cardiovasc. Pathol.,* 2011. 21, 365-371). Also, related to the severity of symptoms, HF patients are often described as "compensated" or "decompensated". In compensated heart failure, symptoms are stable, and many overt features of fluid retention and pulmonary edema are absent. Decompensated heart failure refers to a deterioration, which may present as an acute episode of pulmonary edema, a reduction in exercise tolerance, and increasing breathlessness upon exertion (Millane T., et al., *BMJ.* 2000, 320, 559-562).

In contrast to the simplistic definition of poor cardiac performance not being able to meet metabolic demands, the large number of contributory diseases, multitude of risk factors, and the many pathological changes that ultimately lead to heart failure make this disease exceedingly complex (Jessup M. & Brozena S., *N. Engl. J. Med.,* 2003, 348, 3007-2018). Injurious events thought to be involved in the pathophysiology of HF range from the very acute such as myocardial infarction to a more chronic insult such as life-long hypertension. Historically, HF was primarily described as "systolic HF" in which decreased left-ventricular (LV) contractile function limits the expulsion of blood and hence results in a reduced ejection fraction (EF is stroke volume/end diastolic volume), or "diastolic HF" in which active relaxation is decreased and passive stiffness is increased limiting LV filling during diastole, however overall EF is maintained (Borlaug B A. & Paulus W J., *Eur Heart J.,* 2011, 32, 670-679). More recently, as it became understood that diastolic and systolic LV dysfunction was not uniquely specific to these two groups, new terminology was employed: "heart failure with reduced ejection fraction" (HFrEF), and "heart failure with preserved ejection fraction" (HFpEF) (Borlaug B A. & Paulus W J., *Eur Heart J.* 2011. 32, 670-679). Although these two patient populations have very similar signs and symptoms, whether HFrEF and HFpEF represent two distinct forms of HF or two extremes of a single spectrum sharing a common pathogenesis is currently under debate within the cardiovascular community (Borlaug B A. & Redfield M M., *Circ.,* 2011. 123, 2006-2013), (De Keulenaer G W., & Brutsaert D L., *Circ.,* 2011. 123, 1996-2004).

Serelaxin, an intravenous (IV) formulation of the recombinant human relaxin peptide with a relatively short first-phase pharmacokinetic half-life of 0.09 hours, is currently being developed for the treatment of HF (Novartis, 2014). Serelaxin has been given to normal healthy volunteers (NHV) and demonstrated to increase RBF (Smith M C., et al., *J. Am. Soc. Nephrol.* 2006, 17, 3192-3197) and estimated GFR (Dahlke M., et al., *J. Clin. Pharmacol.,* 2015, 55, 415-422). Increases in RBF were also observed in stable compensated HF patients (Voors A A., et al., *Cir. Heart Fail.,* 2014. 7, 994-1002). In large clinical studies, favorable changes in worsening renal function, worsening HF, as well as fewer deaths, were observed in acute decompensated HF (ADHF) patients in response to an in-hospital 48 hour IV infusion of serelaxin (Teerlink J R., et al., *Lancet.* 2013, 381, 29-39), (Ponikowski P., et al., *Eur. Heart,* 2014. 35, 431-441). Suggesting that chronic dosing of serelaxin could provide sustained benefit to HF patients, improvement in renal function based on serum creatinine levels was observed in scleroderma patients given serelaxin continuously for 6 months using a subcutaneous pump (Teichman S L., et al., *Heart Fail. Rev.,* 2009, 14, 321-329). In addition to its potential as a therapeutic agent for the treatment of HF, continuous subcutaneous administration of relaxin has also been demonstrated to be efficacious in a variety of animal models of lung (Unemori E N., et al., *J. Clin. Invet.,* 1996, 98, 2739-2745), kidney (Garber S L., et al., *Kidney Int.,* 2001, 59, 876-882), and liver injury (Bennett R G., *Liver Int.,* 2014. 34, 416-426).

In summary, a large body of evidence supports a role for relaxin-dependent agonism of RXFP1 mediating the adaptive changes that occur during mammalian pregnancy, and that these changes translate into favorable physiological effects and outcomes when relaxin is given to HF patients. Additional preclinical animal studies in various disease models of lung, kidney, and liver injury provide evidence that relaxin, when chronically administered, has the potential to provide therapeutic benefit for multiple indications in addition to HF. More specifically, chronic relaxin administration could be of benefit to patients suffering from lung disease (e.g., idiopathic pulmonary fibrosis), kidney disease (e.g., chronic kidney disease), or hepatic disease (e.g., non-alcoholic steatohepatitis and portal hypertension).

SUMMARY OF THE INVENTION

The present invention provides novel substituted naphthalene and quinoline compounds, their analogues, including stereoisomers, tautomers, pharmaceutically acceptable salts, or solvates thereof, which are useful as RXFP1 receptor agonists.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used, for example, in the treatment and/or prophylaxis of heart failure, fibrotic diseases, and related diseases, such as; lung disease (e.g., idiopathic pulmonary fibrosis), kidney disease (e.g., chronic kidney disease), or hepatic disease (e.g., non-alcoholic steatohepatitis and portal hypertension).

The compounds of the present invention may be used in therapy.

The compounds of the present invention may be used for the manufacture of a medicament for the treatment and/or prophylaxis of heart failure.

The compounds of the invention can be used alone, in combination with other compounds of the present invention, or in combination with one or more, preferably one to two other agent(s).

These and other features of the invention will be set forth in expanded form as the disclosure continues.

DESCRIPTION OF THE INVENTION

The invention encompasses compounds of Formula (I), which are RXFP1 receptor agonists, compositions containing them, and methods of using them.

In a first aspect, the present invention provides, inter alia, compounds of Formula (I):

(I)

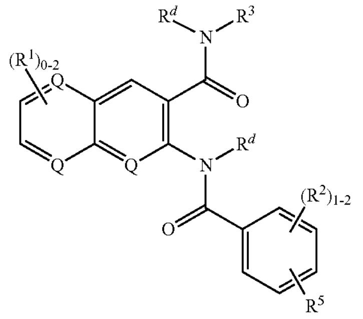

or pharmaceutically acceptable salts thereof, wherein:

Q, at each occurrence, is CH, $CR^1$, or N; provided that no more than one Q is N;

$R^1$ is halo or $C_{1-4}$ alkyl substituted with 0-5 halo;

$R^2$ is halo, CN, $—OC_{1-4}$ alkyl, or $C_{1-4}$ alkyl substituted with 0-5 halo or OH;

$R^3$ is $C_{1-4}$ alkyl substituted with 0-5 $R^4$, $—(CR^dR^d)_n—C_{3-10}$-carbocyclyl substituted with 0-5 $R^4$ or $—(CR^dR^d)_n$-3 to 6-membered heterocyclyl comprising 1-4 heteroatoms selected from O, $S(=O)_p$, N, and $NR^d$, and substituted with 0-5 $R^4$;

$R^4$ is halo, CN, $C_{1-4}$ alkyl substituted with 0-5 halo, OH, $—OC_{1-4}$ alkyl substituted with 0-5 halo, $—S(O)_pR^c$, aryl, or a 4- to 6-membered heterocyclyl comprising 1-4 heteroatoms selected from O, $S(=O)_p$, N, and $NR^d$;

$R^5$ is $—S(=O)_pR^c$, $—S(=O)_pNR^aR^a$, $C_{2-6}$ alkenyl substituted with 0-5 halo or OH, $C_{2-6}$ alkynyl substituted with 0-5 halo or OH, $C_{3-6}$ carbocyclyl substituted with 0-3 $R^6$ and 0-2 $R^7$, or a 3- to 12-membered heterocyclyl comprising 1-5 heteroatoms selected from O, $S(=O)_p$, N, and $NR^{10}$, and substituted with 0-3 $R^6$ and 0-2 $R^7$;

$R^6$ is halo, CN, =O, —OH, —$OC_{1-4}$ alkyl, or $C_{1-4}$ alkyl substituted with 0-2 halo or OH;

$R^7$ is $C_{1-4}$ alkyl substituted with 0-1 $R^8$ and 0-1 $R^9$, —$OR^b$, —$NR^aR^a$, —$NR^aC(=O)R^b$, —$NR^aC(=O)OR^b$, —$NR^aC(=O)NR^aR^a$, —$NR^aS(=O)_pR^c$, —$C(=O)R^b$, —$C(=O)OR^b$, —$C(=O)NR^aR^a$, —$C(=O)NR^aS(=O)_pR^c$, —$OC(=O)R^b$, —$S(=O)_pR^c$, —$S(=O)_pNR^aR^a$, $C_{3-6}$ cycloalkyl, or a 4- to 6-membered heterocyclyl comprising 1-4 heteroatoms selected from O, $S(=O)_p$, N and $NR^d$, and substituted with 0-5 $R^e$;

$R^8$ is halo, —$C(=O)OR^b$, —$C(=O)NR^aR^a$, —$C(=O)NR^aOR^b$, or $C_{1-4}$ alkyl substituted with 0-3 halo or OH;

$R^9$ is —$OR^b$, —$NR^aR^a$, —$NR^aC(=O)R^b$, —$NR^aC(=O)OR^b$, —$NR^aC(=O)NR^aR^a$, —$NR^aS(=O)_pR^c$, —$NR^aS(O)_pNR^aR^a$, —$OC(=O)NR^aR^a$, —$OC(=O)NR^aOR^b$, —$S(=O)NR^aR^a$, —$S(O)_pR^c$, —$(CH_2)_n$—$C_{3-6}$ carbocyclyl substituted with 0-3 $R^e$, or —$(CH_2)_n$-heterocyclyl comprising 1-4 heteroatoms selected from O, $S(=O)_p$, and N, and substituted with 0-3 $R^e$;

$R^{10}$ is H, $C_{1-4}$ alkyl substituted with 0-2 $R^{11}$, —$C(=O)R^1$, —$C(=O)OR^b$, —$C(=O)NR^aR^a$, $C_{3-6}$ cycloalkyl substituted with 0-5 $R^e$, or a 4- to 6-membered heterocyclyl comprising 1-4 heteroatoms selected from O, $S(=O)_p$, N and $NR^{12}$—, and substituted with 0-5 $R^e$;

$R^{11}$ is —OH, —C(=O)OH, or aryl;

$R^{12}$ is H, $C_{1-3}$ alkyl, or aryl;

$R^a$ is H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$ carbocyclyl substituted with 0-5 $R^e$, or —$(CH_2)_n$-heterocyclyl substituted with 0-5 $R^e$; or $R^a$ and $R^a$ together with the nitrogen atom to which they are both attached form a heterocyclyl substituted with 0-5 $R^e$;

$R^b$ is H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, or —$(CH_2)_n$-heterocyclyl substituted with 0-5 $R^e$;

$R^c$ is $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $C_{3-6}$ carbocyclyl, or heterocyclyl;

$R^d$ is H or $C_{1-4}$ alkyl;

$R^e$ is halo, CN, $NO_2$, =O, $C_{1-6}$ alkyl substituted with 0-5 $R^g$, $C_{2-6}$ alkenyl substituted with 0-5 $R^g$, $C_{2-6}$ alkynyl substituted with 0-5

$R^g$, —$(CH_2)_n$-carbocyclyl, —$(CH_2)_n$-heterocyclyl, —$(CH_2)_nOR^f$, —$C(=O)OR^f$, —$C(=O)NR^fR^f$, —$NR^fC(=O)R^f$, —$S(=O)_pR^f$, —$S(=O)_pNR^fR^f$, —$NR^fS(=O)_pR^f$, —$NR^fC(=O)OR^f$, —$OC(=O)NR^fR^f$, or —$(CH_2)_nNR^fR^f$;

$R^f$ is H, $C_{1-4}$ alkyl, $C_{3-6}$ cycloalkyl, aryl, or heterocyclyl; or $R^f$ and $R^f$ together with the nitrogen atom to which they are both attached form a heterocyclyl;

$R^g$ is halo, CN, OH, $C_{1-6}$alkyl, $C_{3-6}$ cycloalkyl, or aryl;

n is zero, 1, 2, or 3; and p is zero, 1, or 2.

In a second aspect within the scope of the first aspect, the present invention provides compounds of Formula (II):

(II)

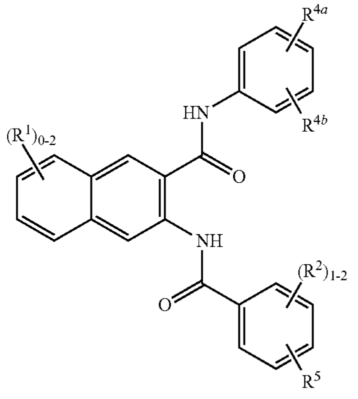

or pharmaceutically acceptable salts thereof, wherein:

$R^1$ is halo or $C_{1-3}$ alkyl substituted with 0-4 halo;

$R^2$ is halo, —$OC_{1-3}$ alkyl, or $C_{1-3}$ alkyl;

$R^{4a}$ is halo;

$R^{4b}$ is $C_{1-4}$ alkyl substituted with 0-4 halo;

$R^5$ is —$S(=O)_pR^c$, $C_{2-6}$ alkynyl substituted with 0-5 halo or OH, $C_6$ aryl substituted with 0-3 $R^6$ and 0-2 $R^7$, or a 3- to 12-membered heterocyclyl comprising 1-4 heteroatoms selected from O, $S(=O)_p$, N and $NR^{10}$ substituted with 0-3 $R^6$ and 0-1 $R^7$;

$R^6$ is halo, =O, —OH, —$OC_{1-4}$ alkyl, or $C_{1-4}$ alkyl substituted with 0-2 halo or OH;

$R^7$ is $C_{1-3}$ alkyl substituted with 0-1 $R^8$ and 0-1 $R^9$, —$OR^b$, —$NR^aR^a$, —$NR^aC(=O)R^b$, —$NR^aC(=O)OR^b$, —$NR^aC(=O)NR^aR^a$, —$NR^aS(=O)_pR^c$, —$C(=O)R^b$, —$C(=O)OR^b$, —$C(=O)NR^aR^a$, —$C(=O)NR^aS(=O)_pR^c$, —$OC(=O)R^b$, —$S(=O)_pR^c$, —$S(=O)_pNR^aR^a$, $C_{3-6}$ cycloalkyl, or a 4- to 6-membered heterocyclyl comprising 1-4 heteroatoms selected from O, $S(=O)_p$, N and $NR^d$, and substituted with 0-5 $R^e$;

$R^8$ is halo, —$C(=O)OR^b$, —$C(=O)NHR^a$, —$C(=O)NHOR^b$, or $C_{1-4}$ alkyl substituted with 0-3 halo or OH;

$R^9$ is —$OR^b$, —$NR^aR^a$, —$NR^aC(=O)R^b$, —$NR^aC(=O)OR^b$, —$NR^aS(=O)_pR^c$, —$NR^aS(O)_pNR^aR^a$, —$OC(=O)NR^aR^a$, —$OC(=O)NR^aOR^b$, —$S(=O)_pNR^aR^a$, or —$S(O)_pR^c$;

$R^{10}$ is H, $C_{1-4}$ alkyl substituted with 0-2 $R^{11}$, —$C(=O)R^b$, —$C(=O)OR^b$, —$C(=O)NR^aR^a$, $C_{3-6}$ cycloalkyl substituted with 0-5 $R^e$, or a 4- to 6-membered heterocyclyl comprising 1-4 heteroatoms selected from O, $S(=O)_p$, N and $NR^{12}$, and substituted with 0-5 $R^e$;

$R^{11}$ is —OH, —C(=O)OH, or aryl;

$R^{12}$ is H, $C_{1-3}$ alkyl, or aryl;

$R^a$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, —$(CH_2)_n$—$C_{3-10}$ carbocyclyl substituted with 0-5 $R^e$, or —$(CH_2)_n$-heterocyclyl substituted with 0-5 $R^e$; or $R^a$ and $R^a$ together with the nitrogen atom to which they are both attached form a heterocyclyl substituted with 0-5 $R^e$;

$R^b$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, —$(CH_2)_n$—$C_{3-10}$ carbocyclyl substituted with 0-5 $R^e$, or —$(CH_2)_n$-heterocyclyl substituted with 0-5 $R^e$;

$R^c$ is $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $C_{3-6}$ carbocyclyl, or heterocyclyl;

$R^d$ is H or $C_{1-4}$ alkyl;

$R^e$ is halo, CN, =O, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, $-(CH_2)_n-C_{3-6}$ cycloalkyl, $-(CH_2)_n$-aryl, $-(CH_2)_n$-heterocyclyl, $-(CH_2)_nOR^f$, $-C(=O)OR^f$, $-C(=O)NR^fR^f$, $-NR^fC(=O)R^f$, $-S(=O)_pR^f$, $-NR^fC(=O)OR^f$, $-OC(=O)NR^fR^f$, or $-(CH_2)_nNR^fR^f$;

$R^f$ is H, $C_{1-5}$ alkyl, $C_{3-6}$ cycloalkyl, or aryl; or $R^f$ and $R^f$ together with the nitrogen atom to which they are both attached form a heterocyclyl;

$R^g$ is halo, CN, OH, $C_{1-6}$ alkyl, $C_{3-6}$ cycloalkyl, or aryl;

n is zero, 1, 2, or 3; and p is zero, 1, or 2.

In a third aspect within the scope of the first and second aspects, the present invention provides compounds of Formula (III):

(III)

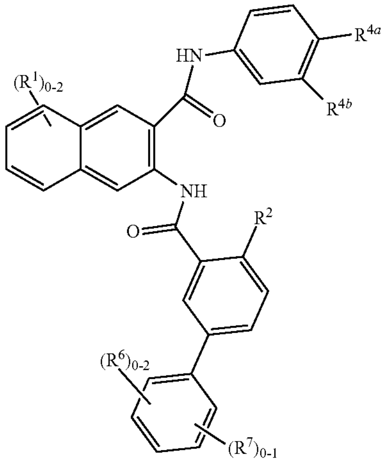

or pharmaceutically acceptable salts thereof, wherein:

$R^1$ is Br or $CF_3$;

$R^2$ is $-OC_{1-4}$ alkyl substituted with 0-4 halo;

$R^{4a}$ is halo;

$R^{4b}$ is $C_{1-3}$ alkyl substituted with 0-4 F;

$R^6$ is halo, CN, $C_{1-3}$ alkyl, $-OH$, or $-OC_{1-4}$ alkyl;

$R^7$ is $C_{1-2}$ alkyl substituted with 0-1 $R^8$ and 0-1 $R^9$, $OR^b$, $-NR^aR^a$, $-NR^aC(=O)R^b$, $-NR^aC(=O)NR^aR^a$, $-NR^aS(=O)_pR^c$, $-C(=O)R^b$, $-C(=O)OR^b$, $-C(=O)NR^aR^a$, $-C(=O)NR^aS(=O)_pR^c$, $-OC(=O)R^b$, $-S(=O)_pR^c$, $-S(=O)_pNR^aR^a$, or $C_{3-6}$ cycloalkyl;

$R^8$ is halo, $-C(=O)OR^b$, $-C(=O)NHR^a$, or $C_{1-3}$ alkyl substituted with 0-3 halo or OH;

$R^9$ is $-OR^b$, $-NR^aR^a$, $-NR^aC(=O)R^b$, $-NR^aC(O)OR^b$, $-NR^aS(=O)_pR^c$, $-OC(=O)NR^aR^a$, $-OC(=O)NR^aOR^b$, $-S(=O)_pNR^aR^a$, or $-S(O)_pR^c$;

$R^a$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, $-(CH_2)_n-C_{3-10}$ carbocyclyl substituted with 0-4 $R^e$, or $-(CH_2)_n$-heterocyclyl substituted with 0-4 $R^e$; or $R^a$ and $R^a$ together with the nitrogen atom to which they are both attached form a heterocyclyl substituted with 0-4 $R^e$;

$R^b$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, $-(CH_2)_n-C_{3-10}$ carbocyclyl substituted with 0-4 $R^e$, or $-(CH_2)_n$-heterocyclyl substituted with 0-4 $R^e$;

$R^c$ is $C_{1-5}$ alkyl substituted with 0-4 $R^e$, $C_{2-3}$ alkenyl substituted with 0-4 $R^e$, $C_{2-5}$ alkynl substituted with 0-4 $R^e$, $C_{3-6}$ carbocyclyl, or heterocyclyl;

$R^d$ is H or $C_{1-2}$ alkyl;

$R^e$ is halo, CN, =O, $C_{1-5}$ alkyl substituted with 0-5 $R^g$, $C_{2-6}$ alkenyl substituted with 0-5 $R^g$, $C_{2-6}$ alkynyl substituted with 0-5 $R^g$, $-(CH_2)_n-C_{3-6}$ cycloalkyl, $-(CH_2)_n$-aryl, $-(CH_2)_n$-heterocyclyl, $-(CH_2)_nOR^f$, $S(=O)_pR^f$, $C(=O)NR^fR^f$, $C(=O)OR^f$, $NR^fC(=O)R^f$, $S(=O)_pNR^fR^f$, $NR^fS(=O)_pR^f$, $NR^fC(=O)OR^f$, $OC(=O)NR^fR^f$, or $-(CH_2)_nNR^fR^f$;

$R^f$ is H, $C_{1-6}$ alkyl, $C_{3-6}$ cycloalkyl, or aryl; or $R^f$ and $R^f$ together with the nitrogen atom to which they are both attached form a heterocyclyl;

$R^g$ is halo, CN, OH, $C_{1-6}$ alkyl, $C_{3-6}$ cycloalkyl, or aryl;

n is zero, 1, 2, or 3; and p is zero, 1, or 2.

In a fourth aspect within the scope of the first to third aspects, the present invention provides compounds of Formula (IV):

(IV)

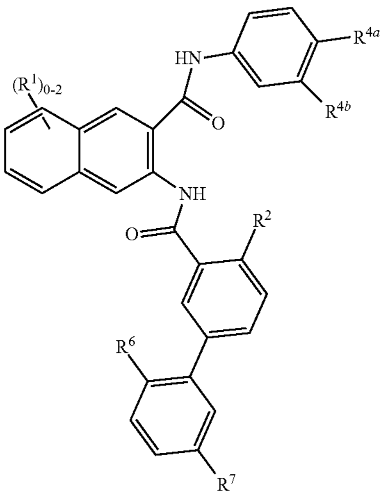

or pharmaceutically acceptable salts thereof, wherein:

$R^1$ is Br;

$R^2$ is $-OC_{1-3}$ alkyl;

$R^{fa}$ is F;

$R^{4b}$ is $CF_3$;

$R^6$ is halo;

$R^7$ is $C_{1-2}$ alkyl substituted with 0-1 $R^8$ and 0-1 $R^9$, $-C(=O)OR^b$, $-C(=O)NR^aR^a$;

$R^8$ is $-C(=O)OR^b$, $-C(=O)NHR^a$, or $C_{1-3}$ alkyl substituted with 0-3 halo or OH $R^9$ is $-OR^b$, $-NR^aR^a$, $-NR^aC(=O)R^b$, or $-OC(=O)NR^aR^a$;

$R^a$ is H, $C_{1-3}$ alkyl substituted with 0-3 $R^e$, $-(CH_2)_n-C_{3-6}$ cycloalkyl substituted with 0-3 $R^e$, phenyl substituted with 0-3 $R^e$;

$R^b$ is H or heterocyclyl substituted with 0-3 $R^e$;

$R^e$ is halo, CN, =O, or $C_{1-6}$ alkyl; and n is zero or 1.

In a fifth aspect within the scope of the first and second aspects, the present invention provides compounds of Formula (V):

(V)

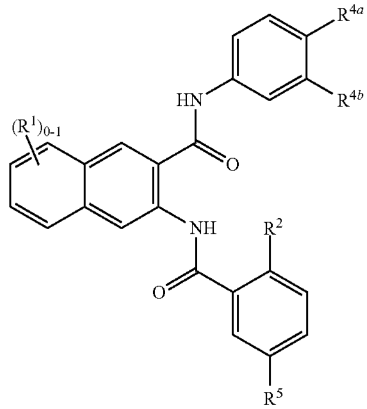

or pharmaceutically acceptable salts thereof, wherein:

$R^1$ is halo or $C_{1-3}$ alkyl substituted with 0-5 halo;

$R^2$ is —$OC_{1-4}$ alkyl substituted with 0-4 halo;

$R^{4a}$ is halo;

$R^{4b}$ is $C_{1-3}$ alkyl substituted with 0-4 halo;

$R^5$ is a 3- to 12-membered heterocyclyl comprising 1-4 heteroatoms selected from O, S(═O)$_p$, N and $NR^{10}$ substituted with 0-3 $R^6$ and 0-1 $R^7$;

$R^6$ is halo, ═O, —OH, —$OC_{1-4}$ alkyl, or $C_{1-4}$ alkyl substituted with 0-2 halo or OH;

$R^7$ is $C_{1-2}$ alkyl substituted with 0-1 $R^8$ and 0-1 $R^9$, —$OR^b$, —$NR^aR^a$, —$NR^aC$(═O)$R^b$, —$NR^aC$(═O)$OR^b$, —$NR^aC$(═O)$NR^aR^a$, —$NR^aS$(═O)$_pR^c$, —C(═O)$R^b$, —C(═O)$OR^b$, —C(═O)$NR^aR^a$, —C(═O)$NR^aS$(═O)$_pR^c$, —OC(═O)$R^b$, —S(═O)$_pR^c$, —S(═O)$_pNR^aR^a$, $C_{3-6}$ cycloalkyl, or a 4- to 6-membered heterocyclyl comprising 1-4 heteroatoms selected from O, S(═O)$_p$, N and $NR^d$, and substituted with 0-4 $R^e$;

$R^8$ is —C(═O)$OR^b$, —C(═O)$NHR^a$, —C(═O)$NHOR^b$, or $C_{1-4}$ alkyl substituted with 0-3 halo or OH;

$R^9$ is —$OR^b$, —$NR^aR^a$, —$NR^aC$(═O)$R^b$, —$NR^aC$(═O)$OR^b$, —$NR^aS$(═O)$_pR^c$, —$NR^aS(O)_pNR^aR^a$, —OC(═O)$NR^aR^a$, —S(═O)$_pNR^aR^a$, or —$S(O)_pR^c$;

$R^{10}$ is H, $C_{1-4}$ alkyl substituted with 0-2 $R^{11}$, —C(═O)$R^b$, —C(═O)$OR^b$, —C(═O)$NR^aR^a$, $C_{3-6}$ cycloalkyl substituted with 0-5 $R^e$, or a 4- to 6-membered heterocyclyl comprising 1-4 heteroatoms selected from O, S(═O)$_p$, N and $NR^{12}$, and substituted with 0-5 $R^e$;

$R^{11}$ is —OH, —C(═O)OH, or aryl;

$R^{12}$ is H, $C_{1-3}$ alkyl, or aryl;

$R^a$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, —$(CH_2)_n$—$C_{3-10}$ carbocyclyl substituted with 0-4 $R^c$, or —$(CH_2)_n$-heterocyclyl substituted with 0-4 $R^e$; or $R^a$ and $R^a$ together with the nitrogen atom to which they are both attached form a heterocyclyl substituted with 0-4 $R^e$;

$R^b$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, —$(CH_2)_n$—$C_{3-10}$carbocyclyl substituted with 0-4 $R^e$, or —$(CH_2)_n$-heterocyclyl substituted with 0-4 $R^e$;

$R^c$ is $C_{1-5}$ alkyl substituted with 0-4 $R^e$, $C_{2-5}$ alkenyl substituted with 0-4 $R^e$, $C_{2-5}$ alkynyl substituted with 0-4 $R^e$, $C_{3-6}$ carbocyclyl, or heterocyclyl;

$R^d$ is H or $C_{1-2}$ alkyl;

$R^e$ is halo, CN, $NO_2$, ═O, C(═O)$OR^f$, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, —$(CH_2)_n$—$C_{3-6}$ cycloalkyl, —$(CH_2)_n$-aryl, —$(CH_2)_n$-heterocyclyl, —$(CH_2)_nOR^f$, S(═O)$_pR^f$, C(═O)$NR^fR^f$, $NR^fC$(═O)$R^f$, S(═O)$_pNR^fR^f$, $NR^fS$(═O)$_pR^f$, $NR^fC$(═O)$OR^f$, OC(═O)$NR^fR^f$, or —$(CH_2)_nNR^fR^f$;

$R^f$ is H, $C_{1-6}$ alkyl, $C_{3-6}$ cycloalkyl, or aryl; or $R^f$ and $R^f$ together with the nitrogen atom to which they are both attached form a heterocyclyl;

$R^g$ is halo, CN, OH, $C_{1-6}$ alkyl, $C_{3-6}$ cycloalkyl, or aryl;

n is zero, 1, 2, or 3; and p is zero, 1, or 2.

In a sixth aspect within the scope of the fifth aspect, the present invention provides compounds of Formula (V) or pharmaceutically acceptable salts thereof, wherein:

$R^2$ is —$OCH_3$;

$R^{4a}$ is F;

$R^{4b}$ is $CF_3$;

$R^5$ is

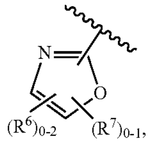,
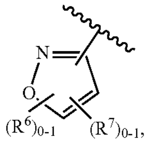,
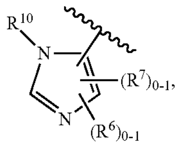,
or
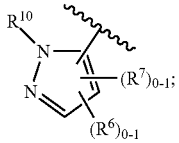;

$R^6$ is halo, —OH, or $C_{1-4}$ alkyl substituted with 0-1 OH;

$R^7$ is $C_{1-2}$ alkyl substituted with 0-1 $R^8$ and 0-1 $R^9$;

$R^8$ is —C(═O)$OR^b$, —C(═O)$NHR^a$, or —C(═O)$NHOR^b$;

$R^9$ is —$OR^b$ or —$NR^aR^a$ $R^{10}$ is H or $C_{1-3}$ alkyl;

$R^a$ is H or $C_{1-6}$ alkyl; and $R^b$ is H or $C_{1-6}$ alkyl.

In a seventh aspect within the scope of the fifth aspect, the present invention provides compounds of Formula (V) or pharmaceutically acceptable salts thereof, wherein:

$R^2$ is —$OCH_3$;

$R^{4a}$ is F;

$R^{4b}$ is $CF_3$;

$R^5$ is

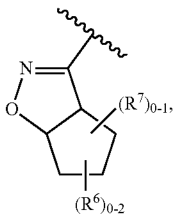,
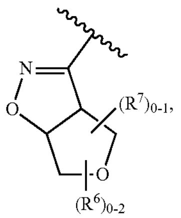,

-continued

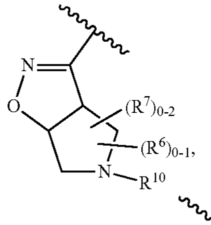

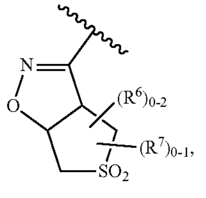

or

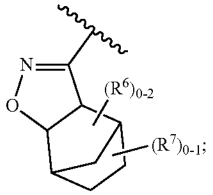

$R^6$ is halo, $C_{1-4}$ alkyl, —OH, or —$OC_{1-4}$ alkyl;

$R^7$ is $C_{1-4}$ alkyl substituted with 0-1 $R^8$ and 0-1 $R^9$;

$R^8$ is —C(═O)$OR^b$;

$R^9$ is OH;

$R^{10}$ is H, $C_{1-3}$ alkyl substituted with 0-2 $R^{11}$, or —C(═O)$OC_{1-4}$ alkyl;

$R^{11}$ is —OH, —C(═O)OH, or aryl; and $R^b$ is H or $C_{1-4}$ alkyl.

In an eighth aspect within the scope of the fifth aspect, the present invention provides compounds of Formula (V), or pharmaceutically acceptable salts thereof, wherein:

$R^2$ is —$OCH_3$;

$R^{4a}$ is F;

$R^{4b}$ is $CF_3$;

$R^5$ is

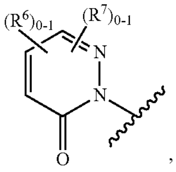

,

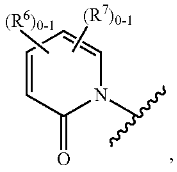

,

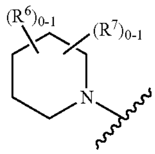

,

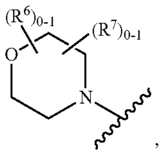

,

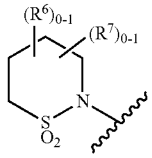

,

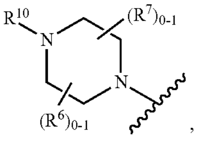

,

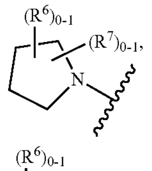

,

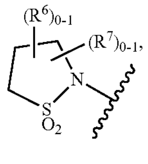

or

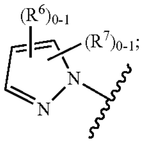

$R^6$ is halo, CN, $C_{1-4}$ alkyl, ═O, —OH, or —$OC_{1-4}$ alkyl;

$R^7$ is $C_{1-2}$ alkyl substituted with 0-1 $R^8$ and 0-1 $R^9$, —$NR^aR^a$, —$NR^a$C(═O)$R^b$, —$NR^a$C(═O)$OR^b$, or —C(═O)$OR^b$;

$R^8$ is —C(═O)$OR^b$, —C(═O)$NHR^a$, —C(═O)$NHOR^b$, or $C_{1-4}$ alkyl substituted with 0-3 halo or OH;

$R^9$ is —$NR^a$C(═O)$R^b$;

$R^{10}$ is H or $C_{1-3}$ alkyl, $R^a$ is H or $C_{1-4}$ alkyl; and $R^b$ is H or $C_{1-4}$ alkyl.

In a ninth aspect within the scope of the first aspect, the present invention provides compounds of Formula (I), or pharmaceutically acceptable salts thereof, wherein:

$R^5$ is —S(═O)$_2R^c$;

$R^{4a}$ is halo;

$R^{4b}$ is $C_{1-3}$ alkyl substituted with 0-4 halo;

$R^c$ is $C_{1-3}$ alkyl substituted with 0-2 $R^e$;

$R^e$ is —$OR^f$, and $R^f$ is H or $C_{1-2}$ alkyl.

In a tenth aspect within the scope of the first aspect, the present invention provides compounds of Formula (VI):

(VI)

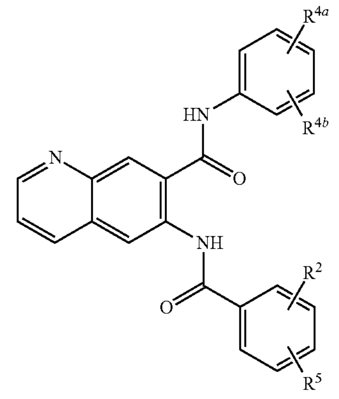

or pharmaceutically acceptable salts thereof, wherein:

$R^2$ is —$OC_{1-3}$ alkyl;

$R^{4a}$ is halo;

$R^{4b}$ is $C_{1-4}$ alkyl substituted with 0-4 halo;

$R^5$ is $C_6$ aryl substituted with 0-3 $R^6$ and 0-2 $R^7$, or a 3- to 12-membered heterocyclyl comprising 1-4 heteroatoms selected from O, S(═O)$_p$, N and $NR^{10}$ substituted with 0-3 $R^6$ and 0-1 $R^7$;

$R^6$ is halo, ═O, —OH, —$OC_{1-4}$ alkyl, or $C_{1-4}$ alkyl substituted with 0-2 halo or OH;

$R^7$ is $C_{1-3}$ alkyl substituted with 0-1 $R^8$ and 0-1 $R^9$, —$OR^b$, —$NR^aR^a$, —$NR^a$C(═O)$R^b$, —$NR^a$C(═O)$OR^b$, —$NR^a$C(═O)$NR^aR^a$, —$NR^a$S(═O)$_pR^c$, —C(═O)$R^b$, —C(═O)$OR^b$, —C(═O)$NR^aR^a$, —C(═O)$NR^a$S(═O)$_pR^c$, —OC(═O)$R^b$, —S(═O)$_pR^b$, —S(═O)$_pNR^aR^a$, $C_{3-6}$ cycloalkyl, or a 4- to 6-membered heterocyclyl comprising 1-4 heteroatoms selected from O, S(═O)$_p$, N and $NR^d$, and substituted with 0-5 $R^e$;

$R^8$ is halo, —C(═O)$OR^b$, —C(═O)$NHR^a$, —C(═O)$NHOR^b$, or $C_{1-4}$ alkyl substituted with 0-3 halo or OH;

$R^9$ is —$OR^b$, —$NR^aR^a$, —$NR^a$C(═O)$R^b$, —$NR^a$C(═O)$OR^b$, —$NR^a$S(═O)$_pR^c$, —$NR^a$S(O)$_pNR^aR^a$, —OC(═O)$NR^aR^a$, —OC(═O)$NR^aOR^b$, —S(═O)$_pNR^aR^a$, or —S(O), $R^{10}$ is H, $C_{1-4}$ alkyl substituted with 0-2 $R^{11}$, —C(═O)$R^b$, —C(═O)$OR^b$, —C(═O)$NR^aR^a$, $C_{3-6}$ cycloalkyl substituted with 0-5 $R^e$, or a 4- to 6-membered heterocyclyl comprising 1-4 heteroatoms selected from O, S(═O)$_p$, N and $NR^{12}$, and substituted with 0-5 $R^e$;

$R^{11}$ is —OH, —C(═O)OH, or aryl;

$R^{12}$ is H, $C_{1-3}$ alkyl, or aryl;

$R^a$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $—(CH_2)_n—C_{3-10}$ carbocyclyl substituted with 0-5 $R^e$, or $—(CH_2)_n$-heterocyclyl substituted with 0-5 $R^e$; or $R^a$ and $R^a$ together with the nitrogen atom to which they are both attached form a heterocyclyl substituted with 0-5 $R^e$;

$R^b$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $—(CH_2)_n—C_{3-10}$carbocyclyl substituted with 0-5 $R^e$, or $—(CH_2)_n$-heterocyclyl substituted with 0-5 $R^e$;

$R^c$ is $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $C_{3-6}$ carbocyclyl, or heterocyclyl;

$R^d$ is H or $C_{1-4}$ alkyl;

$R^e$ is halo, CN, ═O, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, $—(CH_2)_n—C_{3-6}$ cycloalkyl, $—(CH_2)_n$-aryl, $—(CH_2)_n$-heterocyclyl, $—(CH_2)_nOR^f$, $—C(═O)OR^f$, $—C(═O)NR^fR^f$, $—NR^fC(═O)R^f$, $—S(═O)_pR^f$, $—NR^fC(═O)OR^f$, $—OC(═O)NR^fR^f$, or $—(CH_2)_nNR^fR^f$;

$R^f$ is H, $C_{1-5}$ alkyl, $C_{3-6}$ cycloalkyl, or aryl; or $R^f$ and $R^1$ together with the nitrogen atom to which they are both attached form a heterocyclyl;

$R^g$ is halo, CN, OH, $C_{1-6}$alkyl, $C_{3-6}$ cycloalkyl, or aryl;

n is zero, 1, 2, or 3; and p is zero, 1, or 2.

In an eleventh aspect within the scope of the first aspect, the present invention provides compounds of Formula (VII):

(VII)

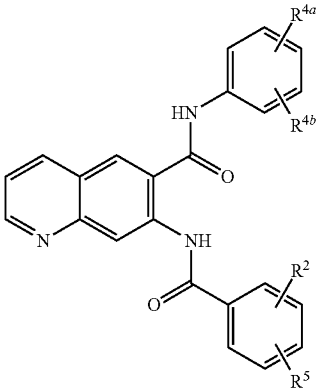

or pharmaceutically acceptable salts thereof, wherein:

$R^2$ is $—OC_{1-3}$ alkyl;

$R^{4a}$ is halo;

$R^{4b}$ is $C_{1-4}$ alkyl substituted with 0-4 halo;

$R^5$ is $C_6$ aryl substituted with 0-3 $R^6$ and 0-2 $R^7$, or a 3- to 12-membered heterocyclyl comprising 1-4 heteroatoms selected from O, $S(═O)_p$, N and $NR^{10}$ substituted with 0-3 $R^6$ and 0-1 $R^7$;

$R^6$ is halo, ═O, —OH, $—OC_{1-4}$ alkyl, or $C_{1-4}$ alkyl substituted with 0-2 halo or OH;

$R^7$ is $C_{1-3}$ alkyl substituted with 0-1 $R^8$ and 0-1 $R^9$, $—OR^b$, $—NR^aR^a$, $—NR^aC(═O)R^b$, $—NR^aC(═O)OR^b$, $—NR^aC(═O)NR^aR^a$, $—NR^aS(═O)_pR^c$, $—C(═O)R^b$, $—C(═O)OR^b$, $—C(═O)NR^aR^a$, $—C(═O)NR^aS(═O)_pR^c$, $—OC(═O)R^b$, $—S(═O)_pR^c$, $—S(═O)_pNR^aR^a$, $C_{3-6}$ cycloalkyl, or a 4- to 6-membered heterocyclyl comprising 1-4 heteroatoms selected from O, $S(═O)_p$, N and $NR^d$, and substituted with 0-5 $R^e$;

$R^8$ is halo, $—C(═O)OR^b$, $—C(═O)NHR^a$, $—C(═O)NHOR^b$, or $C_{1-4}$ alkyl substituted with 0-3 halo or OH;

$R^9$ is $—OR^b$, $—NR^aR^a$, $—NR^aC(═O)R^b$, $—NR^aC(═O)OR^b$, $—NR^aS(═O)_pR^c$, $—NR^aS(O)_pNR^aR^a$, $—OC(═O)NR^aR^a$, $—OC(═O)NR^aOR^b$, $—S(═O)_pNR^aR^a$, or $—S(O)_pR^c$;

$R^{10}$ is H, $C_{1-4}$ alkyl substituted with 0-2 $R^{11}$, $—C(═O)R^b$, $—C(═O)OR^b$, $—C(═O)NR^aR^a$, $C_{3-6}$ cycloalkyl substituted with 0-5 $R^e$, or a 4- to 6-membered heterocyclyl comprising 1-4 heteroatoms selected from O, $S(═O)_p$, N and $NR^{12}$, and substituted with 0-5 $R^e$;

$R^{11}$ is —OH, —C(═O)OH, or aryl;

$R^{12}$ is H, $C_{1-3}$ alkyl, or aryl;

$R^a$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $—(CH_2)_n—C_{3-10}$ carbocyclyl substituted with 0-5 $R^e$, or $—(CH_2)_n$-heterocyclyl substituted with 0-5 $R^e$; or $R^a$ and $R^a$ together with the nitrogen atom to which they are both attached form a heterocyclyl substituted with 0-5 $R^e$;

$R^b$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $—(CH_2)_n—C_{3-10}$carbocyclyl substituted with 0-5 $R^e$, or $—(CH_2)_n$-heterocyclyl substituted with 0-5 $R^e$;

$R^c$ is $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $C_{3-6}$ carbocyclyl, or heterocyclyl;

$R^d$ is H or $C_{1-4}$ alkyl;

$R^e$ is halo, CN, ═O, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, $—(CH_2)_n—C_{3-6}$ cycloalkyl, $—(CH_2)_n$-aryl, $—(CH_2)_n$-heterocyclyl, $—(CH_2)_nOR^f$, $—C(═O)OR^f$, $—C(═O)NR^fR^f$, $—NR^fC(═O)R^f$, $—S(═O)_pR^f$, $—NR^fC(═O)OR^f$, $—OC(═O)NR^fR^f$, or $—(CH_2)_nNR^fR^f$;

$R^f$ is H, $C_{1-5}$ alkyl, $C_{3-6}$ cycloalkyl, or aryl; or $R^f$ and $R^f$ together with the nitrogen atom to which they are both attached form a heterocyclyl;

$R^g$ is halo, CN, OH, $C_{1-6}$ alkyl, $C_{3-6}$ cycloalkyl, or aryl;

n is zero, 1, 2, or 3; and p is zero, 1, or 2.

In a twelfth aspect within the scope of the first aspect, the present invention provides compounds of Formula (VIII):

(VIII)

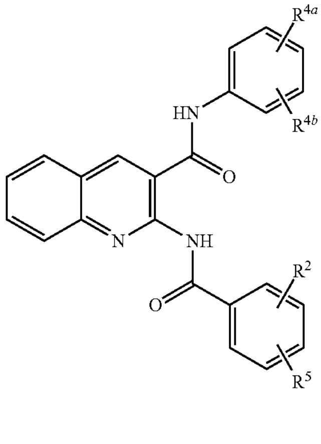

or pharmaceutically acceptable salts thereof, wherein:

$R^2$ is —$OC_{1-3}$ alkyl;

$R^{4a}$ is halo;

$R^{4b}$ is $C_{1-4}$ alkyl substituted with 0-4 halo;

$R^5$ is $C_6$ aryl substituted with 0-3 $R^6$ and 0-2 $R^7$, or a 3- to 12-membered heterocyclyl comprising 1-4 heteroatoms selected from O, $S(=O)_p$, N and $NR^{10}$ substituted with 0-3 $R^6$ and 0-1 $R^7$;

$R^6$ is halo, =O, —OH, —$OC_{1-4}$ alkyl, or $C_{1-4}$ alkyl substituted with 0-2 halo or OH;

$R^7$ is $C_{1-3}$ alkyl substituted with 0-1 $R^8$ and 0-1 $R^9$, —$OR^b$, —$NR^aR^a$, —$NR^aC(=O)R^b$, —$NR^aC(=O)OR^b$, —$NR^aC(=O)NR^aR^a$, —$NR^aS(=O)_pR^c$, —$C(=O)R^b$, —$C(=O)OR^b$, —$C(=O)NR^aR^a$, —$C(=O)NR^aS(=O)_pR^c$, —$OC(=O)R^b$, —$S(=O)_pR^c$, —$S(=O)_pNR^aR^a$, $C_{3-6}$ cycloalkyl, or a 4- to 6-membered heterocyclyl comprising 1-4 heteroatoms selected from O, $S(=O)_p$, N and $NR^d$, and substituted with 0-5 $R^e$;

$R^8$ is halo, —$C(=O)OR^b$, —$C(=O)NHR^a$, —$C(=O)NHOR^b$, or $C_{1-4}$ alkyl substituted with 0-3 halo or OH;

$R^9$ is —$OR^b$, —$NR^aR^a$, —$NR^aC(=O)R^b$, —$NR^aC(=O)OR^b$, —$NR^aS(=O)_pR^c$, —$NR^aS(O)_pNR^aR^a$, —$OC(=O)NR^aR^a$, —$OC(=O)NR^aOR^b$, —$S(=O)_pNR^aR^a$, or —$S(O)_pR^c$;

$R^{10}$ is H, $C_{1-4}$ alkyl substituted with 0-2 $R^{11}$, —$C(=O)R^b$, —$C(=O)OR^b$, —$C(=O)NR^aR^a$, $C_{3-6}$ cycloalkyl substituted with 0-5 $R^e$, or a 4- to 6-membered heterocyclyl comprising 1-4 heteroatoms selected from O, $S(=O)_p$, N and $NR^{12}$, and substituted with 0-5 $R^e$, $R^{11}$ is —OH, —C(=O)OH, or aryl;

$R^{12}$ is H, $C_{1-3}$ alkyl, or aryl;

$R^a$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, —$(CH_2)_n$—$C_{3-10}$ carbocyclyl substituted with 0-5 $R^e$, or —$(CH_2)_n$-heterocyclyl substituted with 0-5 $R^e$; or $R^a$ and $R^a$ together with the nitrogen atom to which they are both attached form a heterocyclyl substituted with 0-5 $R^e$;

$R^b$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, —$(CH_2)_n$—$C_{3-10}$carbocyclyl substituted with 0-5 $R^e$, or —$(CH_2)_n$-heterocyclyl substituted with 0-5 $R^e$;

$R^c$ is $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $C_{3-6}$ carbocyclyl, or heterocyclyl;

$R^d$ is H or $C_{1-4}$ alkyl;

$R^e$ is halo, CN, =O, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, —$(CH_2)_n$—$C_{3-6}$ cycloalkyl, —$(CH_2)_n$-aryl, —$(CH_2)_n$-heterocyclyl, —$(CH_2)_nOR^f$, —$C(=O)OR^f$, —$C(=O)NR^fR^f$, —$NR^fC(=O)R^f$, —$S(=O)_pR^f$, —$NR^fC(=O)OR^f$, —$OC(=O)NR^fR^f$, or —$(CH_2)_nNR^fR^f$;

$R^f$ is H, $C_{1-5}$ alkyl, $C_{3-6}$ cycloalkyl, or aryl; or $R^f$ and $R^f$ together with the nitrogen atom to which they are both attached form a heterocyclyl;

$R^g$ is halo, CN, OH, $C_{1-6}$ alkyl, $C_{3-6}$ cycloalkyl, or aryl;

n is zero, 1, 2, or 3; and p is zero, 1, or 2.

For a compound of Formula (I), the scope of any instance of a variable substituent, including $R^1$, $R^2$, $R^3$. $R^4$ ($R^{48}$, $R^{4b}$), $R^5$, $R^6$, $R^7$, $R^8$, $R^9$, $R^{10}$, $R^{11}$, $R^{12}$, $R^a$, $R^b$, $R^c$, $R^d$, $R^e$, $R^f$, and $R^g$ can be used independently with the scope of any other instance of a variable substituent. As such, the invention includes combinations of the different aspects.

In one embodiment of Formula (II), $R^{4a}$ is F.

In another embodiment of Formula (II), $R^{4b}$ is $CF_3$.

In another embodiment of Formula (II), $R^1$ is absent or halo; $R^2$ is F or —$OCH_3$; $R^{4a}$ is F; $R^{4b}$ is $CF_3$; $R^5$ is

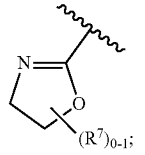

$R^7$ is —$C(=O)NR^aR^a$; $R^a$ and $R^a$ together with the nitrogen atom to which they are both attached form

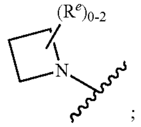

$R^e$ is $C_{1-3}$ alkyl substituted with 0-2 $R^g$; $R^g$ is —OH alkyl.

In another embodiment of Formula (II), $R^1$ is absent or halo; $R^2$ is F or —$OCH_3$; $R^{4a}$ is F; $R^{4b}$ is $CF_3$; $R^5$ is

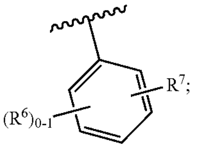

$R^6$ is F; $R^7$ is —$S(=O)_2C_{1-3}$ alkyl, —$S(=O)_2NHR^a$, or $C_{1-3}$ alkyl substituted with 0-1 $R^8$ and 0-1 $R^9$; $R^8$ is —C(=O)OH, or $CF_3$; $R^9$ is —$NHR^a$, —$NHC(=O)R^b$, —$NHS(=O)_pC_{1-4}$ alkyl or —$OC(=O)NHR^a$; $R^a$ is H, $C_{1-3}$ alkyl, —$(CH_2)_{0-1}$—$C_{3-6}$ cycloalkyl, or —$(CH_2)_{0-1}$-phenyl substituted with 0-2 $R^e$; $R^b$ is H or heterocyclyl; $R^e$ is $C_{1-3}$ alkyl, —$(CH_2)_{0-1}OR^f$; and $R^f$ is H or $C_{1-3}$ alkyl.

In another embodiment of Formula (II), $R^1$ is absent or halo; $R^2$ is —$OCH_3$; $R^{4a}$ is F; $R^{4b}$ is $CF_3$; $R^5$ is

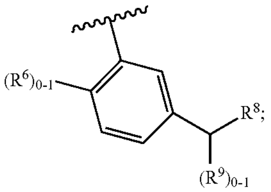

$R^6$ is F; $R^8$ is —C(=O)OH, or $CF_3$; $R^9$ is —$NHR^a$, —$NHC(=O)R^b$, —$NHS(=O)_pC_{1-4}$ alkyl or —$OC(=O)NHR^a$; $R^a$ is H, $C_{1-3}$ alkyl, —$(CH_2)_{0-1}$—$C_{3-6}$ cycloalkyl, or —$(CH_2)_{0-1}$-phenyl substituted with 0-2 $R^e$; $R^b$ is H or heterocyclyl; $R^e$ is $C_{1-3}$ alkyl, —$(CH_2)_{0-1}OR^f$; and $R^f$ is H or $C_{1-3}$ alkyl.

In another embodiment of Formula (II), $R^1$ is absent or halo; $R^2$ is F or —$OCH_3$; $R^{4a}$ is F; $R^{4b}$ is $CF_3$; $R^5$ is

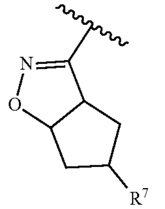
or
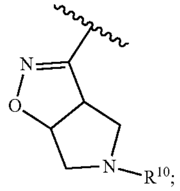
;

$R^7$ is $C_{1-4}$ alkyl substituted with 0-1 $R^9$; $R^9$ is —OH, $R^{10}$ is —C(=O)$R^b$; $R^b$ is H or $C_{1-3}$ alkyl substituted with 0-4 $R^e$; $R^e$ is —$(CH_2)_{0-1}OR^f$, and $R^f$ is H or $C_{1-3}$ alkyl.

Unless specified otherwise, these terms have the following meanings.

"Halo" includes fluoro, chloro, bromo, and iodo.

"Alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond. "Alkyl" also includes deuteroalkyl such as $CD_3$.

"Alkenyl" or "alkenylene" is intended to include hydrocarbon chains of either straight or branched configuration having one or more, preferably one to three, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups; such as ethenyl, propenyl, butenyl, pentenyl, and hexenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

"Carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocyclyls include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocyclyl (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge. When the term "carbocyclyl" is used, it is intended to include "aryl," "cycloalkyl," and "spirocycloalkyl." Preferred carbocyclyls, unless otherwise specified, are cyclopropyl, cyclobutyl, cyclopentyl, cyclohexyl, phenyl, and indanyl.

"Cycloalkyl" is intended to mean cyclized alkyl groups, including mono-, bi- or multicyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl.

"Spirocycloalkyl" is intended to mean hydrocarbon bicyclic ring systems with both rings connected through a single atom. The ring can be different in size and nature, or identical in size and nature. Examples include spiropentane, spriohexane, spiroheptane, spirooctane, spirononane, or spirodecane.

"Bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary,* 13th Edition, John Wiley & Sons, Inc., New York (1997).

"Benzyl" is intended to mean a methyl group on which one of the hydrogen atoms is replaced by a phenyl group, wherein said phenyl group may optionally be substituted with 1 to 5 groups, preferably 1 to 3 groups.

"Heterocycle", "heterocyclyl" or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocyclyl may optionally be quaternized. It is preferred that when the total number of S and O atoms in the heterocyclyl exceeds 1, then these heteroatoms are not adjacent to one another. It is preferred that the total number of S and O atoms in the heterocyclyl is not more than 1. Bridged rings are also included in the definition of heterocyclyl. When the term "heterocyclyl" is used, it is intended to include heteroaryl.

Examples of heterocyclyls include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocyclyls.

"Bicyclic heterocyclyl" "bicyclic heterocyclyl" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocyclyl, a 6-membered heterocyclyl or a carbocyclyl (provided the first ring is not benzo when the second ring is a carbocyclyl).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocyclyl exceeds 1, then these heteroatoms are not adjacent to one another. It is preferred that the total number of S and O atoms in the heterocyclyl is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydroquinolinyl, 2,3-dihydrobenzofuranyl, chromanyl, 1,2,3,4-tetrahydroquinoxalinyl, and 1,2,3,4-tetrahydroquinazolinyl.

"Heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The invention includes all tautomeric forms of the compounds, atropisomers and rotational isomers.

All processes used to prepare compounds of the present invention and intermediates made therein are considered to be part of the present invention.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry,* 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

The invention is intended to include all isotopes of atoms occurring in the compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention. Cis- and trans-(or E- and Z—) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

Biological Methods

RXFP1 Cyclic Adenosine Monophosphate (cAMP) Assays. Human embryonic kidney cells 293 (HEK293) cells and HEK293 cells stably expressing human RXFP1, were cultured in MEM medium supplemented with 10% qualified FBS, and 300 μg/ml hygromycin (Life Technologies). Cells were dissociated and suspended in assay buffer. The assay buffer was HBSS buffer (with calcium and magnesium) containing 20 mM HEPES, 0.05% BSA, and 0.5 mM IBMX. Cells (3000 cells per well, except 1500 cell per well for HEK293 cells stably expressing human RXFP1) were added to 384-well Proxiplates (Perkin-Elmer). Cells were immediately treated with test compounds in DMSO (2% final) at final concentrations in the range of 0.010 nM to 50 μM. Cells were incubated for 30 min at room temperature. The level of intracellular cAMP was determined using the HTRF HiRange cAMP assay reagent kit (Cisbio) according to manufacturer's instructions. Solutions of cryptate conjugated anti-cAMP and d2 fluorophore-labelled cAMP were made in a supplied lysis buffer separately. Upon completion of the reaction, the cells were lysed with equal volume of the d2-cAMP solution and anti-cAMP solution. After a 1 h room temperature incubation, time-resolved fluorescence intensity was measured using the Envision (Perkin-Elmer) at 400 nm excitation and dual emission at 590 nm and 665 nm. A calibration curve was constructed with an external cAMP standard at concentrations ranging from 2.7 μM to 0.1 μM by plotting the fluorescent intensity ratio from 665 nm emission to the intensity from the 590 nm emission against cAMP concentrations. The potency and activity of a compound to inhibit cAMP production was then determined by fitting to a 4-parametric logistic equation from a plot of cAMP level versus compound concentrations.

The examples disclosed below were tested in the human RXFP1 (hRXFP1) HEK293 cAMP assay described above and found to have agonist activity. Tables 1-3, lists $EC_{50}$ values in the hRXFP1 HEK293 cAMP assay measured for the examples.

TABLE 1 lists $EC_{50}$ values in the hRXFP1 HEK293 cAMP assay measured for the naphthalene examples.

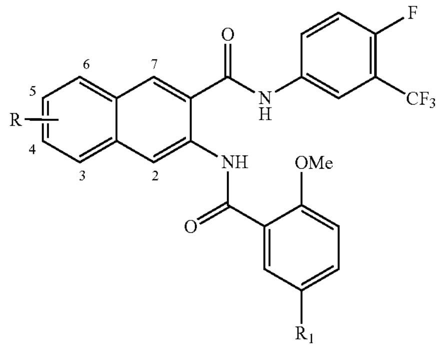

| Example # | Coupling Inter-mediates | R | R1 | hRXFP1 HEK293 cAMP assay $EC_{50}$ nM |
|---|---|---|---|---|
| 1 | 7-1/1-1 | H | 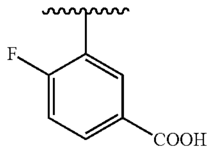 | 1,100 |
| 2 | 7-1/18-1 | H | 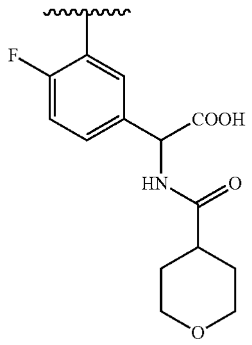 [SMILES: *c1cc(C(NC(=O)C2CCOCC2)C(=O)O)ccc1F] | 4.2 |
| 3 | 17-4/3-6 | 4.5-Br | 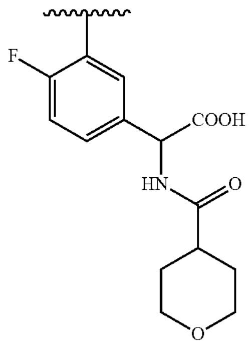 [SMILES: *c1cc(C(NC(=O)C2CCOCC2)C(=O)O)ccc1F] | 190 |

TABLE 1-continued
lists $EC_{50}$ values in the hRXFP1 HEK293 cAMP assay measured for the naphthalene examples.
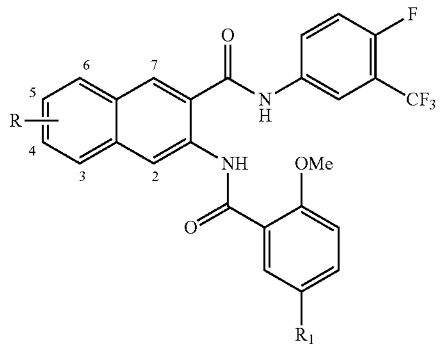
| Example # | Coupling Inter-mediates | R | R1 | hRXFP1 HEK293 cAMP assay $EC_{50}$ nM |
|---|---|---|---|---|
| 4 | 7-1/2-6 | H | 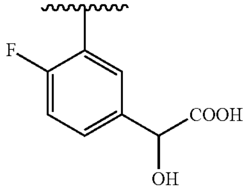 [SMILES: *c1cc(C(O)C(=O)O)ccc1F] | 490 |
| 5 | 7-1/12-3 | H | 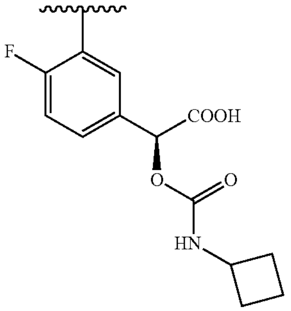 [SMILES: *c1cc([C@H](OC(=O)NC2CCC2)C(=O)O)ccc1F] | 11 |
| 6 | 9-1/1-1 | 3-Br | 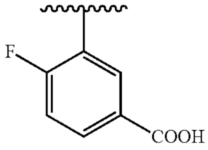 | 1,300 |
| 8 | 13-6/1-1 | 5-Br | 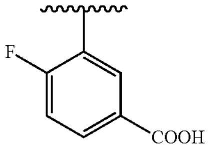 [SMILES: *c1cc(C(=O)O)ccc1F] | 2,600 |
| 9 | 7-1/14-3 | H | 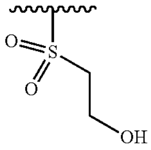 [SMILES: *S(=O)(=O)CCO] | 4,800 |

TABLE 1-continued
lists $EC_{50}$ values in the hRXFP1 HEK293 cAMP assay measured for the naphthalene examples.
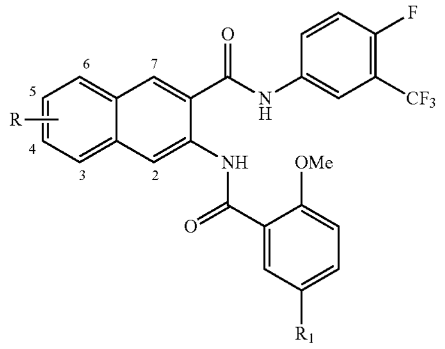
| Example # | Coupling Inter-mediates | R | R1 | hRXFP1 HEK293 cAMP assay $EC_{50}$ nM |
|---|---|---|---|---|
| 10 | 7-1/15-2 | H | 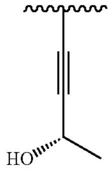 [SMILES: *C#C[C@H](C)O] | 5,000 |
| 11 | 7-1/16-2 | H | 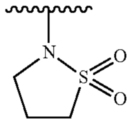 [SMILES: *N1CCCS1(=O)=O] | 2,000 |
| 12 | 7-1/11-2 | H | 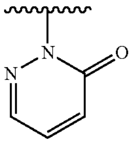 [SMILES: *n1ncccc1=O] | 1,400 |
| 13 | 7-1/6-10 (homo Chiral peak-4) | H | 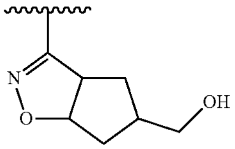 [SMILES: *C1=NOC2CC(CO)CC12] | 320 |
| 14 | 7-1/6-8 (homo Chiral peak-3) | H | 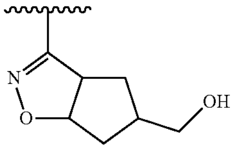 [SMILES: *C1=NOC2CC(CO)CC12] | 60 |
| 15 | 7-1/6-10 | H | 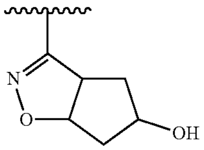 [SMILES: *C1=NOC2CC(O)CC12] | 190 |

Pharmaceutical Compositions and Methods of Use

The compounds of Formula (I) are RXFP1 receptor agonists and may find use in the treatment of medical indications such as heart failure, fibrotic diseases, and related diseases such as lung disease (e.g., idiopathic pulmonary fibrosis), kidney disease (e.g., chronic kidney disease), or hepatic disease (e.g., non-alcoholic steatohepatitis and portal hypertension).

Another aspect of the invention is a pharmaceutical composition comprising a compound of Formula (I) and a pharmaceutically acceptable carrier.

Another aspect of the invention is a pharmaceutical composition comprising a compound of Formula (I) for the treatment of a relaxin-associated disorder and a pharmaceutically acceptable carrier.

Another aspect of the invention is a method of treating a disease associated with relaxin comprising administering an effective amount of a compound of Formula (I).

Another aspect of the invention is a method of treating a cardiovascular disease comprising administering an effective amount of a compound of Formula (I) to a patient in need thereof.

Another aspect of the invention is a method of treating heart failure comprising administering an effective amount of a compound of Formula (I) to a patient in need thereof.

Another aspect of the invention is a method of treating fibrosis comprising administering a therapeutically effective amount of a compound of Formula (I) to a patient in need thereof.

Another aspect of the invention is a method of treating a disease associated with fibrosis comprising administering a therapeutically effective amount of a compound of Formula (I) to a patient in need thereof.

Another aspect of the invention is a method of treating or preventing kidney failure, comprising administering a therapeutically effective amount of a compound of Formula (I) to a patient in need thereof.

Another aspect of the invention is a method of improving, stabilizing or restoring renal function in a patient in need thereof, comprising administering a therapeutically effective amount of a compound of Formula (I) to the patient.

Unless otherwise specified, the following terms have the stated meanings.

The term "patient" or "subject" refers to any human or non-human organism that could potentially benefit from treatment with a RXFP1 agonist as understood by practitioners in this field. Exemplary subjects include human beings of any age with risk factors for cardiovascular disease. Common risk factors include, but are not limited to, age, sex, weight, family history, sleep apnea, alcohol or tobacco use, physical inactivity, arrhythmia, or signs of insulin resistance such as acanthosis nigricans, hypertension, dyslipidemia, or polycystic ovary syndrome (PCOS).

"Treating" or "treatment" cover the treatment of a disease-state as understood by practitioners in this field and include the following: (a) inhibiting the disease-state, i.e., arresting it development; (b) relieving the disease-state, i.e., causing regression of the disease state, and/or (c) preventing the disease-state from occurring in a mammal, in particular, when such mammal is predisposed to the disease-state but has not yet been diagnosed as having it.

"Preventing" or "prevention" cover the preventive treatment (i.e., prophylaxis and/or risk reduction) of a subclinical disease-state aimed at reducing the probability of the occurrence of a clinical disease-state as understood by practitioners in this field. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state. "Risk reduction" or "reducing risk" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination with other agents to treat disorders as understood by practitioners in this field. When applied to a combination, the term refers to combined amounts of the active ingredients that result in the preventive or therapeutic effect, whether administered in combination, serially, or simultaneously.

"Disorders of the cardiovascular system" or "cardiovascular disorders" include for example the following disorders: hypertension (high blood pressure), peripheral and cardiac vascular disorders, coronary heart disease, stable and unstable angina pectoris, heart attack, myocardial insufficiency, abnormal heart rhythms (or arrhythmias), persistent ischemic dysfunction ("hibernating myocardium"), temporary postischemic dysfunction ("stunned myocardium"), heart failure, disturbances of peripheral blood flow, acute coronary syndrome, heart failure, heart muscle disease (cardiomyopathy), myocardial infarction and vascular disease (blood vessel disease).

"Heart failure" includes both acute and chronic manifestations of heart failure, as well as more specific or related types of disease, such as advanced heart failure, post-acute heart failure, cardio-renal syndrome, heart failure with impaired kidney function, chronic heart failure, chronic heart failure with mid-range ejection fraction (HFmEF), compensated heart failure, decompensated heart failure, right heart failure, left heart failure, global failure, ischemic cardiomyopathy, dilated cardiomyopathy, heart failure associated with congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, systolic heart failure, acute phases of worsening heart failure, heart failure with preserved ejection fraction (HFpEF), heart failure with reduced ejection fraction (HFrEF), chronic heart failure with reduced ejection fraction (HFrEF), chronic heart failure with preserved ejection fraction (HFpEF), post myocardial remodeling, angina, hypertension, pulmonary hypertension and pulmonary artery hypertension.

"Fibrotic disorders" encompasses diseases and disorders characterized by fibrosis, including among others the following diseases and disorders: hepatic fibrosis, cirrhosis of the liver, NASH, pulmonary fibrosis or lung fibrosis, cardiac fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitreoretinopathy and disorders of the connective tissue (for example sarcoidosis).

Relaxin-associated disorders include but are not limited to disorders of the cardiovascular system and fibrotic disorders.

The compounds of this invention can be administered by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

"Pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition. A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule. A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The compounds may be employed in combination with other suitable therapeutic agents useful in the treatment of diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The additional therapeutic agents may include ACE inhibitors, β-blockers, diuretics, mineralocorticoid receptor antagonists, ryanodine receptor modulators, SERCA2a activators, renin inhibitors, calcium channel blockers, adenosine A1 receptor agonists, partial adenosine A1 receptor, dopamine β-hydroxylase inhibitors, angiotensin II receptor antagonists, angiotensin II receptor antagonists with biased agonism for select cell signaling pathways, combinations of angiotensin II receptor antagonists and neprilysin enzyme inhibitors, neprilysin enzyme inhibitors, soluble guanylate cyclase activators, myosin ATPase activators, rho-kinase 1 inhibitors, rho-kinase 2 inhibitors, apelin receptor agonists, nitroxyl donating compounds, calcium-dependent kinase II inhibitors, antifibrotic agents, galectin-3 inhibitors, vasopressin receptor antagonists, FPR2 receptor modulators, natriuretic peptide receptor agonists, transient receptor potential vanilloid-4 channel blockers, anti-arrhythmic agents. $I_f$ "funny current" channel blockers, nitrates, digitalis compounds, inotropic agents and β-receptor agonists, cell membrane rescaling agents for example Poloxamer 188, anti-hyperlipidemic agents, plasma HDL-raising agents, anti-hypercholesterolemic agents, cholesterol biosynthesis inhibitors (such as HMG CoA reductase inhibitors), LXR agonist, FXR agonist, probucol, raloxifene, nicotinic acid, niacinamide, cholesterol absorption inhibitors, bile acid sequestrants, anion exchange resins, quaternary amines, cholestyramine, colestipol, low density lipoprotein receptor inducers, clofibrate, fenofibrate, bezafibrate, ciprofibrate, gemfibrizol, vitamin B6, vitamin B12, anti-oxidant vitamins, anti-diabetes agents, platelet aggregation inhibitors, fibrinogen receptor antagonists, aspirin and fibric acid derivatives, PCSK9 inhibitors, aspirin, and P2Y12 Inhibitors such as Clopidogrel.

The additional therapeutic agents may also include nintedanib, Pirfenidone, LPA1 antagonists, LPA1 receptor antagonists, GLP1 analogs, tralokinumab (IL-13, AstraZeneca), vismodegib (hedgehog antagonist, Roche), PRM-151 (pentraxin-2, TGF beta-1, Promedior), SAR-156597 (bispecific Mab IL-4&IL-13, Sanofi), simtuzumab ((anti-lysyl oxidase-like 2 (anti-LOXL2) antibody, Gilead), CKD-942, PTL-202 (PDE inh./pentoxifylline/NAC oral control, release, Pacific Ther.), omipalisib (oral PI3K/mTOR inhibitor, GSK), IW-001 (oral sol, bovine type V collagen mod., ImmuneWorks), STX-100 (integrin alpha V/beta-6 ant, Stromedix/Biogen), Actimmune (IFN gamma). PC-SOD (midismase; inhaled, LTT Bio-Pharma/CKD Pharm), lebrikizumab (anti-IL-13 SC humanized mAb, Roche), AQX-1125 (SHIP1 activator, Aquinox), CC-539 (JNK inhibitor, Celgene), FG-3019 (FibroGen), SAR-100842 (Sanofi), and obeticholic acid (OCA or INT-747, Intercept).

The above other therapeutic agents, when employed in combination with the compounds of the present invention may be used, for example, in those amounts indicated in the Physicians' Desk Reference, as in the patents set out above, or as otherwise determined by practitioners in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

The compounds of the present invention are also useful as standard or reference compounds, for example as a quality standard or control, in tests or assays involving RXFP1. Such compounds may be provided in a commercial kit, for example, for use in pharmaceutical research involving RXFP1. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving RXFP1.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Synthesis Schemes

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

Naphthalene compounds of this invention can be accessed from commercially available methyl 3-amino-2-naphthoate or can be accessed via that shown in scheme-1.

Scheme-1

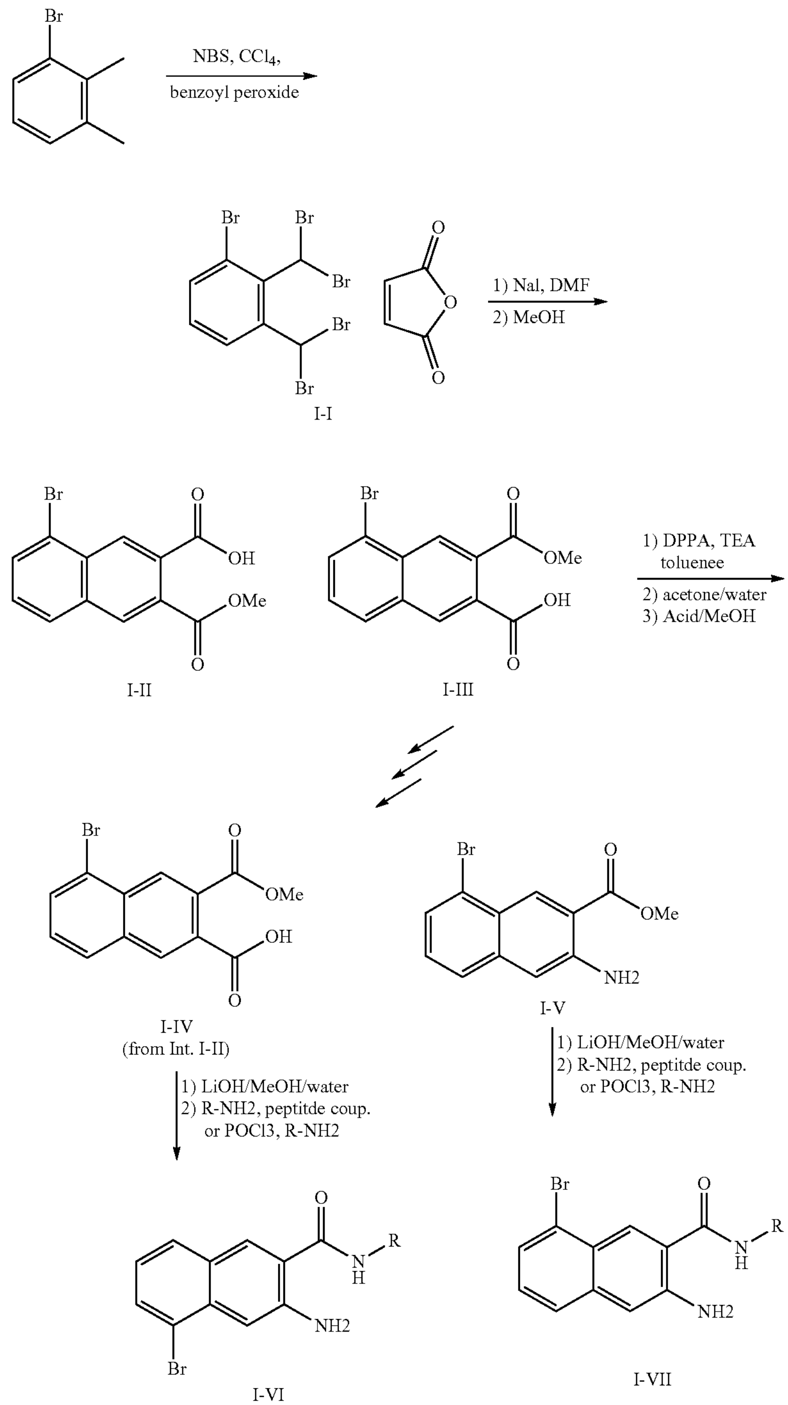

I-I

I-II

I-III

I-IV (from Int. I-II)

I-V

I-VI

I-VII

Commercially available 2,3-dimethylbromobenzene, was poly-brominated with NBS to provide intermediate I-I. Condensation of I-I with succinimide in the presence of NaI in DMF afforded 5-bromonaphtho[2,3-c]furan-1,3-dione, which on treatment with methanol provided a mixture of bromonaphthalene derivative I-II and I-III which were separated via known separation techniques. Curtius reaction of I-II followed by conversion of the ensuing isocyanate provided intermediate amine I-IV. The bromo moiety was converted to other compounds of this invention (e.g. via Suzuki coupling, photoredox, alkylations, esterification, amides, sulfonamides etc.). Alternatively I-II were de-brominated to provide the unsubstituted naphthalene derivatives. Intermediate I-III can also be converted under the same conditions to intermediate I-V. Both intermediates I-IV and I-V can be converted to amides of this invention I-VI and I-VII by coupling with an appropriate amine or aniline.

Quinoline analogs of this invention were also be prepared in a similar manner (scheme-2).

Scheme-2

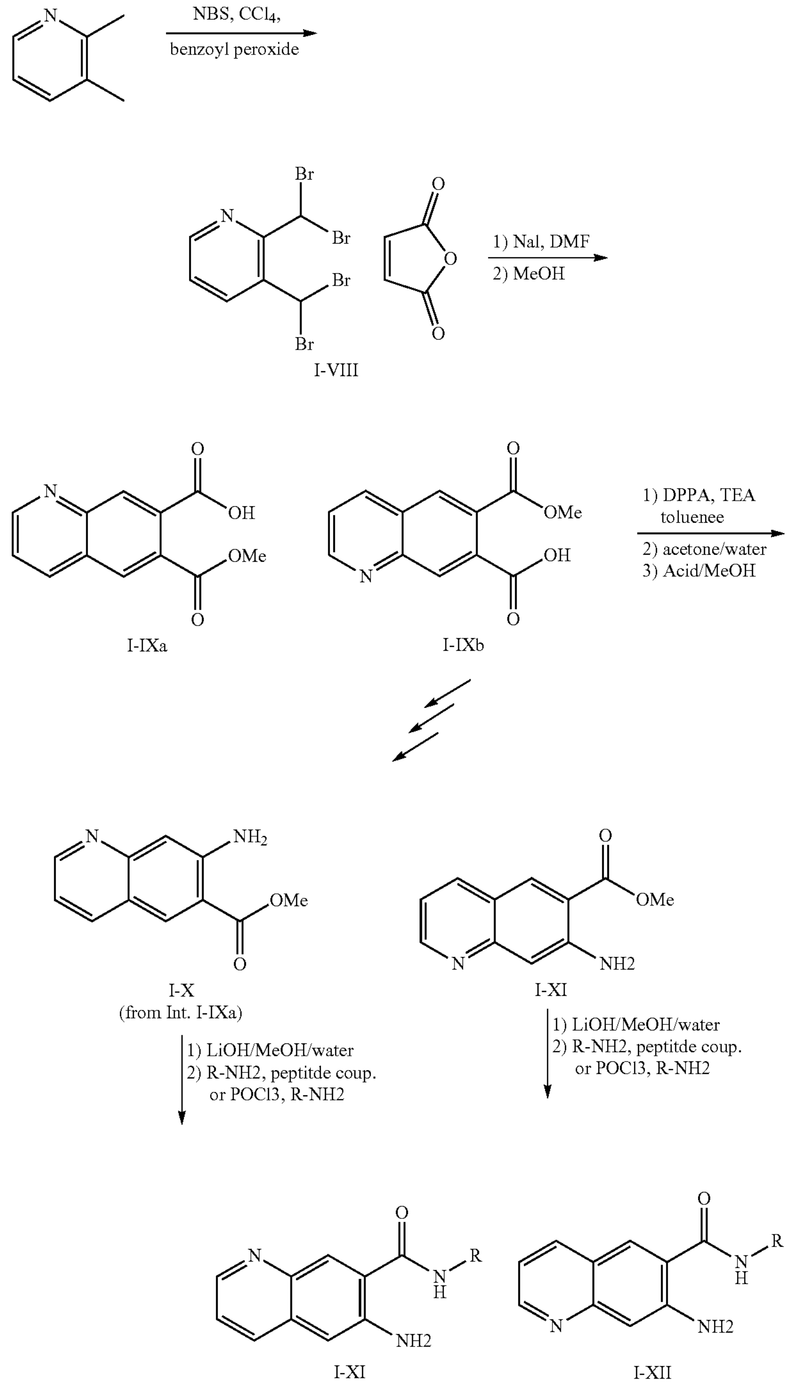

I-VIII

I-IXa

I-IXb

I-X
(from Int. I-IXa)

I-XI

I-XI

I-XII

Alternatively, quinolines were accessed via the general method outlined in scheme-3.

Scheme-3

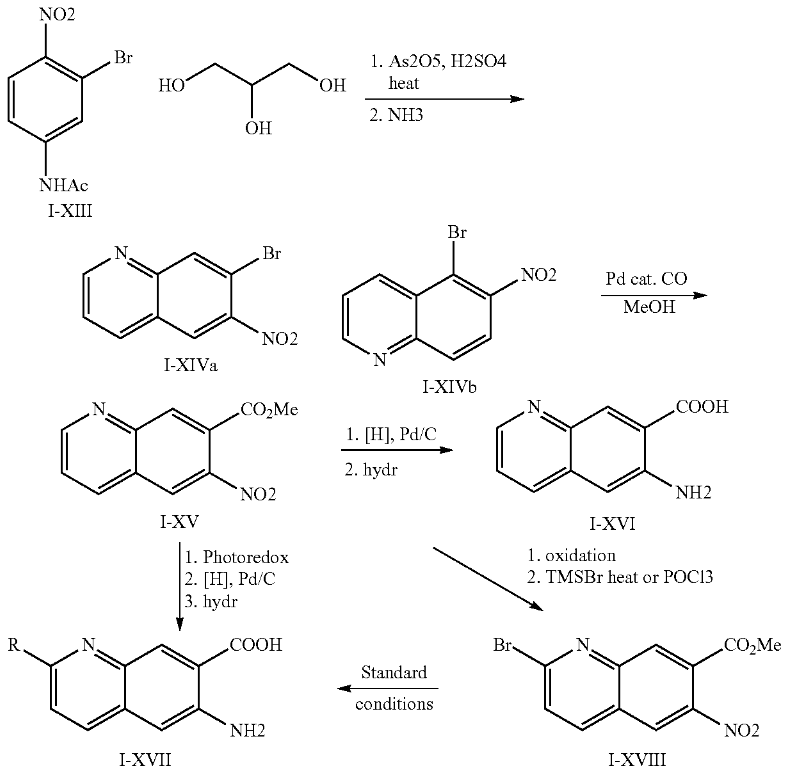

Conversion of intermediate I-XV and or I-XVIII to the requisite quinolines e.g. I-XVII were accomplished under photoredox conditions or via conversion to the bromoquinolines via the method outlined or known in the art, followed by standard alkylations, carbonylations, amidations and Suziki couplings. Intermediate I-XVII was then converted to compounds of this invention as outlined in Scheme-1.

Chemical Methods

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene, T. W. et al., Protecting Groups in Organic Synthesis, 4th Edition, Wiley (2007)).

Abbreviations are defined as follows: "1×" for once, "2×" for twice, "3×" for thrice, "° C." for degrees Celsius, "aq" for aqueous, "eq" or "equiv." for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "pM" for picomolar, "mol" for mole or moles, "mmol" for millimole or millimoles. "min" for minute or minutes, "h" for hour or hours, "rt" for room temperature, "RT" for retention time, "atm" for atmosphere, "psi" for pounds per square inch, "conc." for concentrate, "aq" for "aqueous", "sat." for saturated, "MW" for molecular weight. "MS" or "Mass Spec" for mass spectrometry. "ESI" for electrospray ionization mass spectroscopy, "LC-MS" for liquid chromatography mass spectrometry, "HPLC" for high pressure liquid chromatography, "RP HPLC" for reverse phase HPLC, "NMR" for nuclear magnetic resonance spectroscopy, "SFC" for super critical fluid chromatography. "1H" for proton. "δ" for delta, "s" for singlet, "d" for doublet, "t" for triplet, "q" for quartet, "m" for multiplet, "br" for broad, "Hz" for hertz, "MHz" for megahertz, and "α", "β", "R", "S", "E", and "Z" are stereochemical designations familiar to one skilled in the art.

| | |
|---|---|
| AcCl | acetyl chloride |
| AcOH | acetic acid |
| AIBN | Azobisisobutyronitrile |
| BHFFT | bis(tetramethylene)fluoroformadmidinium hexafluorophosphate |
| Boc | tert-butyloxycarbonyl |
| BuLi | butyl lithium |
| DAST | Diethylaminosulfur trifluoroide |
| DCE | Dichloroethane |
| DCM | Dichloromethane |
| DIEA | diispropyl ethylamine |
| DMAP | 4-dimethylamino pyridine |
| DMF | Dimethylformamide |
| DPPA | Diphenyl phosphorylazide |
| $Et_2O$ | diethyl ether |
| EtOAc | Ethyl acetate |
| EtOH | Ethanol |
| HATU | (1-[Bis(dimethylamino)methylene]-1H-1,2,3-triazolo[4,5-b]pyridinium 3-oxid hexafluorophosphate) |
| HMPA | hexamethylphosphoramide |
| IPA | isopropanol |

-continued

| | |
|---|---|
| i-Pr | Isopropyl |
| KHMDS | potassium bis(trimethylsilyl)amide |
| LDA | lithium diisopropyl amide |
| MeCN | Acetonitrile |
| MeOH | Methanol |
| Me | Methyl |
| NBS | N-bromosuccinimide |
| Pd/C | palladium on carbon |
| pTsOH | p-toluenesulfonic acid |
| PyBroP | Bromotripyrrolidinophosphonium hexafluorophosphate |
| T3P | 2,4,6-Tripropyl-1,3,5,2,4,6-trioxatriphosphorinane-2,4,6-trioxide |
| TBAF | tetra-n-butyl ammonium fluoride |
| TCFH | N-(chloro(dimethylamino)methylene)-N-methylmethanaminium hexafluorophosphate(V) |
| t-Bu | tert-butyl |
| Teoc | 2-(trimethylsilyl)ethyl carboxylate |
| TFA | trifluoro acetic acid |
| TFAA | trifluoro acetic anhydride |
| THF | Tetrahydrofuran |
| TsOH | Tolulenesulfonic acid |
| XPhos-Pd-G2 | 2nd generation XPhos precatalyst CAS no. 1310584-14-5 |

The following methods were used in the exemplified examples, except where noted otherwise. Purification of intermediates and final products was carried out via either normal or reverse phase chromatography. Normal phase chromatography was carried out using prepacked SiO2 cartridges eluting with either gradients of hexanes and ethyl acetate or DCM and MeOH unless otherwise indicated. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (95% water, 5% ACN, 0.1% TFA) and Solvent B (5% water, 95% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM $NH_4OAc$) and Solvent B (98% ACN, 2% water, 10 mM $NH_4OAc$) or with gradients of Solvent A (98% water, 2% ACN, 0.1% $NH_4OH$) and Solvent B (98% ACN, 2% water, 0.1% $NH_4OH$). LC/MS methods employed in characterization of examples are listed below.

Method A:
- Instrument: Waters Acquity coupled with a Waters MICROMASS® ZQ Mass Spectrometer
- Linear gradient of 2 to 98% B over 1 min, with 0.5 min hold time at 98% B
- UV visualization at 220 nm
- Column: Waters BEH C18, 2.1×50 mm
- Flow rate: 0.8 mL/min (Method A)
- Mobile Phase A: 0.05% TFA, 100% water
- Mobile Phase B: 0.05% TFA, 100% acetonitrile Method B:
- Instrument: Shimadzu Prominence HPLC coupled with a Shimadzu LCMS-2020 Mass Spectrometer
- Linear gradient of 0 to 100% B over 3 min, with 0.75 min hold time at 100% B
- UV visualization at 220 nm
- Column: Waters Xbridge C18, 2.1×50 mm, 1.7 um particles
- Flow rate: 1 mL/min
- Mobile Phase A: 10 mM ammonium acetate, 95:5 water:acetonitrile
- Mobile Phase B: 10 mM ammonium acetate, 5:95 water:acetonitrile Method C:
- Instrument: Shimadzu Prominence HPLC coupled with a Shimadzu LCMS-2020 Mass Spectrometer
- Linear gradient of 0 to 100% B over 3 min, with 0.75 min hold time at 100% B
- UV visualization at 220 nm
- Column: Waters Xbridge C18, 2.1×50 mm, 1.7 um particles
- Flow rate: 1 mL/min
- Mobile Phase A: 0.1% TFA, 95:5 water:acetonitrile
- Mobile Phase B: 0.1% TFA, 5:95 water:acetonitrile Method D:
- Instrument: Waters Acquity coupled with a Waters MICROMASS® ZQ Mass Spectrometer
- Linear gradient of 10% B to 98% B over 1 min, with 0.5 min hold time at 98% B
- UV visualization at 220 nm
- Column: Waters Acquity GEN C18, 2.1×50 mm, 1.7 um particles
- Flow rate: 1 ml/min
- Mobile Phase A: 0.05% TFA, 100% water
- Mobile Phase B: 0.05% TFA, 100% acetonitrile NMR Employed in Characterization of Examples. $^1H$ NMR spectra were obtained with Bruker or JEOL® Fourier transform spectrometers operating at frequencies as follows:

1H NMR: 400 MHz (Bruker or JEOL®) or 500 MHz (Bruker or JEOL®). Spectra data are reported in the format: chemical shift (multiplicity, coupling constants, number of hydrogens). Chemical shifts are specified in ppm downfield of a tetramethylsilane internal standard (d units, tetramethylsilane=0 ppm) and/or referenced to solvent peaks, which in $^1H$ NMR spectra appear at 2.51 ppm for DMSO-d6, 3.30 ppm for $CD_3OD$, 1.94 ppm for $CD_3CN$, and 7.24 ppm for $CDCl_3$.

Preparation of Intermediates

Intermediate 1-1: 5'-(tert-butoxycarbonyl)-2'-fluoro-4-methoxy-[1,1'-biphenyl]-3-carboxylic acid Int. 1-1

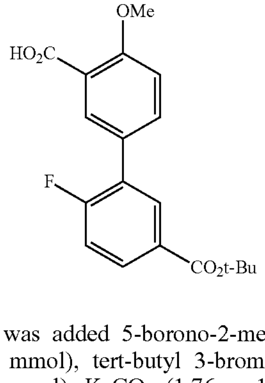

To a vial was added 5-borono-2-methoxybenzoic acid (0.50 g, 2.6 mmol), tert-butyl 3-bromo-4-fluorobenzoate (0.84 g, 3.1 mmol), $K_2CO_3$ (1.76 g, 12.8 mmol). $PdCl_2$(dppf)-$CH_2Cl_2$ adduct (0.31 g, 0.38 mmol), and THF (22 mL). The reaction mixture was degassed for 2 min with nitrogen, then heated at 80° C. for 18 h. After allowing to cool to rt, the reaction mixture was diluted with 1N HCl (25 mL) and the solution extracted with EtOAc (3×25 mL). The combined organic portions were dried over $Na_2SO_4$, filtered, concentrated under reduced pressure, and the resulting residue was dissolved in DMF and purified by preparative RP-HPLC to afford intermediate 1-1 (586 mg, 66.0% yield). LC-MS RT=1.02 min; MS (ESI) m/z $(M+H)^+$=347.1; [Method A].

Intermediate 2-6: 5'-(2-(tert-butoxy)-1-hydroxy-2-oxoethyl)-2'-fluoro-4-methoxy-[1,1'-biphenyl]-3-carboxylic acid. Intermediate 2-6 was prepared following the method outlined in the scheme below.

Int. 2-6

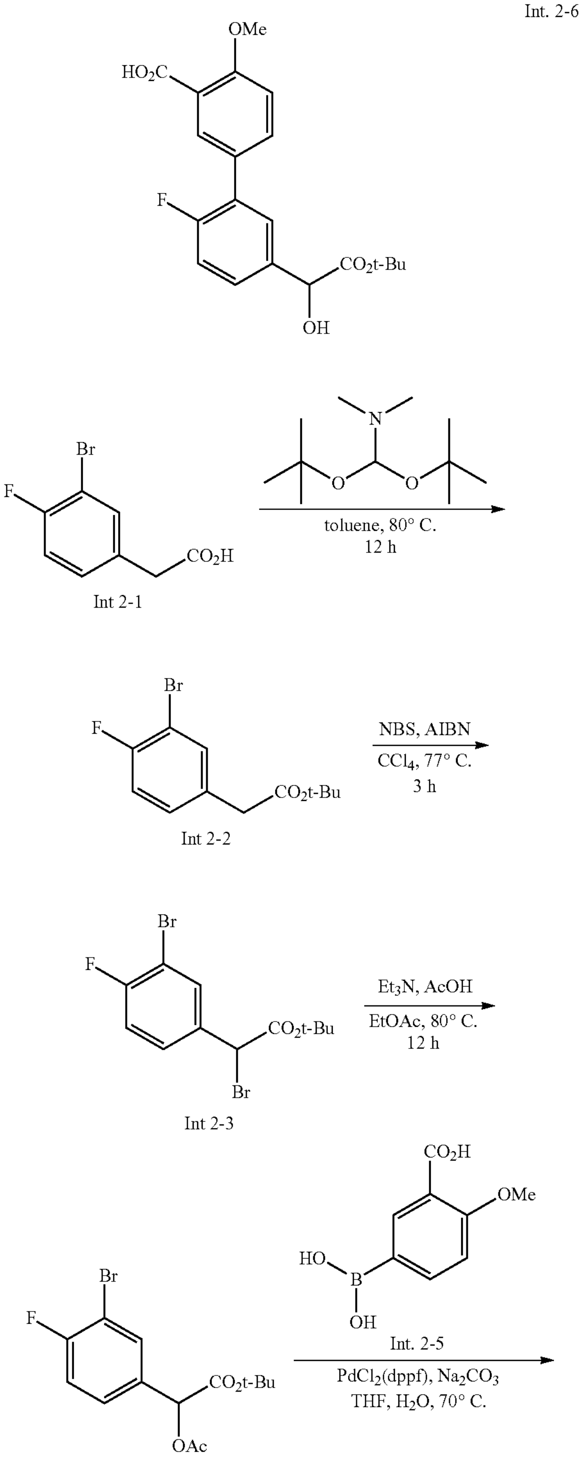

Int 2-1

Int 2-2

Int 2-3

Int 2-4

-continued

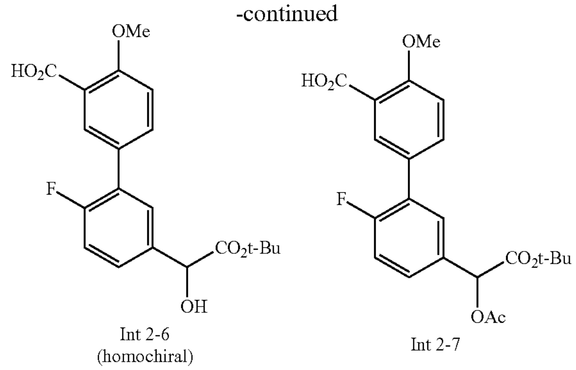

Int 2-6 (homochiral)

Int 2-7

Intermediate 2-2: Intermediate 2-2 was prepared employing known conditions for analogous substrates (Ludwig, J., Lehr, M. *Syn. Comm.* 2004, 34, 3691-3695), except the reaction temperature was maintained at 80° C. for 12 h. $^1$H NMR (500 MHz, $CDCl_3$) δ 7.49 (dd, J=6.6, 2.2 Hz, 1H), 7.20 (ddd, J=8.3, 4.6, 2.2 Hz, 1H), 7.13-7.03 (m, 1H), 3.49 (s, 2H), 1.46 (s, 9H).

Intermediate 2-3: To a 20 mL reaction vial charged with intermediate 2-2 (0.27 g, 0.92 mmol) was added NBS (0.20 g, 1.1 mmol), $CCl_4$ (10 mL), and AIBN (15 mg, 0.090 mmol). The solution was stirred at 77° C., for 3 h. The solution was concentrated under reduced pressure and purified by normal phase silica gel chromatography to give intermediate 2-3 (310 mg, 0.84 mmol, 91% yield). $^1$H NMR (500 MHz, $CDCl_3$) δ 7.79 (dd, J=6.5, 2.3 Hz, 1H), 7.55-7.46 (m, 1H), 7.18-7.10 (m, 1H), 5.18 (s, 1H), 1.50 (s, 9H).

Intermediate 2-4: To a 2 dram vial charged with intermediate 2-3 was added EtOAc (2 mL), TEA (0.27 mL, 2.0 mmol), and acetic acid (0.1 mL, 2 mmol). The reaction mixture was stirred at 80° C. for 12 h. The reaction mixture was concentrated under reduced pressure and purified by normal phase silica gel chromatography to give intermediate 2-4 which was used without further purification. $^1$H NMR (500 MHz, $CDCl_3$) δ 7.70 (dd, J=6.6, 2.2 Hz, 1H), 7.41 (ddd, J=8.4, 4.7, 2.1 Hz, 1H), 7.15 (t, J=8.4 Hz, 1H), 5.77 (s, 1H), 2.22 (s, 3H), 1.43 (s, 9H).

Intermediate 2-6: Intermediate 2-6 was prepared from intermediate 2-4, employing 5-borono-2-methoxybenzoic acid 2-5 using similar conditions to those described for intermediate 1-1. After reverse phase HPLC using Phenomenex Luna C18 5 u 30×100 mm column, 10-minute gradient; Solvent A: 10% ACN-90% $H_2O$-0.1% TFA; Solvent B: 90% ACN-10% $H_2O$-0.1% TFA, half of the material was isolated as intermediate 2-7 (85 mg, 0.60 mmol, 34% yield); $^1$H NMR (500 MHz, $CDCl_3$) δ 8.43-8.36 (m, 1H), 7.81 (dt, J=8.7, 2.0 Hz, 1H), 7.56 (dd. J=7.3, 2.3 Hz, 1H), 7.45 (ddd, J=8.5, 4.6, 2.3 Hz, 1H), 7.23-7.16 (m, 2H), 5.84 (s, 1H), 4.17 (s, 3H), 2.23 (s, 3H), 1.45 (s, 9H) while the other half was isolated as the alcohol intermediate 2-6 (70 mg, 0.19 mmol, 31% yield); $^1$H NMR (500 MHz, $CDCl_3$) δ 8.40 (d, J=2.2 Hz, 1H), 7.82 (dt, J=8.6, 2.2 Hz, 1H), 7.54 (dd, J=7.4, 2.5 Hz, 1H), 7.41 (ddd, J=8.4, 4.8, 2.2 Hz, 1H), 7.19-7.14 (m, 2H), 5.09 (s, 1H), 4.16 (s, 3H), 1.47 (s, 9H). Intermediate 2-6 was separated into individual enantiomers using chiral SFC. Preparative chromatographic conditions: Instrument: Berger MG II; Column: Chiralpak ID, 21×250 mm, 5 micron; Mobile phase: 25% IPA/75% $CO_2$; Flow conditions; 45 mL/min, 120 Bar, 40° C.; Detector wavelength: 220 nm; Injection details: 8 injections of 0.36 mL of ~20 mg/mL in IPA. Analytical chromatographic conditions: Instrument: Waters UPC2 analytical SFC; Column: Chiralpak ID 4.6×

100 mm, 3 micron: Mobile phase: 25% IPA/75% $CO_2$: Flow conditions: 2 mL/min, 150 Bar, 40° C.; Detector wavelength: 220 nm. Peak 1, RT=3.89 min, >99.5% ee; Peak 2, RT=5.44 min, >99.5% ee. as intermediate 2-6.

Intermediate 3-2: 5'-(2-(tert-butoxy)-1-((tert-butoxycarbonyl)amino)-2-oxoethyl)-2'-fluoro-4-methoxy-[1,1'-biphenyl]-3-carboxylic acid. The titled compound was prepared following the method outlined in the scheme below.

Int. 3-2 & Int. 3-3

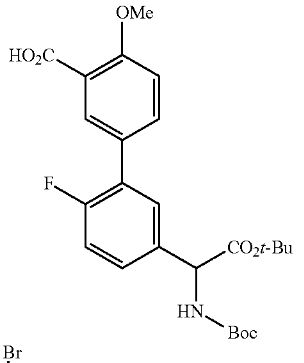

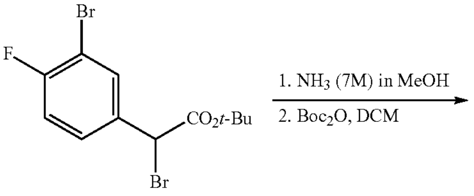

Int. 2-3

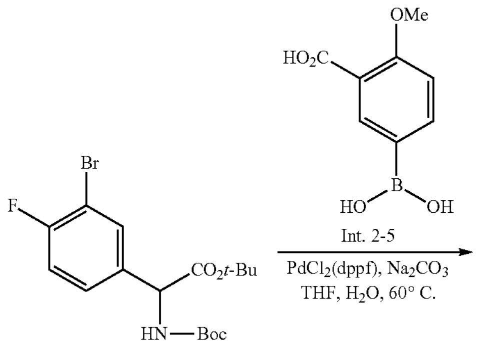

Int. 3-1

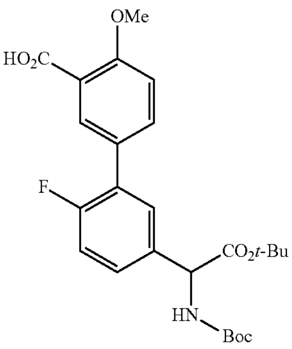

Int. 3-2 (peak 1)
Int. 3-3 (peak 2)

Intermediate 3-1: To 2-3 (60 mg, 0.16 mmol) was added ammonia (0.5 mL, 3.5 mmol, in MeOH). After stirring at rt for 12 h, the mixture was concentrated under vacuum. To the amine in DCM (I mL) was added BOC-anhydride (0.11 mL, 0.49 mmol) and DIEA (57 μL, 0.33 mmol) and the reaction mixture was stirred at rt for 1 h. The mixture was concentrated under vacuum and silica gel chromatography purification produced 3-1 (42 mg, 0.1 mmol, 63% yield). LC-MS: RT=1.14 min; MS (ESI) m/z=406.0 $(M+H)^+$ [Method A].

Intermediates 3-2 and 3-3: Intermediates 3-2 and 3-3 were prepared employing that similar Suzuki cross coupling conditions that were used for intermediate 1-1, except at a temperature of 60° C. for 18 h. After allowing to cool to rt, the reaction mixture was diluted with 1N HCl (25 mL) and the solution extracted with EtOAc (3×25 mL). The combined organic portions were dried over $Na_2SO_4$, filtered, concentrated under reduced pressure, and purified by preparative RP-HPLC. $^1$H NMR (500 MHz, $CDCl_3$) δ 8.38 (d, J=1.9 Hz, 1H), 7.80 (dt, J=8.7, 2.0 Hz, 1H), 7.46 (dd, J=7.4, 2.5 Hz, 1H), 7.36 (dddd, J=8.8, 4.4, 2.2, 1.1 Hz, 1H), 7.19-7.13 (m, 2H), 5.67 (br d, J=5.2 Hz, 1H), 5.25 (br d, J=6.3 Hz, 1H), 4.16 (s, 3H), 1.46 (br s, 9H), 1.44 (s, 9H). The residue was separated into individual enantiomers using chiral SFC. Preparative chromatographic conditions: Instrument: Berger MG II; Column: Chiralpak ID, 21×250 mm, 5 micron; Mobile phase: 20% MeOH/80% $CO_2$: Flow conditions: 45 mL/min, 120 Bar, 40° C.; Detector wavelength: 209 nm; Injection details: 49 injections in MeOH. Analytical chromatographic conditions: Instrument: Waters UPC2 analytical SFC; Column: Chiralpak IC, 4.6×100 mm, 3 micron; Mobile phase: 25% MeOH/75% $CO_2$; Flow conditions: 2 mL/min, 150 Bar, 40° C.; Detector wavelength: 220 nm. 3-2, Peak 1, RT=4.22 min, 95.7% ee; 3-3. Peak 2, RT=5.11 min, >99% ee.

Intermediate 4-4: 2'-fluoro-4-methoxy-5'-(2,2,2-trifluoro-1-hydroxyethyl)-[1,1'-biphenyl]-3-carboxylic acid. The titled compound was prepared following the scheme outlined below.

Int. 4-4

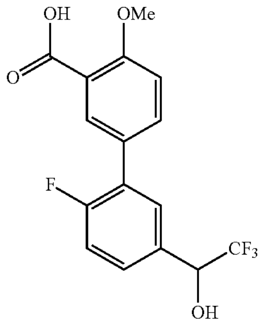

(homochiral)

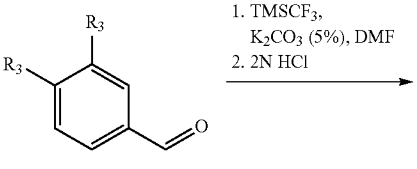

Int. 4-1

-continued

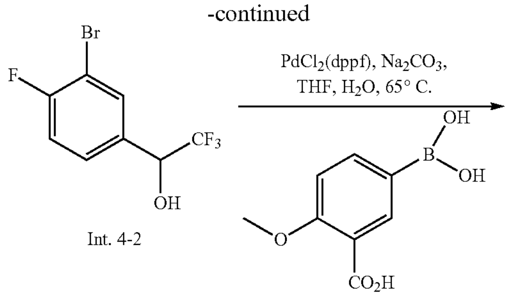

Int. 4-2

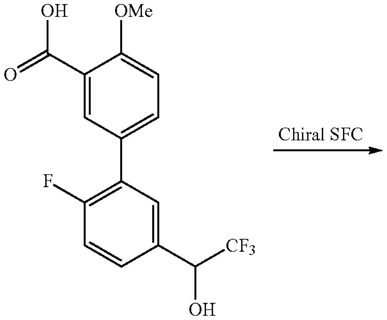

Int. 4-3

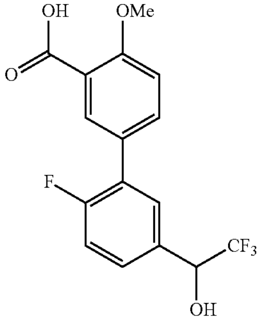

Int. 4-4
(homochiral)

Intermediate 4-2: Into the reaction vessel was added 3-bromo-4-fluorobenzaldehyde (4-1, 235 mg, 1.15 mmol), DMF (3.5 mL), (trifluoromethyl)trimethylsilane (0.34 mL, 2.3 mmol), and $K_2C_{03}$ (8 mg, 0.06 mmol). The reaction mixture was stirred at it for 60 min, the reaction mixture allowed to cool to rt and 2N HCl (3 mL) was added. After stirring at rt for an additional 1 h, the reaction mixture was diluted with EtOAc (15 mL), and the solution washed with sat $NH_4Cl$. The aqueous phase was extracted with EtOAc (2×10 mL). The combined organic portions were dried over $Na_2SO_4$, filtered, concentrated under reduced pressure, and purified by silica gel chromatography (0-35% EtOAc in hexanes) to produce 4-2 (205 mg, 0.75 mmol, 65% yield). $^1H$ NMR (500 MHz, $CDCl_3$) d 7.74 (dd, J=6.5, 2.1 Hz, 1H), 7.43 (ddd, J=8.4, 4.8, 2.2 Hz, 1H), 7.19 (t, J=8.4 Hz, 1H), 5.11-4.98 (m, 1H), 2.69 (d, J=4.4 Hz, 1H).

Intermediate 4-3: Into the reaction vessel containing 4-2 (100 mg, 0.37 mmol) was added 5-borono-2-methoxybenzoic acid (93 mg, 0.48 mmol), $PdCl_2$(dppf)-$CH_2Cl_2$ adduct (50 mg, 0.06 mmol), $Na_2CO_3$ (155 mg, 1.46 mmol), and $H_2O$ (1 mL). The reaction mixture was degassed by bubbling $N_2$ for 10 min, sealed, and stirred at 65° C. for 3 h. After allowing to cool to rt, the reaction mixture was quenched by the addition of 1N HCl, the solution extracted with EtOAc, dried over $Na_2SO_4$, filtered, concentrated under reduced pressure and purified by HPLC to produce 4-3 (51 mg, 0.15 mmol, 40% yield). $^1H$ NMR (500 MHz, $CDCl_3$) δ 8.39 (d, J=1.9 Hz, 1H), 7.83 (dt, J=8.7, 2.1 Hz, 1H), 7.59 (dd, J=7.3, 2.1 Hz, 1H), 7.53-7.45 (m, 1H), 7.23 (dd, J=10.2, 8.8 Hz, 1H), 7.18 (d, J=8.5 Hz, 1H), 5.11 (q, J=6.6 Hz, 1H), 4.17 (s, 3H). MS (EST) m/z=345.1 $(M+H)^+$.

Intermediate 4-4: Intermediate 4-3 was separated into individual enantiomers using chiral SFC. Preparative chromatographic conditions: Instrument: Berger MG II; Column: Kromasil 5-CelluCoat, 21×250 mm, 5 micron: Mobile phase: 15% IPA-ACN (0.1% DEA)/85% $CO_2$: Flow conditions: 45 mL/min, 120 Bar, 40° C.; Detector wavelength: 220 nm; Injection details: 0.4 mL of ~15 mg/mL in ACN-IPA (1:1). Peak 2 was collected to afford intermediate 4-4. Analytical chromatographic conditions: Instrument: Aurora Infinity Analytical SFC; Column: Kromasil 5-CelluCoat, 4.6×250 mm, 5 micron; Mobile phase: 20% IPA-ACN (0.1% DEA)/80% $CO_2$; Flow conditions: 2 mL/min, 150 Bar, 40° C.: Detector wavelength: 220 nm. Peak 1, RT=9.12 min, 99% ee; Peak 2, RT=10.19 min, 98% ee.

Intermediate 5-2: 5-(5-hydroxy-3a,5,6,6a-tetrahydro-4H-cyclopenta[d]isoxazol-3-yl)-2-methoxybenzoic acid. The titled compound was prepared following the scheme outlined below.

Int. 5-2

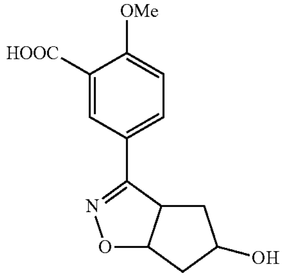

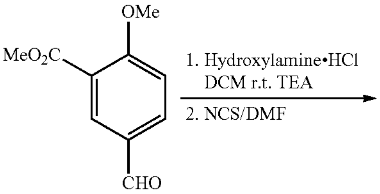

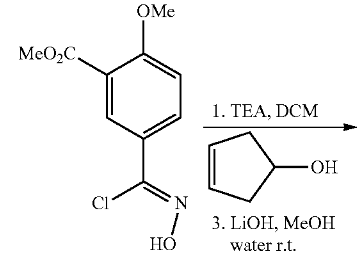

Int. 5-1

-continued

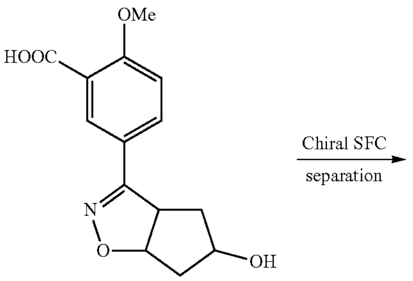

Int. 5-2
Diasteromeric
mixture

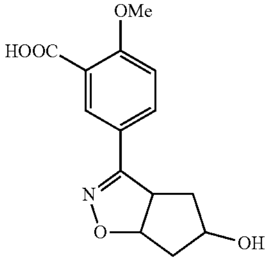

Int. 5-3
Homochiral Peak-1

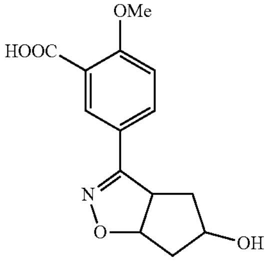

Int. 5-4
Homochiral Peak-2

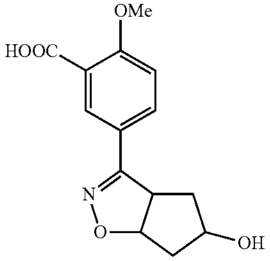

Int. 5-5
Homochiral Peak-3

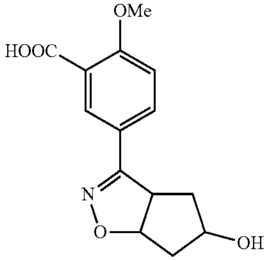

Int. 5-6
Homochiral peak-4

Intermediate 5-1. Methyl 5-formyl-2-methoxybenzoate (24.9 g, 128 mmol) was dissolved in DCM (500 mL). To the solution was added triethyamine (17.9 mL, 128 mmol) followed by hydroxylamine hydrochloride (8.91 g, 128 mmol). The reaction mixture was stirred for 14 h at rt and concentrated under reduced pressure to yield a white solid. The solid was dissolved in water (200 mL) and the aqueous portion extracted with EtOAc (2×100 mL). The combined organic portion was, dried ($MgSO_4$), filtered and concentrated under reduced pressure to yield a white solid (27.1 g, 100% yield). The solid was re-dissolved in DMF (200 mL) and to the solution was added NCS (17.2 g, 128 mmol) and stirred at rt for 14 h. The reaction mixture was quenched by the addition of excess water and a white solid precipitated. The solid was separated by filtration and washed with excess water and dried under vacuum to afford a white solid (287 g, 89% yield) for intermediate 5-1. $^1$H NMR (500 MHz, $CDCl_3$) δ 8.32-8.30 (m, 1H), 7.99-7.96 (m, 1H), 7.80-7.78 (m, 1H), 7.05-7.02 (d, 1H), 3.98 (s, 3H), 3.94 (s, 3H).

Intermediate 5-2 (diastereomeric mixture): Alternatively, (E)-5-((hydroxyimino)methyl)-2-methoxybenzoic acid (620 mg, 3.18 mmol) was dissolved in DMF (5 mL), to the solution was added NCS (424 mg, 3.18 mmol) and the reaction mixture was stirred at rt for 4 h. The reaction mixture was quenched with the addition of water (100 mL) and the solution extracted with EtOAc (2×25 mL), dried ($MgSO_4$) and evaporated under reduced pressure to an oil. The oil obtained was re-dissolved in DCM (10 mL) and cyclopent-3-ene-1-ol (2.67 g, 31.8 mmol) was added, followed by the addition of TEA (0.44 mL) and the reaction mixture stirred at rt for 14 h The resulting solution was filtered through a plug of silica gel and concentrated under reduced pressure to afford the diasteromeric mixture of intermediate 5-2 (227 mg, 26% yield). $^1$H NMR (600 MHz, $CDCl_3$) δ 8.04 (d, J=2.3 Hz, 1H), 7.85 (dd, J=8.8, 2.3 Hz, 1H), 7.03 (d, J=8.8 Hz, 1H), 5.30 (ddd, J=9.4, 6.2, 2.9 Hz, 1H), 4.50 (quin, J=5.9 Hz, 1H), 4.19 (td, J=9.3, 4.7 Hz, 1H), 3.92 (s, 3H), 2.33-2.27 (m, 1H), 2.18-2.06 (m, 3H). LC-MS RT=0.83 min; MS (ESI) m/z=278.1 $(M+H)^+$; [Method A].

The chiral intermediates of 5-2 were separated by chiral SFC by the following preparative chromatographic methods: Instrument: Berger SFC; Column: IC 25×3 cm ID, 5 μm, Temperature: 40 C, Flow rate: 85 ml/min, Mobile Phase: gradient 75/25 $CO_2$/MeOH for 12 min then to 45% MeOH, Detector Wavelength: 235 nm, Injection Volume: 1000 μL to afford chiral 5-3 Peak-1, >99% cc, Analytical RT=8.80 min), chiral 5-4 (Peak-2, >95% ee. Analytical RT=9.86 min), chiral 5-5 (Peak-3, >99% cc, Analytical RT=13.53 min), chiral 5-6 (Peak-4, >99% ee, Analytical RT=16.67 min). Analytical Chromatographic Conditions: Instrument: Agilent SFC (LVL-L4021 Lab), Column: IC 250×4.6 mm ID, 5 μm, Temperature: Ambient, Flow rate: 2.0 mL/min, Mobile Phase: gradient 75/25 $CO_2$/MeOH 12 min then to 45% MeOH. Analytical data for peak-1-4: $^1$H NMR (600 MHz, $CD_3OD$) δ 8.07 (d, J=2.2 Hz, 1H), 7.82 (dd, J=8.7, 2.1 Hz, 1H), 7.18 (d, J=8.8 Hz, 1H), 5.21 (ddd, J=9.2, 6.2, 2.5 Hz, 1H), 4.27 (m, 1H), 4.24 (td, J=9.4, 4.0 Hz, 1H), 3.94 (s, 3H), 2.16 (m, 1H), 2.05 (m, 1H), 2.00 (m, 1H), 1.99 (m, 1H). 13C NMR (151 MHz, $CD_3OD$) δ 169.5, 161.6, 160.0, 133.2, 131.4, 122.6 (2C), 113.9, 87.3, 72.7, 56.8, 51.5, 44.1, 40.3.

Intermediate 6-2: Preparation of 5-(5-(hydroxymethyl)-3a,5,6,6a-tetrahydro-4H-cyclopenta[d]-isoxazol-3-yl)-2-methoxybenzoic acid Int. 6-2

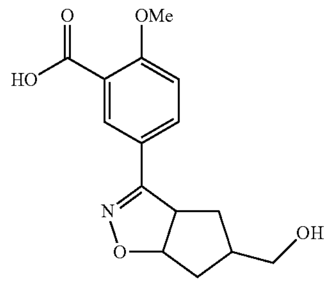

(diastereomeric mixture)

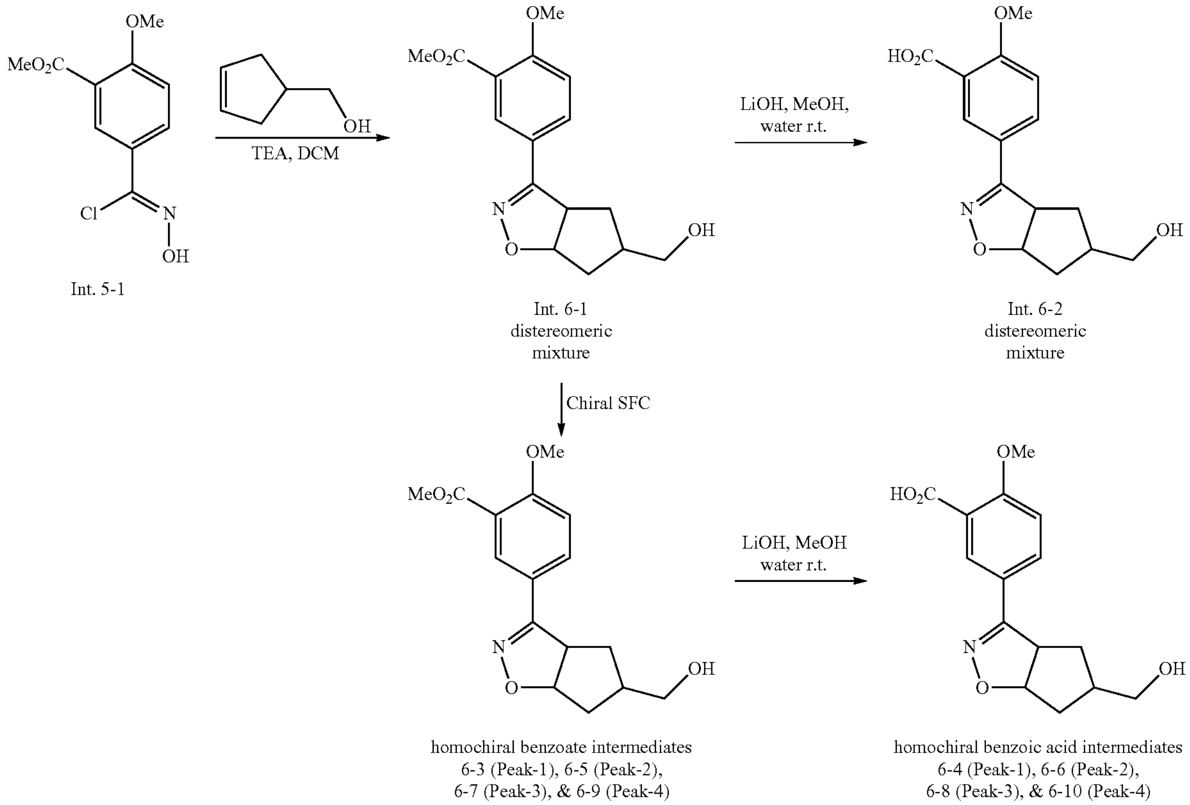

Intermediate 6-1: Intermediate 5-1 (3.0 g, 12.3 mmol) was dissolved in DCM (123.13 mL) and to this was added cyclopent-3-en-1-ylmethanol (4.8 g, 49.3 mmol) followed by the addition of TEA (5.15 mL, 36.9 mmol) and the reaction mixture was stirred at rt. After stirring 14 h, the reaction mixture was concentrated under reduced pressure and the residue purified by normal phase chromatography by eluting with hexanes/EtOAc gave 6-1 (2.8 g, 9.2 mmol, 75% yield) as an oily mass. LC-MS: RT=0.95 min; MS (ESI) m/z=306.3 (M+H);$^+$ [Method A].

Diasteromeric intermediate 6-2: Intermediate 6-1 (88 mg, 0.29 mmol) was dissolved in THF (I mL)/MeOH (1 mL) was treated with LiOH monohydrate (36 mg, 0.86 mmol) in $H_2O$ (1 mL) at rt. After 3 h, the reaction mixture was diluted with $H_2O$ (5 mL) and the pH of the aq. layer was adjusted to pH 7 with 1M HCl solution and extracted with EtOAc (2×25 mL), washed with brine, dried ($Na_2SO_4$), filtered, and evaporated under reduced pressure to give 6-2 (62 mg, 74% yield). The carboxylic acid 6-2 was carried forward to the next reaction without further purification. LC-MS: RT=0.85 min; MS (EST) m/z=292.3 (M+H);$^+$ [Method A].

Intermediates 6-3 Through 6-10 (Homochiral)

Individual chiral diastereomer ester intermediates 6-3, 6-5, 6-7, and 6-9 were obtained by chiral SFC separation of the diastereomeric mixture intermediate 6-1 (525 mg, 1.72 mmol). Chiral SFC Preparative chromatographic conditions: Instrument: Berger MG II (SFC); Column: Chiralpak AD-H, 21×250 mm, 5 micron; Mobile phase: 15% MeOH/85% $CO_2$; Flow conditions: 45 mL/min, 150 Bar, 40° C.; Detector wavelength: 210 nm; Injections details: 0.5 mL of ~35 mg/mL in MeOH. Analytical chromatographic conditions: Instrument: Shimadzu Nexera SFC; Column: Chiralpak AD-H, 4.6×100 mm, 3 micron: Mobile phase: 15% MeOH/85% $CO_2$; Flow conditions: 2.0 mL/min, 150 Bar, 40° C.; Detector wavelength: 220 nm; Injection details: 5 μL of ~1 mg/mL in MeOH.

Methylbenzoate intermediate 6-3 (Peak-1, RT=4.07 min; >99% cc) was obtained as a film (150 mg, 29% yield). $^1H$ NMR (600 MHz, $CDCl_3$) δ 8.04 (d, J=2.3 Hz, 1H), 7.87 (dd, J=8.7, 2.3 Hz, 1H), 7.01 (d, J=8.8 Hz, 1H), 5.23 (dd, J=8.8, 5.1 Hz, 1H), 4.10 (t, J=8.7 Hz, 1H), 3.94 (s, 3H), 3.90 (s, 3H), 3.72-3.66 (m, 1H), 3.61 (dt, J=10.5, 5.2 Hz, 1H), 2.30-2.16 (m, 2H), 2.05 (dd, J=13.0, 6.1 Hz, 1H), 1.76 (ddd, 0.1=12.9, 11.5, 9.4 Hz, 1H), 1.68-1.62 (m, 1H), 1.39 (br t, J=4.8 Hz, 1H).

Benzoic acid intermediate 6-4: Preparation of 5-(5-(hydroxymethyl)-3a,5,6,6a-tetrahydro-4H-cyclopenta[d]isoxazol-3-yl)-2-methoxybenzoic acid. Intermediate 6-4 (100 mg, 78% yield) was prepared in a similar manner as intermediate 6-2 with the hydrolysis of intermediate 6-3. LC-MS: RT=0.85 min; (ESI) m/z=292.3 $(M+H)^+$; [Method A].

Methylbenzoate intermediate 6-5 (Peak-2, RT=4.55 min; >99% ee) was obtained as a film (33.2 mg, 6.3% yield). $^1H$ NMR (600 MHz, $CDCl_3$) δ 8.05 (d, J=2.3 Hz, 1H), 7.87 (dd, J=8.8, 2.3 Hz, 1H), 7.02 (d, J=8.8 Hz, 1H), 5.25 (ddd, J=10.1, 6.2, 4.2 Hz, 1H), 4.04-3.98 (m, 1H), 3.94 (s, 3H), 3.90 (s, 3H), 3.63-3.57 (m, 1H), 3.56-3.50 (m, 1H), 2.38-2.26 (m, 3H), 1.92-1.85 (m, 1H), 1.73-1.66 (m, 1H), 1.51 (t, J=5.3 Hz, 1H). Benzoic acid intermediate 6-6: Preparation of 5-(5-(hydroxymethyl)-3a,5,6,6a-tetrahydro-4H-cyclopenta[d]isoxazol-3-yl)-2-methoxybenzoic acid. Intermediate 6-6 (20.2 mg, 92% yield) was prepared in a similar manner as intermediate 6-2 with the hydrolysis of intermediate 6-5. LC-MS: RT=0.83 min; MS (ESI) m/z=292.3 $(M+H)^+$; [Method A].

Methylbenzoate intermediate 6-7 (Peak-3, RT=5.66 min; >99% cc) was obtained as a film (161 mg, 30.6% yield). $^1H$ NMR: (600 MHz, $CDCl_3$) δ 8.05-8.03 (m, 1H), 7.86 (dd, J=8.7, 2.3 Hz, 1H), 7.01 (d, J=8.8 Hz, 1H), 5.23 (dd, J=8.7, 5.2 Hz, 1H), 4.10 (t, J=8.7 Hz, 1H), 3.94 (s, 3H), 3.90 (s, 3H), 3.69 (br dd, J=10.6, 5.2 Hz, 1H), 3.63-3.58 (m, 1H), 2.28-2.17 (m, 2H), 2.05 (br dd, J=12.9, 6.2 Hz, 1H), 1.76 (ddd, J=13.0, 11.5, 9.4 Hz, 1H), 1.64-1.60 (m, 1H), 1.49 (br s, 1H).

Benzoic acid intermediate 6-8: Preparation of 5-(5-(hydroxymethyl)-3a,5,6,6a-tetrahydro-4H-cyclopenta[d]isoxazol-3-yl)-2-methoxybenzoic acid. Intermediate 6-8 (120 mg, 85% yield) was prepared in a similar manner as intermediate 6-2 with the hydrolysis of intermediate 6-7. LC-MS: RT=0.83 min; MS (ESI) m/z=292.3 $(M+H)^+$; [Method A].

Methylbenzoate intermediate 6-9 (Peak-4, RT=9.81 min; >99% cc) was obtained as a film (47 mg, 9.0% yield). $^1H$ NMR: (600 MHz, $CDCl_3$) δ 8.04 (d, J=2.3 Hz, 1H), 7.87 (dd, J=8.7, 2.3 Hz, 1H), 7.02 (d, J=8.8 Hz, 1H), 5.24 (ddd, J=10.1, 6.2, 4.2 Hz, 1H), 4.03-3.98 (m, 1H), 3.94 (s, 3H), 3.90 (s, 3H), 3.63-3.57 (m, 1H), 3.56-3.49 (m, 1H), 2.38-2.25 (m, 3H), 1.91-1.85 (m, 1H), 1.72-1.66 (m, 1H), 1.55 (br s, 1H).

Benzoic acid intermediate 6-10. Preparation of 5-(5-(hydroxymethyl)-3a,5,6,6a-tetrahydro-4H-cyclopenta[d]isoxazol-3-yl)-2-methoxybenzoic acid. Intermediate 6-10 (18.2 mg, 52% yield) was prepared in a similar manner as intermediate 6-2 with the hydrolysis of intermediate 6-9. LC-MS: RT=0.84 min; MS (ESI) m/z=292.3 $(M+H)^+$ [Method A]

Intermediate 7-1. Preparation of 3-amino-N-(4-fluoro-3-(trifluoromethyl)phenyl)-2-naphthamide shown in scheme below:

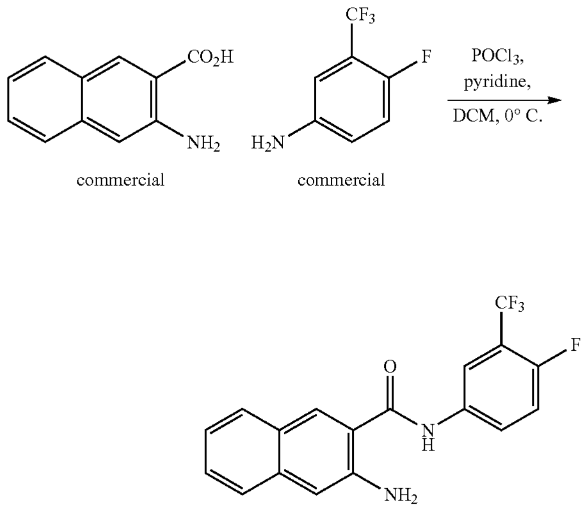

Int. 7-1

$POCl_3$ (0.25 mL, 2.7 mmol) was added to a solution of 3-amino-2-naphthoic acid (0.5 g, 3 mmol), 4-fluoro-3-(trifluoromethyl)aniline (0.96 g, 5.3 mmol), and pyridine (0.65 mL, 8.0 mmol) in DCM (26.7 ml) at 0° C. After 12 h, the reaction mixture was diluted with DCM (50 mL), the solution washed with water (50 mL), brine (2×25 mL), dried over sodium sulfate, filtered, concentrated under reduced pressure, and purified by silica gel chromatography using hexanes/EtOAc as eluents to give intermediate 7-1 (284 mg, 31% yield) as a solid. LC-MS: RT=1.09 min; MS (ESI) m/z=348.9 $(M+H)^+$; [Method A].

Intermediate 8-6. Preparation of 3-amino-5-bromo-2-naphthoic acid shown in scheme below:

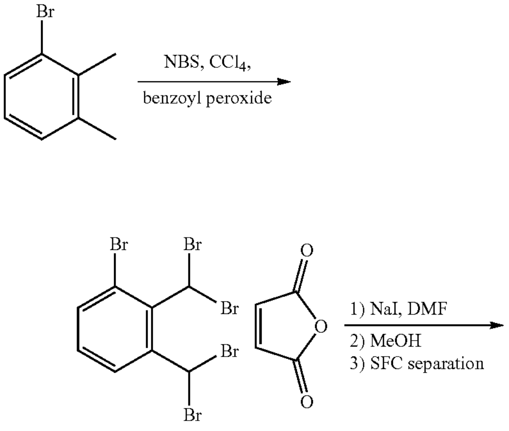

Int. 8-1

-continued

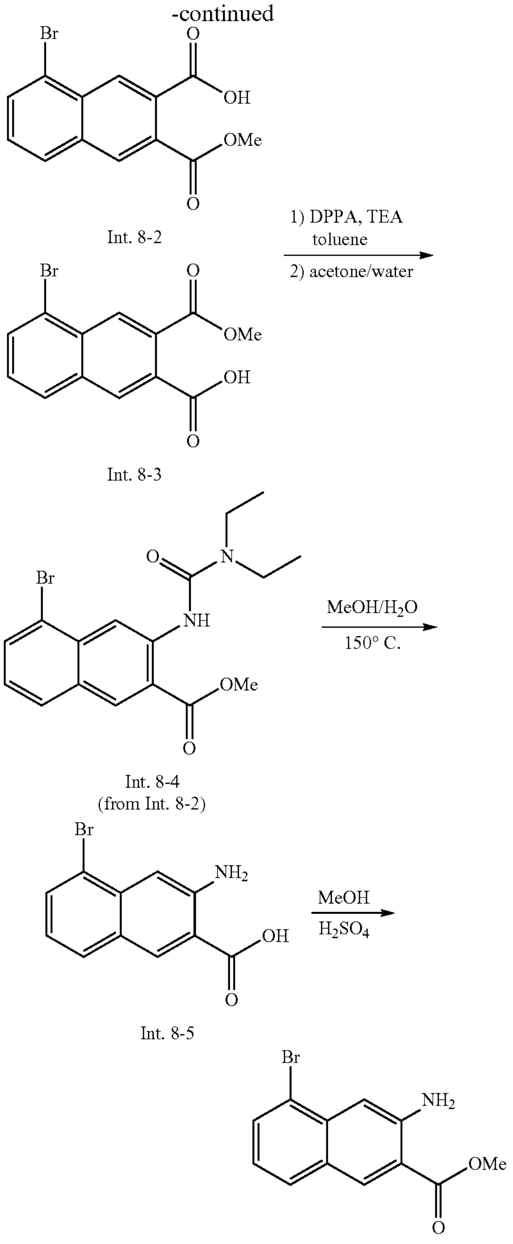

Int. 8-2

Int. 8-3

Int. 8-4
(from Int. 8-2)

Int. 8-5

Int. 8-6

Intermediate 8-1. Preparation of 1-bromo-2,3-bis(dibromomethyl)benzene. To 1-bromo-2,3-dimethylbenzene (5 g, 30 mmol) in $CCl_4$ (25 mL) was added NBS (10 g, 57 mmol), benzoyl peroxide (65 mg, 0.27 mmol) and the reaction mixture was heated to reflux for 24 h. The reaction mixture was allowed to cool to rt and additional NBS (10 g, 57 mmol) and benzoyl peroxide (65 mg, 0.27 mmol) were added and heating resumed 24 h. The reaction mixture was allowed to cool to rt and filtered. The filtrate was washed with water (3×20 mL), aq. sodium thiosulfite (20 mL), brine (20 mL) and dried ($Na_2SO_4$) to afford (13 g, 96%) of the 8-1. $^1$H NMR (400 MHz, $CDCl_3$) δ 7.99 (d, J=7.9 Hz, 1H), 7.61 (dd, J=8.0, 1.2 Hz, 1H), 7.35-7.28 (m, 2H), 7.09 (s, 1H).

Intermediate 8-2. Preparation of 8-bromo-3-(methoxycarbonyl)-2-naphthoic acid, diethylammonium salt. To intermediate 8-1 (2 g, 4 mmol) and furan-2,5-dione (0.4 g, 4 mmol) in DMF (8 mL) was added NaI (1.8 g, 12 mmol) and the reaction mixture was heated to 50° C. for 24 h. The reaction mixture was allowed to cool to rt and stirred with MeOH (10 mL) for 24 h. The solvents were concentrated in vacuo and the residue was washed with saturated sodium bisulfite and then, purified by reverse phase chromatography eluting with a gradient of (90:10) $H_2O$, AcN/0.05% TFA to (10:90) $H_2O$, AcN/0.05% TFA. Further purification by SFC using Instrument: Berger MG II Column: Chiralpak AD-H, 21×250 mm, 5 micron, Mobile Phase: 15% IPA-ACN (1:1, 0.1% DEA)/85% $CO_2$, Flow Conditions: 45 mL/min, 150 Bar, 40° C., Detector Wavelength: 240 nm; Analytical method: Instrument: Shimadzu Analytical SFC, Column Chiralpak AD-H, 4.6×100 mm, 3 micron, Mobile Phase: 20% IPA-ACN (1:1, 0.1% DEA)/80% $CO_2$; Flow Conditions: 2 mL/min, 150 Bar, 40° C., Detector Wavelength: 220 nm, to afford (Peak-1, RT=3.82 min.) and chiral (Peak-2. RT=5.26 min.). The residue was separated to afford intermediate 8-2 (Peak-1, RT=3.82 min., 0.3 g, 0.8 mmol, 30% yield). $^1$H NMR (400 MHz, DMSO-d6) δ 9.71-9.33 (m, 1H), 8.48 (s, 1H), 8.06 (d, J=8.4 Hz, 1H), 8.04 (s, 1H), 7.96 (dd, J=7.4, 1.0 Hz, 1H), 7.62-7.39 (m, 1H), 3.78 (s, 3H) and intermediate 8-3 (Peak-2, RT=5.26 min., 0.3 g, 0.8 mmol, 32% yield), $^1$H NMR (400 MHz, DMSO-d6) δ 9.26-8.90 (m, 1H), 8.31 (s, 1H), 8.13-8.07 (m, 2H), 7.97-7.93 (m, 1H), 7.52 (t, J=7.8 Hz, 1H), 3.80 (s, 3H).

Intermediate 8-4. Preparation of methyl 5-bromo-3-(3,3-diethylureido)-2-naphthoate. To intermediate 8-2 (0.3 g, 1 mmol) in toluene (10 mL) and TEA (1 mL, 7 mmol) was added diphenylphosphoryl azide (0.2 mL, 1 mmol). The reaction mixture was stirred at RT for 3 h, then added via an addition funnel to acetone (80 mL)/$H_2O$ (10 mL) at 80° C. dropwise. After 1 h, the reaction mixture was allowed warm to rt and to stir for 24 h. The solvents were reduced in vacuo and the residue partitioned with brine (20 mL) and ethyl acetate (50 mL). The aqueous layer was extracted with EtOAc (2×20 mL). The combined organic layers were washed with brine (15 mL) and dried ($MgSO_4$). The residue was purified by silica gel chromatography eluted with hexanes/EtOAc to afford intermediate 8-4 (0.17 g, 0.50 mmol, 43% yield) as a yellow solid. $^1$H NMR (400 MHz, $CDCl_3$) S 10.58 (s, 1H), 9.51 (s, 1H), 8.63 (s, 1H), 7.84 (dd, J=7.4, 1.0 Hz, 1H), 7.77 (d, J=8.4 Hz, 1H), 7.21 (dd, J=8.1, 7.5 Hz, 1H), 4.03 (s, 3H), 3.53 (q, J=7.3 Hz, 4H), 1.41-1.12 (m, 6H). MS (ESI) m/z=275-277 $(M+H)^+$.

Intermediate 8-5. Preparation of 3-amino-5-bromo-2-naphthoic acid. Intermediate 8-4 (0.17 g, 0.5 mmol) in water (10 mL) and MeOH (0.5 mL) was heated to 150° C. in a microwave oven for 2.3 h. The solvents were reduced under vacuum and, after acidification with 1 M HCl, the solid was filtered off and dried under vacuum to afford intermediate 8-5 which was used without further purification (0.1 g, 0.4 mmol, 97% yield) as a yellow solid. MS (ESI) m/z=266-268.0 $(M+H)^+$.

Intermediate 8-6. Preparation of methyl 3-amino-5-bromo-2-naphthoate. Intermediate 8-(0.1 g mg, 0.4) in MeOH (5 mL) was added 10% $H_2SO_4$/MeOH and the reaction mixture was heated to 60° C. After 24 h, the reaction mixture was allowed to cool and was filtered. The filtrate was concentrated under reduced pressure and the residue partitioned with sat'd $NaHCO_3$ (10 mL) and extracted with ethyl acetate (3×10 mL). The combined organic layers were washed with brine (15 mL), dried ($Na_2SO_4$) and concentrated under reduced pressure to afford intermediate 8-6 (0.1 g, 0.4 mmol, 90% yield) as a brown oil which was used without further purification. MS (ESI) m/z=280-282.1 $(M+H)^+$.

Intermediate 9-1. Preparation of 3-amino-5-bromo-N-(4-fluoro-3-(trifluoromethyl)phenyl)-2-naphthamide shown in scheme below:

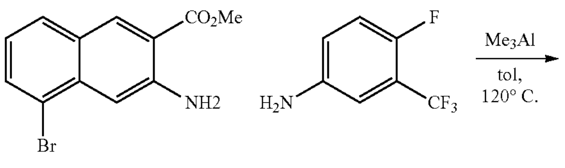

Int. 8-6

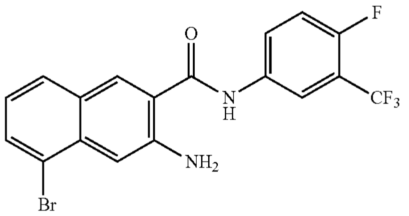

Int. 9-1

To 4-fluoro-3-(trifluoromethyl)aniline (0.2 g, 1.0 mmol) in toluene (4 mL) was added 2M solution of $Me_3Al$ (0.5 mL, 1 mmol). After 10 min, this solution was added to a mixture to intermediate 8-6 (0.1 g, 0.3 mmol) in toluene (6 mL) and the resulting solution heated under microwave irradiation at 120° C. for 30 min. The reaction mixture was quenched by the addition of 1N HCl (10 mL) and then extracted with ethyl acetate (3x30 mL). The combined organic layers were washed with brine (15 mL), dried ($MgSO_4$) and concentrated under reduced pressure. The residue was purified via silica gel chromatography eluting with hexanes/EtOAc to afford the intermediate 9-1 (54 mg, 0.13 mmol, 35% yield) as bright yellow solid. $^1H$ NMR (400 MHz, DMSO-d6) δ 10.94-10.59 (m, 1H), 8.34-8.21 (m, 2H), 8.14-8.03 (m, 1H), 7.84 (d, J=8.4 Hz, 1H), 7.77 (dd, J=7.5, 1.1 Hz, 1H), 7.57 (t, J=9.9 Hz, 1H), 7.32 (s, 1H), 7.11 (dd, J=8.1, 7.5 Hz, 1H), 6.35 (s, 2H). MS (ESI) m/z=427-429.0 (M+H).$^+$ Intermediate 11-2: Preparation of 2-methoxy-5-(6-oxopyridazin-1(6H)-yl)benzoic acid following the method outlined in the scheme below.

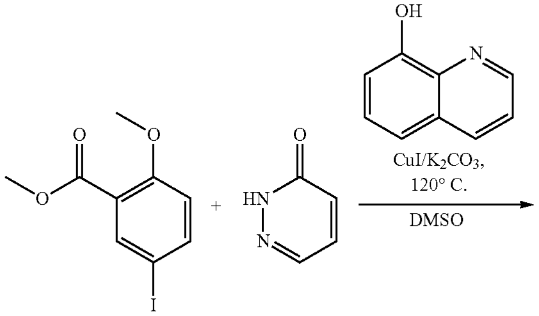

-continued

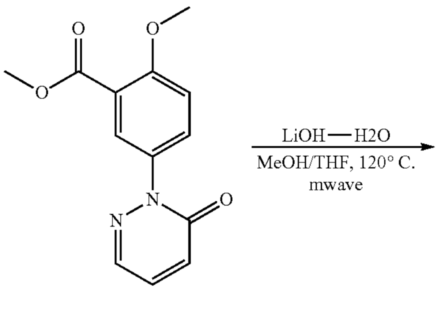

Int. 11-1

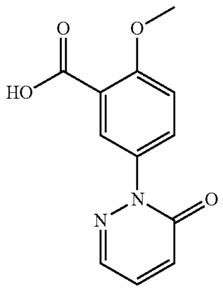

Int. 11-2

Intermediate 11-1: Preparation of methyl 2-methoxy-5-(6-oxopyridazin-1(6H)-yl)benzoate. To a pressure vial was added methyl 5-iodo-2-methoxybenzoate (100 mg, 0.34 mmol), pyridazin-3(2H)-one (29.9 mg, 0.310 mmol), quinolin-8-ol (18 mg, 0.13 mmol), copper (I) iodide (24 mg, 0.13 mmol) and $K_2CO_3$ (86 mg, 0.62 mmol) in DMSO (1.6 mL). The vessel was sealed and stirred at 140° C. for 14 h. The reaction mixture was allowed to cool and filtered through a plug of Celite®. The filtrate was purified by reverse phase chromatography eluting with a gradient of (90:10) $H_2O$, AcN/0.05% TFA to (10:90) $H_2O$, AcN/0.05% TFA to give intermediate 11-1. LC-MS: RT=0.89 min; MS (ESI) m/z=261.2 (M+H);$^+$ [Method A].

Intermediate 11-2: Preparation of 2-methoxy-5-(6-oxopyridazin-1(6H)-yl)benzoic acid. Intermediate 11-1 was dissolved in MeOH/THF (1:1; 2 mL), the solution treated with LiOH monohydrate (0.93 mL, 0.93 mmol), and heated in microwave at 120° C. for 15 min. The reaction mixture was diluted with water and extracted with EtOAc. The organics were discarded. The remaining aqueous layer was acidified with 1.0M HCl solution, and the aqueous portion extracted with EtOAc (2x50 mL). The combined organic portions were dried over sodium sulfate, filtered, and concentrated under reduced pressure to give intermediate 11-2 (44 mg, 57% yield over two steps). LC-MS: RT=0.78 min; MS (ESI) m/z=247.2 (M+H);$^+$ [Method A].

Intermediate 12-3: Preparation of (S)-5'-(1-((cyclobutylcarbamoyl)oxy)-2,2,2-trifluoroethyl)-2'-fluoro-4-methoxy-[1,1'-biphenyl]-3-carboxylic acid

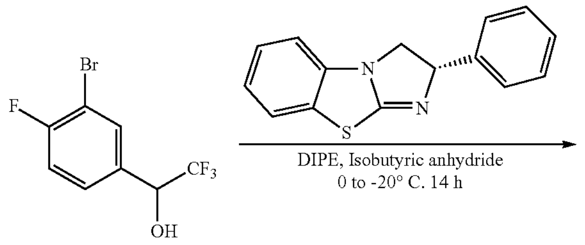

Int. 4-2

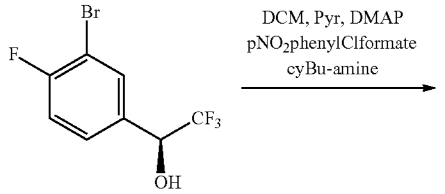

Int. 12-1
(homochiral)

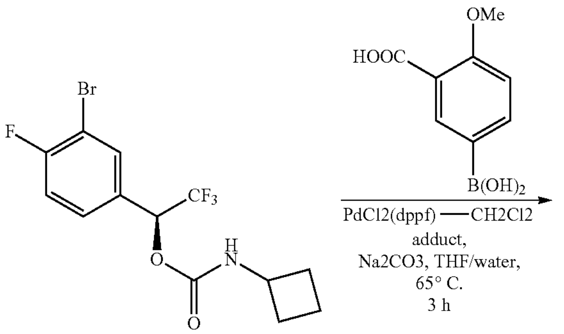

Int. 12-2
(homochiral)

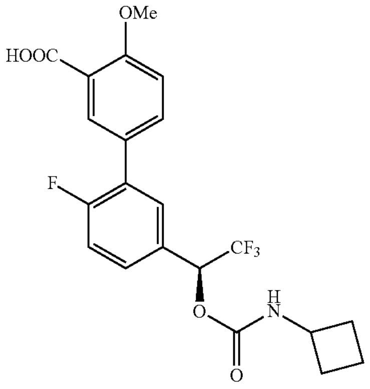

Int. 12-3
(homochiral)

Intermediate 12-1: Preparation of (S)-1-(3-bromo-4-fluorophenyl)-2,2,2-trifluoroethan-1-ol.

A solution of (S)-2-phenyl-2,3-dihydrobenzo[d]imidazo[2,1-b]thiazole (0.13 g, 0.50 mmol) and intermediate 4-2 (racemic) (3.43 g, 12.6 mmol) in diisopropyl ether (41.9 mL) was cooled to 0 to −20° C. The solution was treated with isobutyric anhydride (0.42 mL, 2.5 mmol) and transferred to a freezer for 14 h. The reaction mixture was quenched by the addition of MeOH (~1 mL), and the solution extracted from phosphate buffer with EtOAc (2×25 mL). The combined organic portions were concentrated under reduced pressure and purified by silica gel chromatography using hex/ethylacetate as eluants to afford intermediate 12-1 (chiral) (2.59 g, 9.48 mmol, 75% yield, 99% ee). 1H NMR (500 MHz, $CDCl_3$) δ 7.72 (dd, J=6.3, 1.9 Hz, 1H), 7.44-7.39 (m, 1H), 7.20-7.13 (m, 1H), 5.01 (q, J=6.6 Hz, 1H), 4.15-4.10 (m, 1H).

Intermediate 12-2: Preparation of (S)-1-(3-bromo-4-fluorophenyl)-2,2,2-trifluoroethyl cyclobutylcarbamate. Intermediate 12-1 (300 mg, 1.10 mmol), pyridine (0.44 mL, 5.5 mmol), and DMAP (13.42 mg, 0.11 mmol) were dissolved in DCM (20 mL) and 4-nitrophenyl carbonochloridate (1.1 g, 5.5 mmol) was added. After 1 h, cyclobutanamine (782 mg, 11.0 mmol) was added and stirring continued for 2 h. The reaction mixture was quenched by the addition of MeOH (3 mL), concentrated under reduced pressure, and purified by normal phase chromatography to give intermediate 12-2 (350 mg, 0.94 mmol, 85% yield) as a white solid. LC-MS: RT=1.27 min; MS (ESI) m/z=371.7 $(M+H)^+$ [Method A].

Intermediate 12-3: Preparation of (S)-5'-(1-((cyclobutylcarbamoyl)oxy)-2,2,2-trifluoroethyl)-2'-fluoro-4-methoxy-[1,1'-biphenyl]-3-carboxylic acid. Into the reaction vessel containing intermediate 12-2 (350 mg, 0.80 mmol) was added 5-borono-2-methoxybenzoic acid (203 mg, 1.04 mmol), $PdCl_2(dppf)-CH_2Cl_2$ adduct (98 mg, 0.12 mmol), $Na_2CO_3$, (338 mg, 3.19 mmol), THF (11.5 mL) and $H_2O$ (2.88 mL). The reaction mixture was degassed by bubbling $N_2$ for 10 min, sealed, and stirred at 65° C. for 3 h. The reaction mixture was allowed to cool to rt, quenched by the addition of 1 N HCl. The reaction mixture was extracted with EtOAc, dried over $Na_2SO_4$, concentrated under reduced pressure and purified by reverse phase HPLC using Phenomenex Luna AXIA C18 5 u 30×100 mm column, 10-min. gradient; Solvent A: 20% ACN-80% $H_2O$-0.1% TFA; Solvent B: 80% ACN-20% $H_2O$-0.1% TFA and lyophilized to produce intermediate 12-3 (72 mg, 0.16 mmol, 21% yield) as a solid. LC-MS: RT=0.94 min; MS (ESI) m/z=442.0 $(M+H)^+$ [Method A].

Intermediate 13-5. Preparation of 3-amino-7-bromo-N-(4-fluoro-3-(trifluoromethyl)phenyl)-2-naphthamide shown in scheme below:

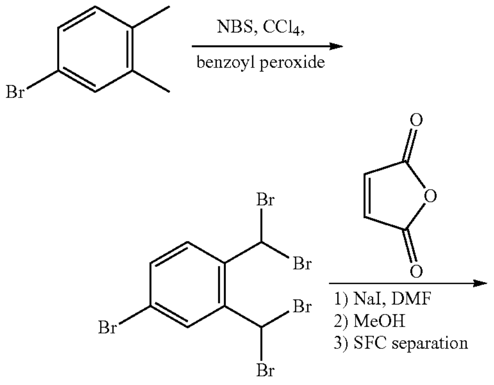

Int. 13-1

-continued

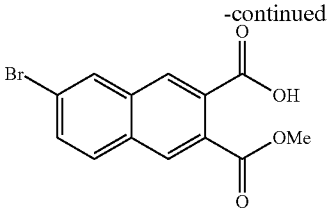

Int. 13-2
(Peak 1)

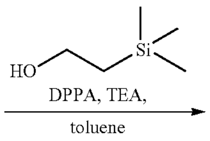

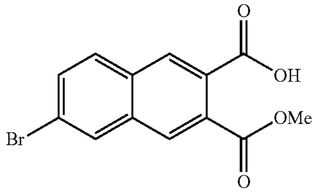

Int. 13-3
(Peak 2)

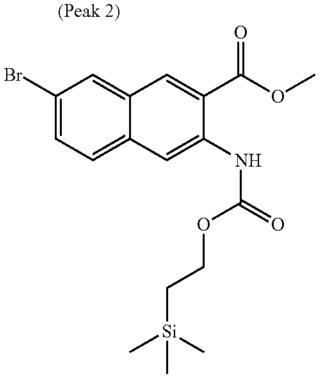

Int. 13-4
(from int. 13-2)

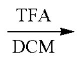

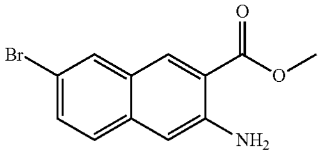

Int. 13-5

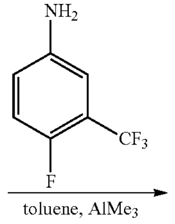

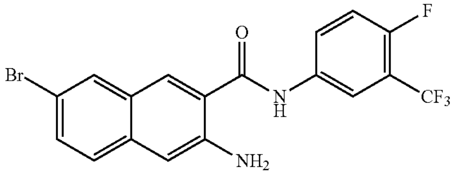

Int. 13-6

Intermediate 13-1: Preparation of 4-bromo-1,2-bis(dibromomethyl)benzene. To 4-bromo-1,2-dimnethylbenzene (1.9 g, 10 mmol) in $CCl_4$ (20 mL) was added 1-bromopyrrolidine-2,5-dione (3.84 g, 21.6 mmol) and benzoyl peroxide (0.025 g, 0.10 mmol) and the reaction mixture was heated at reflux for 14 h. After allowing to cool to rt, the solids were collected by filtration, rinsed with DCM (2×25 mL), and discarded. The filtrate was washed with water (3×20 mL), sodium thiosulfite solution (20 mL), brine, dried over $Na_2SO_4$, filtered, and concentrated under reduced pressure to give 4-bromo-1,2-bis(dibromomethyl)benzene, intermediate 13-1 (4.9 g, 9.8 mmol, 95% yield) yellow solid which was used without further purification. $^1$H NMR (400 MHz, $CDCl_3$) δ 7.90-7.80 (m, 1H), 7.65-7.57 (m, 1H), 7.56-7.49 (m, 1H), 7.15-6.98 (m, 2H).

Intermediates 13-2 and 13-3: Preparation of 7-bromo-3-(methoxycarbonyl)-2-naphthoic acid and 6-bromo-3-(methoxycarbonyl)-2-naphthoic acid. To a solution of intermediate 13-1 (2.2 g, 4.4 mmol) and furan-2,5-dione (0.47 g, 4.8 mmol) in DMF (8 mL) was added sodium iodide (1.98 g, 13.2 mmol) and heated to 50° C. After stirring for 14 h, the reaction mixture was allowed to cool to rt and stirred with MeOH (10 mL) for 24 h. The solvents were removed by concentrating in vacuo and the residue was washed with saturated sodium bisulfite and purified by reverse phase chromatography eluting with a gradient of (90:10:0.05) $H_2O$, AcN, TFA to (10:90:0.05) $H_2O$, AcN, TFA. Further purification by SFC using Instrument: Berger MG 11 Column: Chiralpak AD-H, 21×250 mm, 5 micron; Mobile Phase: 15% IPA-ACN (1:1, 0.1% DEA)/85% $CO_2$; Flow Conditions: 45 mL/min, 150 Bar, 40° C.; Detector Wavelength: 233 nm; Injection Details: 0.5 mL of ~10 mg/mL in MeOH-IPA (1:1, 0.1% DEA); Analytical SFC using Instrument: Shimadzu; Column: Chiralpak AD-H, 4.6×100 mm, 3 micron; Mobile Phase: 20% IPA-ACN (1:1, 0.1% DEA)/80% $CO_2$; Flow Conditions: 2.0 mL/min, 150 Bar, 40° C., Detector Wavelength: 220 nm; Injection Details: 10 μL of ~1 mg/mL in MeOH to afford intermediate 13-2 (Peak-1, RT=4.32 min) (350 mg, 21% yield) and intermediate 13-3 (Peak-2; RT=5.89 min) (370 mg, 22% yield). For 13-2: $^1$H NMR (400 MHz, DMSO-d6) δ 10.04-9.54 (m, 1H), 8.31 (d, J=1.8 Hz, 1H), 8.22 (s, 1H), 8.00 (s, 1H), 7.97 (d, J=9.0 Hz, 1H), 7.69 (dd, J=8.8, 2.0 Hz, 1H), 3.77 (s, 3H). MS (ESI) m/z=308.8-310.8 $(M+H)^+$. For 13-3: $^1$H NMR (400 MHz, DMSO-d6) δ 9.62-9.31 (m, 1H), 8.31-8.17 (m, 2H), 7.99 (d, J=8.8 Hz, 1H), 7.94 (s, 1H), 7.70 (dd, J=8.7, 2.1 Hz, 1H), 3.77 (s, 3H). MS (ESI) m/z=309-311.0 $(M+H)^+$.

Intermediate 13-4: Preparation of methyl 7-bromo-3-(((2-(trimethylsilyl)ethoxy)carbonyl)-amino)-2-naphthoate. Into a 3 necked RBF, charged 6-bromo-3-(methoxycarbonyl)-2-naphthoic acid 13-3 (180 mg, 0.57 mmol) in toluene (8 mL) was added TEA (0.18 mL, 1.3 mmol) and diphenylphosphoryl azide (0.10 mL, 0.48 mmol). The reaction mixture was stirred at it for 2.5 h then 2-(trimethylsilyl)ethan-1-ol (0.32 mL, 2.3 mmol) was added and the reaction mixture heated at 80° C. for 1 h. The reaction mixture was allowed to cool and was concentrated under reduced pressure and purified by normal phase chromatography to afford intermediate 13-4 (175 mg, 0.412 mmol, 72.4% yield) white solid. $^1$H NMR (400 MHz, $CDCl_3$) δ 10.50-10.21 (m, 1H), 8.84 (s, 1H), 8.56 (s, 1H), 8.19-7.88 (m, 1H), 7.82-7.55 (m, 2H), 4.44-4.26 (m, 2H), 4.03 (s, 3H), 1.18-1.06 (m, 2H), 0.12 (s, 9H).

Intermediate 13-5: Preparation of methyl 3-amino-7-bromo-2-naphthoate. Intermediate 13-4 (167 mg, 0.394 mmol) was deprotected by treatment with 20% TFA/DCM (4 mL). After 14 h, the reaction mixture was concentrated under reduced pressure and further dried under high vacuum to give intermediate 13-5 (110 mg, 0.393 mmol, 100% yield). $^1$H NMR (400 MHz, DMSO-d6) δ 8.45 (s, 1H), 8.08 (d, J=1.3 Hz, 1H), 7.56-7.50 (m, 1H), 7.50-7.45 (m, 1H), 7.07 (s, 1H), 6.55 (s, 2H), 3.90 (s, 3H). LC-MS: RT=1.29 min; MS (ESI) m/z=280-282 $(M+H)^+$; [Method A].

Intermediate 13-6: Preparation of 3-amino-7-bromo-N-(4-fluoro-3-(trifluoromethyl)phenyl)-2-naphthamide.

4-fluoro-3-(trifluoromethyl)aniline (211 mg, 1.18 mmol) in toluene (I mL) was stirred with $Me_3Al$ (589 μl, 1.18 mmol), for 10 min and then added to intermediate 13-5 (110 mg, 0.393 mmol) in toluene (9 mL). The solution was heated under microwave irradiation at 120° C. for 30 min. The reaction mixture was quenched with the addition of dilute HCl (10 mL) and extracted with EtOAc (3×20 mL). The combined organic layers were washed with brine (15 mL), dried ($Na_2SO_4$), filtered, concentrated under reduced pressure and purified by normal phase chromatography to afford intermediate 13-6 (140 mg, 0.33 mmol, 85% yield). $^1$H NMR (400 MHz, DMSO-d6) δ 10.78 (s, 1H), 8.27 (dd, J=6.6, 2.6 Hz, 1H), 8.16 (s, 1H), 8.06 (ddd, J=8.7, 4.1, 2.9 Hz, 1H), 8.02 (d, J=2.0 Hz, 1H), 7.61-7.54 (m, 2H), 7.51-7.47 (m, 1H), 7.06 (s, 1H), 6.08 (s, 2H). LC-MS: RT=1.37 min; MS (ESI) m/z=427.9-429.9 $(M+H)^+$ [Method A].

Intermediate 14-3. Preparation of 5-((3-hydroxypropyl)sulfonyl)-2-methoxybenzoic acid shown in scheme below:

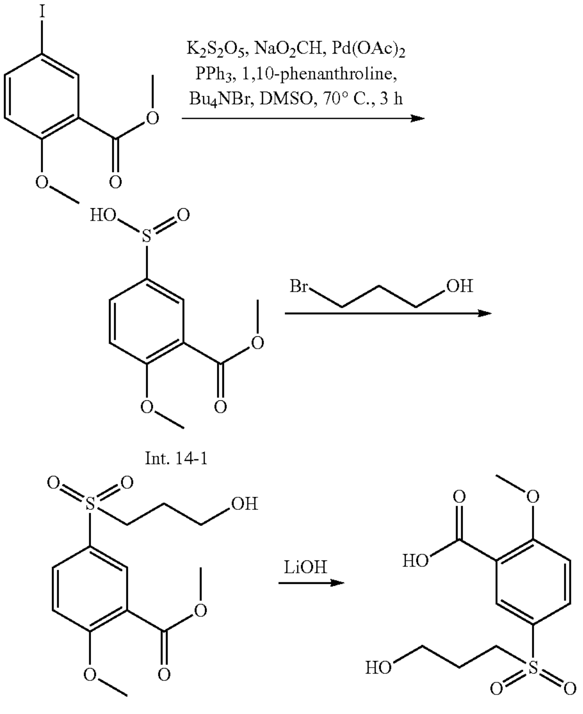

Int. 14-1

Int. 14-2

Int. 14-3

Intermediate 14-1: Preparation of 4-methoxy-3-(methoxycarbonyl)benzenesulfinate. Methyl 5-iodo-2-methoxybenzoate (200 mg, 0.69 mmol), potassium metabisulfite (304 mg, 1.37 mmol), sodium formate (102 mg, 1.51 mmol), tetrabutylammonium bromide (243 mg, 0.750 mmol), 1,10-phenanthroline (37 mg, 0.21 mmol), triphenylphosphine (54 mg, 0.21 mmol), and $Pd(OAc)_2$ (15.4 mg, 0.068 mmol) were added to DMSO (5 mL), degassed with $N_2$, and heated at 70° C. After 3 h, the reaction mixture was allowed to cool to rt and used in the next step without further purification.

Intermediate 14-2: Preparation of methyl 5-((3-hydroxypropyl)sulfonyl)-2-methoxybenzoate. Intermediate 14-1 was treated with 3-bromopropan-1-ol (310 μl, 3.42 mmol). After stirring for 14 h, the reaction mixture was washed with brine (10 mL) and purified by normal phase chromatography by eluting with hexanes/EtOAc to give intermediate 14-2 (150 mg, 76% yield). $^1$H NMR (500 MHz, $CDCl_3$) δ 8.34 (d, J=2.4 Hz, 1H), 8.02 (dd, J=8.9, 2.4 Hz, 1H), 7.14 (d, J=8.9 Hz, 1H), 3.99 (s, 3H), 3.91 (s, 3H), 3.79-3.72 (m, 2H), 3.32-3.19 (m, 2H), 2.05-1.96 (m, 2H), 1.92-1.75 (m, 1H) LC-MS: RT=0.86 min; MS (ESI) m/z=289.1 $(M+H)^+$ [Method A].

Intermediate 14-3: Preparation of 5-((3-hydroxypropyl)sulfonyl)-2-methoxybenzoic acid. The benzoate methyl 5-((3-hydroxypropyl)sulfonyl)-2-methoxybenzoate (150 mg, 0.520 mmol) from the previous step was dissolved in THF (5 mL) and treated with LiOH (2M, 0.78 mL, 1.56 mmol) in $H_2O$ (1.67 mL). After 1 h, the reaction mixture was acidified by 1M HCl solution, extracted with EtOAc (2×10 mL), washed with $H_2O$, brine, dried over sodium sulfate, filtered, and concentrated to give intermediate 14-3 (28 mg, 19% yield). $^1$H NMR (500 MHz, $CD_3OD$) δ 8.30 (d, J=2.4 Hz, 1H), 8.06 (dd, J=8.9, 2.4 Hz, 1H), 7.39 (d, J=8.9 Hz, 1H), 3.91 (s, 3H), 3.61 (t, J=6.1 Hz, 2H), 3.31-3.22 (m, 2H), 1.95-1.79 (m, 2H) LC-MS: RT=0.74 min; MS (ESI) m/z=275.1 $(M+H)^+$ [Method A].

Intermediate 15-2. Preparation of (S)-5-(3-hydroxybut-1-yn-1-yl)-2-methoxybenzoic acid shown in scheme below:

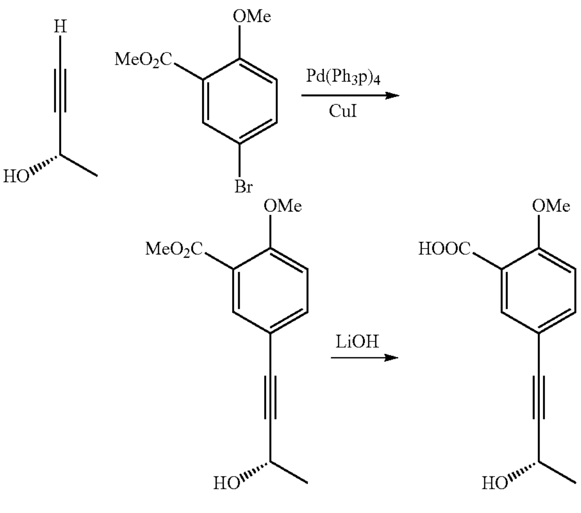

Int. 15-1

Int. 15-2

Intermediate 15-1. Preparation of methyl (S)-5-(3-hydroxybut-1-yn-1-yl)-2-methoxybenzoate. A slurry of methyl 5-bromo-2-methoxybenzoate (500 mg, 2.04 mmol), propargyl alcohol (0.15 mL, 2.6 mmol), $Pd(Ph_3P)_4$ (47. mg, 0.041 mmol) and copper (I) iodide (3.9 mg, 0.020 mmol) in TEA (5 mL) was degassed, blanketed under $N_2$ and heated to 80° C. for 14 h. The reaction mixture was allowed to cool, water was added and the aqueous portion extracted with EtOAc. The organic portion was then washed with brine, dried over sodium sulfate, filtered, concentrated under reduced pressure and the residue purified by normal phase chromatography by eluting with hexanes/EtOAc to furnish intermediate 15-1 (390 mg, 1.6 mmol, 81% yield). LC-MS: RT=0.72 min; MS (ESI) m/z=235.1 $(M+H)^+$ [Method A].

Intermediate 15-2. Preparation of (S)-5-(3-hydroxybut-1-yn-1-yl)-2-methoxybenzoic acid. A solution of intermediate 15-1 (190 mg, 0.81 mmol) in THF (6 mL) was treated with LiOH (34 mg, 0.81 mmol) in water (2 mL). The reaction mixture was acidified by 0.1 N HCL, extracted with EtOAc (20 mL), concentrated under reduced pressure and the residue used without further purification, 15-2 (179 mg, 0.811 mmol, 100% yield). LC-MS: RT=0.61 min; MS (ESI) m/z=221.1 $(M+H)^+$ [Method A].

Intermediate 16-2. Preparation of 5-(1,1-dioxidoisothiazolidin-2-yl)-2-methoxybenzoic acid

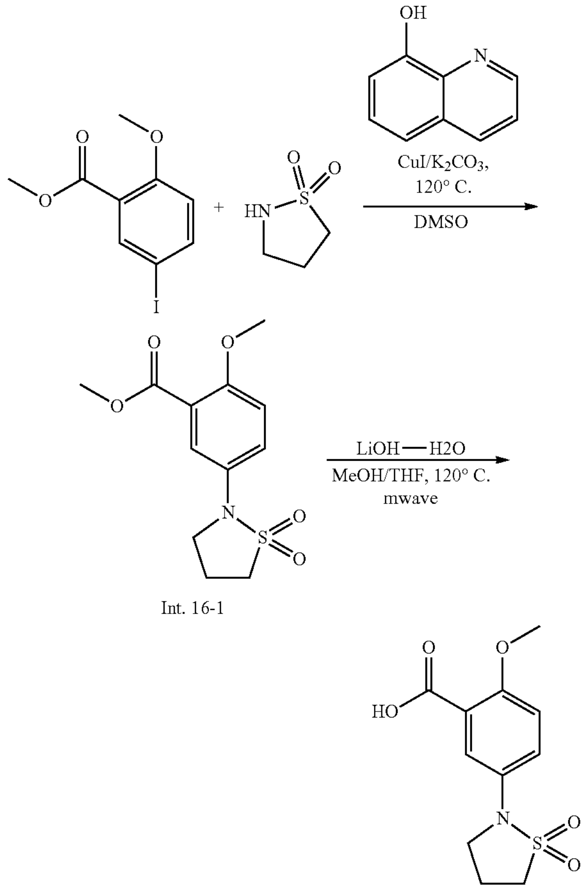

Int. 16-1
Int. 16-2

A solution containing isothiazolidine 1,1-dioxide (41 mg, 0.30 mmol), methyl 5-iodo-2-methoxybenzoate (0.1 g, 0.3 mmol), Xantphos (20 mg, 0.034 mmol), $Cs_2CO_3$ (0.2 g, 0.7 mmol) in dioxane (1.8 mL) was purged with nitrogen for 10 min. followed by addition of $Pd_2(dba)_3$ (16 mg, 1.7 μmol). The resulting reaction mixture was heated at 100° C. for 15 h. On cooling, the reaction mixture was partitioned with water (10 mL) and ethyl acetate (30 mL). The aqueous layer was extracted with ethyl acetate (2×20 mL). The combined organic layers were washed with brine (15 mL) and dried ($MgSO_4$), filtered and concentrated under reduced pressure to afford intermediate 16-1 which was immediately placed in THF (2 mL)/MeOH (0.5 mL)/water (0.5 mL), cooled to 0° C., and LiOH (2M, 0.17 mL, 0.34 mmol) was added. After 3 h, the reaction mixture was partitioned with water (10 mL) and $Et_2O$ (50 mL). The aqueous layer was acidified and extracted with ethyl acetate (3×20 mL). The combined organic layers were washed with brine (15 mL) and dried ($MgSO_4$), filtered and concentrated under reduced pressure to afford the intermediate 16-2 (70 mg, 0.26 mmol, 75% yield) as a brown oil which was used in the next step without further purification. $^1$H NMR (400 MHz, $CDCl_3$) δ 7.89-7.87 (m, 1H), 7.20-7.17 (m, 1H), 6.87 (d, J=8.8 Hz, 1H), 4.13-4.09 (m, 3H), 3.51-3.40 (m, 2H), 3.14-3.03 (m, 2H), 2.53-2.43 (m, 2H). LCMS: (ESI) m/z: 272.1 $(M+H)^+$.

Intermediate 17-4. Preparation of 3-amino-6,7-dibromo-N-(4-fluoro-3-(trifluoromethyl)phenyl)-2-naphthamide shown in scheme below:

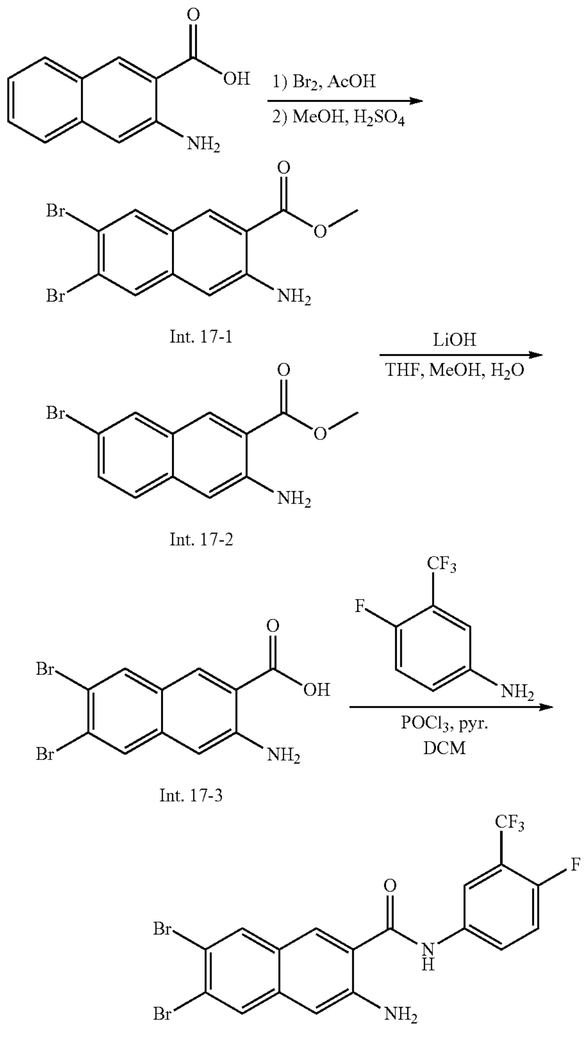

Int. 17-1
Int. 17-2
Int. 17-3
Int. 17-4

Intermediate 17-1 and 17-2. Preparation of methyl 3-amino-6,7-dibromo-2-naphthoate and methyl 3-amino-7-bromo-2-naphthoate. Intermediate 17-1 (0.39 g, 1.39 mmol, 43% yield) and intermediate 17-2 (0.33 g, 0.92 mmol, 28% yield) were prepared as described in Torikai, K, et al. *Bioorg. Med. Chem.* 2017, 25(20), 5216-37. For 17-1: $^1$H NMR (400 MHz, DMSO-$d_6$) δ 8.58 (s, 1H), 8.25 (d, J=2.0 Hz, 1H), 7.85-7.80 (m, 1H), 7.76-7.69 (m, 1H), 6.76 (br s, 2H), 3.94 (s, 3H). LCMS: (ESI) m/z: 357-359.6 $(M+H)^+$. For 17-2: $^1$H NMR (400 MHz, DMSO-$d_6$) δ 8.65-8.53 (m, 1H), 7.95 (d, J=8.1 Hz, 1H), 7.89 (dd, J=8.6, 0.7 Hz, 1H), 7.65 (ddd, J=8.5, 7.0, 1.2 Hz, 1H), 7.32 (ddd, J=8.1, 7.0, 1.0 Hz, 1H), 6.90-6.43 (m, 2H), 4.16-3.83 (m, 3H). LCMS: (ESI) m/z: 280-281.8 $(M+H)^+$.

Intermediate 17-3. Preparation of 3-amino-6,7-dibromo-2-naphthoic acid. Intermediate 17-3 (0.2 g, 0.6 mmol, 100% yield) was prepared as described for intermediate 6-2. LCMS: (ESI) m/z: 265-267.8 $(M+H)^+$.

Intermediate 17-4. Intermediate 17-4 (0.17 g, 0.34 mmol, 85% yield) was prepared in a manner similar to intermediate 7-1, substituting intermediate 17-3 for 3-amino-2-naphthoic acid. $^1$H NMR (400 MHz, DMSO-$d_6$) δ 10.94 (s, 1H), 8.32-8.23 (m, 2H), 8.16 (d, J=2.0 Hz, 1H), 8.06 (dt, J=8.0, 4.0 Hz, 1H), 7.86 (d, J=9.2 Hz, 1H), 7.73 (dd, J=9.0, 2.0 Hz, 1H), 7.59 (t, J=9.8 Hz, 1H), 6.25 (s, 2H). LCMS: (ESI) m/z: 504.8-508.9 (M+H).$^+$ Intermediate 18-1. Preparation of tert-butyl 2-((tert-butoxycarbonyl)amino)-2-(6-fluoro-3'-((3-((4-fluoro-3-(trifluoromethyl)phenyl)carbamoyl)naphthalen-2-yl)carbamoyl)-4'-methoxy-[1,1'-biphenyl]-3-yl) acetate

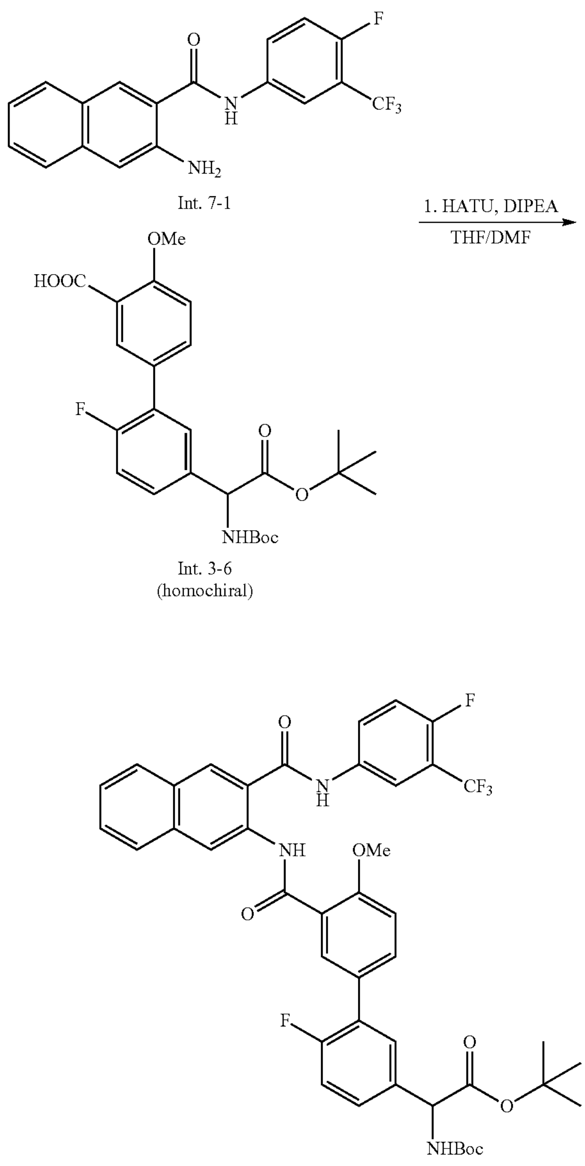

Int. 7-1

Int. 3-6
(homochiral)

Int. 18-1
(homochiral)

Intermediate 18-1. Intermediate 7-1 (25 mg, 0.072 mmol), intermediate 3-6 (34 mg, 0.072 mmol), DIPEA (9.3 mg, 0.072 mmol), 2-(3H-[1,2,3]triazolo[4,5-b]pyridin-3-yl)-1,1,3,3-tetramethylisouronium hexafluorophosphate (V) (27 mg, 0.072 mmol) were added to THF/DMF (1:1, 2 mL) and the reaction mixture heated at 50° C. for 14 h. The reaction mixture was purified by reverse phase chromatography using gradients of Solvent A (80% water, 20% ACN, 0.1% TFA) and Solvent B (5% water, 95% ACN, 0.1% TFA) to give intermediate 18-1 (13 mg, 22% yield) as a solid. $^1$H NMR (500 MHz, $CDCl_3$) δ 11.29 (br s, 1H), 10.26-10.13 (m, 1H), 8.75 (s, 1H), 8.68 (s, 1H), 8.50 (br d, J=4.1 Hz, 1H), 8.11 (d, J=8.2 Hz, 1H), 7.83 (s, 1H), 7.80-7.70 (m, 1H), 7.59 (br d, J=5.5 Hz, 1H), 7.41-7.19 (m, 2H), 7.15-7.08 (m, 1H), 7.08-6.99 (m, 3H), 5.80 (br s, 1H), 5.31 (br s, 1H), 4.12 (br s, 2H), 3.85 (s, 3H), 1.49-1.43 (m, 18H).

Example 1

6-fluoro-3'-((3-((4-fluoro-3-(trifluoromethyl)phenyl) carbamoyl)naphthalen-2-yl)carbamoyl)-4'-methoxy-[1,1'-biphenyl]-3-carboxylic acid

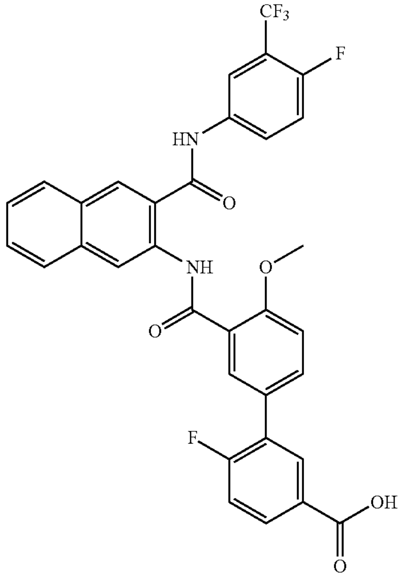 [SMILES: COc1ccc(-c2cc(C(=O)O)ccc2F)cc1C(=O)Nc1cc2ccccc2cc1C(=O)Nc1ccc(F)c(C(F)(F)F)c1]

Example 1 was prepared by adding intermediate 7-1 (50 mg, 0.14 mmol) to ACN (5.7 mL) followed by DIPEA (0.58 mL, 3.3 mmol) and intermediate 1-1 (50 mg, 0.14 mmol) and HATU (66 mg, 0.17 mmol). After 14 h, the reaction mixture was partitioned between water and EtOAc (25 mL). The organic layer was washed with water, 1M HCl solution, brine, dried over sodium sulfate, filtered, and concentrated under reduced pressure. The residue was dissolved in DCM (5 mL) and treated with TFA (1 mL). After 3 h, the reaction mixture was concentrated under reduced pressure and purified by reverse phase chromatography using gradients of Mobile Phase A: 5:95 acetonitrile:water with ammonium acetate (10 mM); Mobile Phase B: 95:5 acetonitrile:water with ammonium acetate (10 mM) to give example 1 (2.7 mg, 3% yield) as a solid. $^1$H NMR (500 MHz, DMSO-d6) δ 11.61-11.57 (m, 1H), 11.18-11.14 (m, 1H), 9.07 (s, 1H), 8.44 (s, 1H), 8.39 (br d, J=5.0 Hz, 1H), 8.27 (s, 1H), 8.14-8.06 (m, 2H), 8.04-7.94 (m, 3H), 7.82 (br d, J=8.8 Hz, 1H), 7.66-7.53 (m, 3H), 7.46 (t, J=9.5 Hz, 1H), 7.38 (d, J=8.8 Hz, 1H), 4.07 (s, 3H). Analytical LC-MS: RT=2.49 min; MS (ESI) m/z=621.1 (M+H);$^+$ HPLC purity 97%; [Method C].

Example 2

2-(6-fluoro-3'-((3-((4-fluoro-3-(trifluoromethyl)phenyl)carbamoyl)naphthalen-2-yl)carbamoyl)-4'-methoxy-[1,1'-biphenyl]-3-yl)-2-(tetrahydro-2H-pyran-4-carboxamido)acetic acid

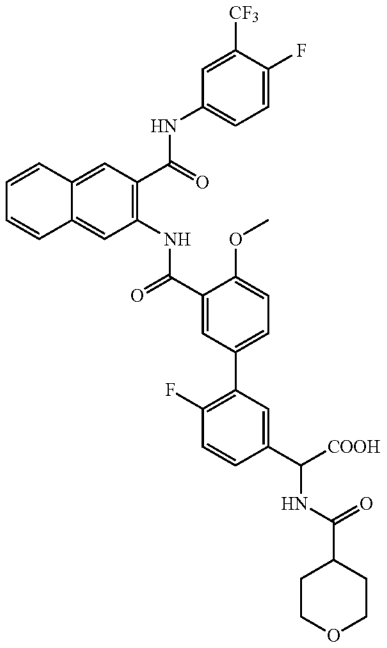 [SMILES: COc1ccc(-c2cc(C(NC(=O)C3CCOCC3)C(=O)O)ccc2F)cc1C(=O)Nc1cc2ccccc2cc1C(=O)Nc1ccc(F)c(C(F)(F)F)c1]

Example 2 was prepared by dissolving Intermediate 18-1 (13 mg, 0.016 mmol) in EtOAc (2 mL) and treating with HCl in dioxane (4N, 3 mL). After 2 h, the reaction mixture was concentrated under reduced pressure to give the amine HCl salt intermediate. The solid was re-dissolved in DCM (1 mL) and to this solution was added tetrahydro-2H-pyran-4-carbonyl chloride (2.4 mg, 0.016 mmol) followed by DIEA (0.05 ml). After 1 h, the solution was concentrated under reduced pressure, re-dissolved in DCM (1 mL), and to this was added TFA (1 mL). After 2 h, the reaction mixture was concentrated under reduced pressure and the residue was purified by reverse phase chromatography using gradients of Mobile Phase A: 5:95 ACN:water with ammonium acetate (10 mM); Mobile Phase B: 95:5 ACN:water with ammonium acetate (10 mM) to give example 2 (2.9 mg, 24% yield). $^1$H NMR (500 MHz, DMSO-d6) δ 11.59 (s, 1H), 9.07 (s, 1H), 8.43 (s, 2H), 8.38 (br d, J=6.6 Hz, 1H), 8.25 (s, 1H), 8.10 (br d, J=9.2 Hz, 1H), 8.02 (d, J=8.2 Hz, 1H), 7.95 (d, J=8.2 Hz, 1H), 7.76 (br d, J=8.5 Hz, 1H), 7.66-7.52 (m, 4H), 7.43-7.35 (m, 2H), 7.28 (t, J=9.5 Hz, 1H), 5.26 (br d, J=7.0 Hz, 1H), 4.06 (s, 3H), 3.85 (br s, 2H), 3.62 (br s, 1H), 3.35-3.27 (m, 2H), 1.65-1.51 (m, 4H). Analytical LC-MS: RT=1.93 min; MS (ESI) m/z=762.1 $(M+H)^+$; HPLC purity 100%; [Method B].

Example 3

2-(3'-((6,7-dibromo-3-((4-fluoro-3-(trifluoromethyl)phenyl)-carbamoyl)naphthalen-2-yl)carbamoyl)-6-fluoro-4'-methoxy-[1,1'-biphenyl]-3-yl)-2-(tetrahydro-2H-pyran-4-carboxamido)acetic acid

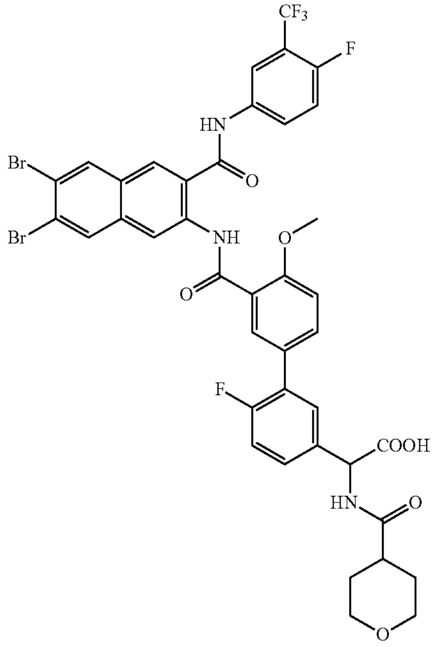 [SMILES: COc1ccc(-c2cc(C(NC(=O)C3CCOCC3)C(=O)O)ccc2F)cc1C(=O)Nc1cc2cc(Br)c(Br)cc2cc1C(=O)Nc1ccc(F)c(C(F)(F)F)c1]

The title compound was prepared (1.5 mg, 1.6 μmol, 3.7% yield) by coupling intermediate 17-4 (22 mg, 0.043 mmol) with intermediate 3-6 (21 mg, 0.043 mmol), with 1-methyl-1H-imidazole (4 mg, 0.043 mmol) in ACN (1 mL), followed by TCFH (12 mg, 0.043 mmol). After 24 h, the solvents were removed in vacuo, the residue was treated with 4N HCl (0.5 mL) in EtOAc (2 mL) for 1 h and the solvents were removed in vacuo. To the residue was added tetrahydro-2H-pyran-4-carbonyl chloride (7 mg, 0.043 mmol) in DCM (1 mL) followed by DIEA (38 μl, 0.22 mmol). The reaction mixture was stirred for 0.5 h, then concentrated in vacuo. The residue was Purified by reverse phase HPLC to afford example 3 (1.5 mg, 1.6 μmol, 3.7% yield). $^1$H NMR (500 MHz, DMSO-$d_6$) δ 10.96-10.73 (m, 1H), 10.44 (s, 1H), 8.54 (br d, J=7.3 Hz, 1H), 8.49 (d, J=1.5 Hz, 1H), 8.36 (s, 1H), 8.24 (d, J=9.2 Hz, 1H), 8.17-8.10 (m, 1H), 8.02-7.90 (m, 3H), 7.73 (br d, J=8.2 Hz, 1H), 7.52 (br s, 1H), 7.49-7.44 (m, 1H), 7.43-7.35 (m, 2H), 7.27 (br dd, J=10.7, 8.5 Hz, 1H), 5.36 (br d, J=7.6 Hz, 1H), 4.05 (s, 3H), 3.91-3.77 (m, 2H), 3.44-3.17 (m, 1H), 1.97-1.19 (m, 5H). Analytical LC-MS: RT=2.02 min; MS (ESI) m/z=918 $(M+H)^+$; HPLC purity 98%; [Method B].

Example 4

2-(6-fluoro-3'-((3-((4-fluoro-3-(trifluoromethyl)phenyl)carbamoyl)naphthalen-2-yl)carbamoyl)-4'-methoxy-[1,1'-biphenyl]-3-yl)-2-hydroxyacetic acid (Homochiral)

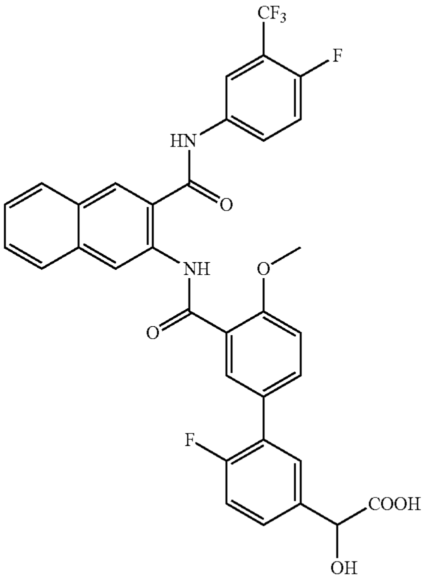 [SMILES: COc1ccc(-c2cc(C(O)C(=O)O)ccc2F)cc1C(=O)Nc1cc2ccccc2cc1C(=O)Nc1ccc(F)c(C(F)(F)F)c1]

Example 4 (5.7 mg, 0.0090 mmol, 11% yield) was prepared in a similar manner as example 1 replacing intermediate 1-1 with intermediate 2-6 (30 mg, 0.080 mmol). $^1$H NMR (500 MHz, DMSO-d6) δ 11.61-11.56 (m, 1H), 11.15 (s, 1H), 9.05 (s, 1H), 8.43-8.40 (m, 1H), 8.37 (br d, J=6.0 Hz, 1H), 8.24 (s, 1H), 8.08 (br s, 1H), 8.02 (br d, J=8.1 Hz, 1H), 7.95 (d, J=8.2 Hz, 1H), 7.76 (br d, J=8.6 Hz, 1H), 7.64 (t, J=7.5 Hz, 1H), 7.60-7.51 (m, 2H), 7.50-7.42 (m, 1H), 7.41-7.26 (m, 1H), 4.05 (s, 1H), 3.75 (br s, 3H). Analytical LC-MS: RT=2.28 min; MS (ESI) m/z=650.9 (M+H);$^+$ HPLC purity 98%; [Method B].

Example 5

(S)-2,2,2-trifluoro-1-(6-fluoro-3'-((3-((4-fluoro-3-(trifluoromethyl)phenyl)carbamoyl)-naphthalen-2-yl)carbamoyl)-4'-methoxy-[1,1'-biphenyl]-3-yl)ethyl cyclobutylcarbamate

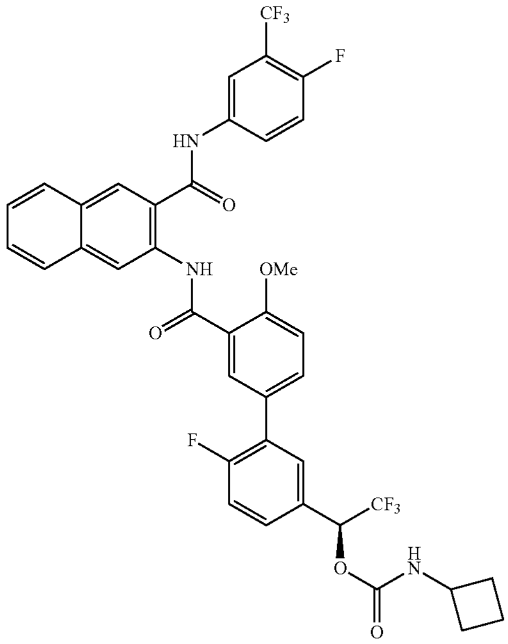 [SMILES: COc1ccc(-c2cc([C@H](OC(=O)NC3CCC3)C(F)(F)F)ccc2F)cc1C(=O)Nc1cc2ccccc2cc1C(=O)Nc1ccc(F)c(C(F)(F)F)c1]

Example 5 (0.6 mg, 0.7 μmol, 2% yield) was prepared from intermediate 7-1 (10 mg, 0.029 mmol), intermediate 12-3 (12.67 mg, 0.029 mmol), and 1-methyl-1H-imidazole (2.36 mg, 0.029 mmol) in ACN (I mL), followed by TCFH (8.06 mg, 0.029 mmol). After 12 h. the reaction mixture was purified by reverse phase HPLC (using gradients of Mobile Phase A: 5:95 ACN:water with 10 mM ammonium acetate; Mobile Phase B: 95:5 ACN:water with 10 mM ammonium acetate) to give a solid. $^1$H NMR (500 MHz, DMSO-d6) δ 9.11 (s, 1H), 8.90-8.53 (m, 1H), 8.48 (s, 1H), 8.40 (br d, J=4.3 Hz, 1H), 8.26 (br s, 1H), 8.17 (br d, J=7.9 Hz, 1H), 8.14-8.09 (m, 1H), 8.04 (br d, J=8.2 Hz, 1H), 7.97 (br d, J=7.9 Hz, 1H), 7.79 (br d, J=8.5 Hz, 1H), 7.74 (br d, J=7.0 Hz, 1H), 7.69-7.63 (m, 1H), 7.61-7.53 (m, 2H), 7.47 (br d, J=10.7 Hz, 1H), 7.41 (d, J=8.5 Hz, 1H), 7.33-6.91 (m, 1H), 6.39 (q, J=6.8 Hz, 1H), 4.08 (s, 3H), 3.98-3.88 (m, 1H), 2.55 (s, 1H), 2.24-2.05 (m, 1H), 1.92 (dt, J=18.5.9.2 Hz, 1H), 1.75 (s, 1H), 1.63-1.49 (m, 1H), 1.24 (br s, 1H). Analytical LC-MS: RT=2.96 min; MS (ESI) m/z=772.3 (M+H);$^+$ HPLC purity 90%; [Method B].

Example-6

3'-((8-bromo-3-((4-fluoro-3-(trifluoromethyl)phenyl) carbamoyl)naphthalen-2-yl)carbamoyl)-6-fluoro-4'-methoxy-[1,1'-biphenyl]-3-carboxylic acid

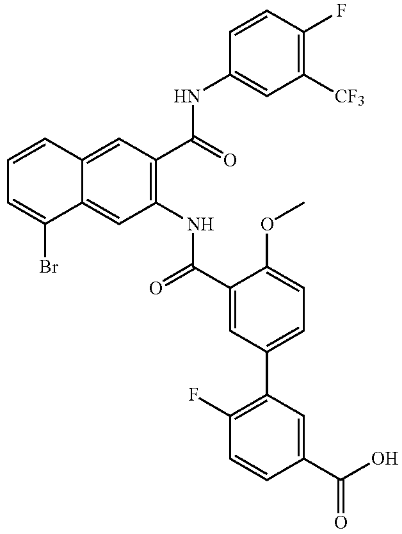 [SMILES: COc1ccc(-c2cc(C(=O)O)ccc2F)cc1C(=O)Nc1cc2c(Br)cccc2cc1C(=O)Nc1ccc(F)c(C(F)(F)F)c1]

Example 6 was prepared (3 mg, 5 μmol, 24% yield) in a similar manner as example 1 replacing intermediate 1-1 with intermediate 9-1 (8 mg, 1.9 μmol). $^1$H NMR (500 MHz, DMSO-d6) δ 11.72 (s, 11H), 11.24 (br s, 1H), 9.53 (s, 1H), 8.54 (s, 1H), 8.45-8.36 (m, 1H), 8.31 (d, J=0.6 Hz, 1H), 8.18-8.05 (m, 3H), 8.04-7.94 (m, 2H), 7.90-7.78 (m, 1H), 7.60 (t, J=9.9 Hz, 11H), 7.52-7.42 (m, 2H), 7.40 (d, J=8.9 Hz, 1H), 4.09 (s, 3H). Analytical LC-MS: RT=2.2 min; MS (ESI) m/z=699 (M+H);$^+$ HPLC purity 100%; [Method B].

Example 8

3'-((6-bromo-3-((4-fluoro-3-(trifluoromethyl)phenyl) carbamoyl)naphthalen-2-yl)carbamoyl)-6-fluoro-4'-methoxy-[1,1'-biphenyl]-3-carboxylic acid

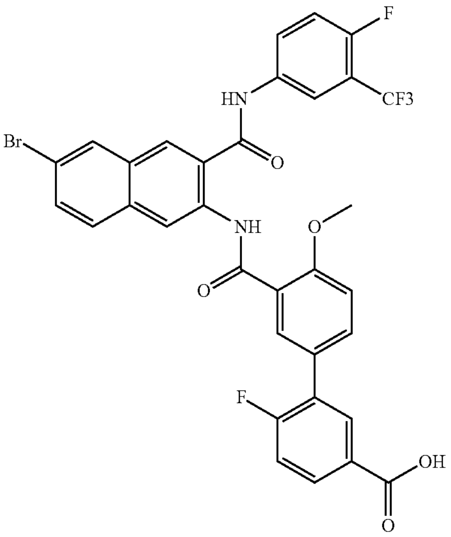 [SMILES: COc1ccc(-c2cc(C(=O)O)ccc2F)cc1C(=O)Nc1cc2ccc(Br)cc2cc1C(=O)Nc1ccc(F)c(C(F)(F)F)c1]

Example 8 (10 mg, 1.4 μmol, 27% yield) was prepared in a similar manner as example 5 replacing intermediate 12-3 with intermediate 13-5 and subsequent hydrolysis of the !-butyl ester with TFA/DCM. $^1$H NMR (500 MHz, DMSO-$d_6$) δ 11.53 (s, 1H), 11.17 (s, 1H), 9.05 (br s, 1H), 8.47-8.33 (m, 2H), 8.26 (br s, 2H), 8.12-8.03 (m, 2H), 8.02-7.95 (m, 1H), 7.91 (br d, J=8.8 Hz, 1H), 7.80 (br d, J=8.1 Hz, 1H), 7.72 (br d, J=8.8 Hz, 1H), 7.57 (br t, J=9.7 Hz, 1H), 7.45 (br t, J=8.5 Hz, 1H), 7.36 (br d, J=8.5 Hz, 1H), 4.05 (s, 3H), 3.63-3.49 (m, 1H). Analytical LC-MS: RT=2.29 min; MS (ESI) m/z=699.3 (M+H);$^+$ HPLC purity 100%; [Method B].

Example 9

N-(4-fluoro-3-(trifluoromethyl)phenyl)-3-(5-((3-hydroxypropyl)sulfonyl)-2-methoxybenzamido)-2-naphthamide

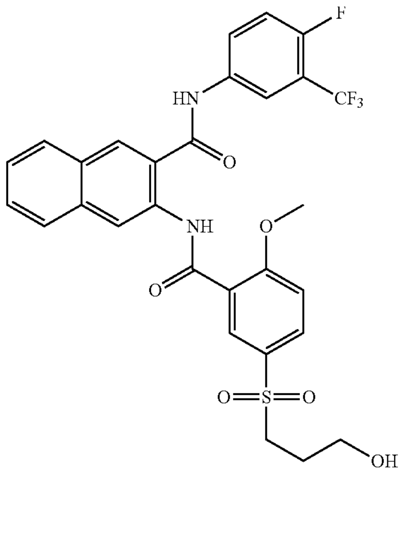 [SMILES: COc1ccc(S(=O)(=O)CCCO)cc1C(=O)Nc1cc2ccccc2cc1C(=O)Nc1ccc(F)c(C(F)(F)F)c1]

Example 9 (2.8 mg, 0.004 mmol, 32% yield) was prepared in a similar manner as Example 5 replacing intermediate 12-3 with intermediate 14-3. $^1$H NMR (500 MHz, DMSO-d6) δ 11.62 (s, 1H), 11.15 (s, 1H), 9.08-9.04 (m, 1H), 8.72-8.67 (m, 1H), 8.54-8.46 (m, 2H), 8.40-8.35 (m, 1H), 8.14-7.96 (m, 4H), 7.65 (t, J=7.5 Hz, 1H), 7.62-7.56 (m, 2H), 7.51 (d, J=8.9 Hz, 1H), 4.68-4.63 (m, 1H), 4.13 (s, 3H), 2.54 (s, 2H), 1.72-1.65 (m, 2H). Analytical LC-MS: RT=2.14 min; MS (ESI) m/z=605.1 (M+H);$^+$ HPLC purity 99%; [Method C].

Example 10

(S)—N-(4-fluoro-3-(trifluoromethyl)phenyl)-3-(5-(3-hydroxybut-1-yn-1-yl)-2-methoxybenzamido)-2-naphthamide

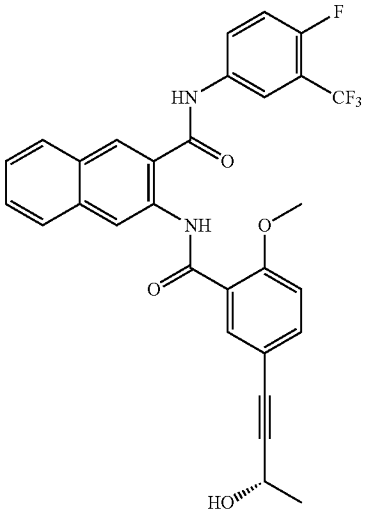 [SMILES: COc1ccc(C#C[C@H](C)O)cc1C(=O)Nc1cc2ccccc2cc1C(=O)Nc1ccc(F)c(C(F)(F)F)c1]

Example 10 (2.4 mg, 0.004 mmol, 30% yield) was prepared in a similar manner as Example 5 replacing intermediate 12-3 with intermediate 15-2. $^1$H NMR (500 MHz, DMSO-d6) δ 11.52 (s, 1H), 11.15-11.11 (m, 1H), 9.04 (s, 1H), 8.43 (s, 1H), 8.38-8.35 (m, 1H), 8.10 (br dd, J=7.2, 2.3 Hz, 1H), 8.07-8.00 (m, 2H), 7.96 (d, J=7.9 Hz, 1H), 7.67-7.54 (m, 4H), 7.24 (d, J=8.9 Hz, 1H), 4.59 (quin, J=6.2 Hz, 1H), 4.02 (s, 3H), 1.39 (d, J=6.4 Hz, 3H). Analytical LC-MS: RT=2.39 min; MS (ESI) m/z=551.1 (M+H);$^+$ HPLC purity 100%; [Method C].

Example 11

3-(5-(1,1-dioxidoisothiazolidin-2-yl)-2-methoxybenzamido)-N-(4-fluoro-3-(trifluoromethyl)-phenyl)-2-naphthamide

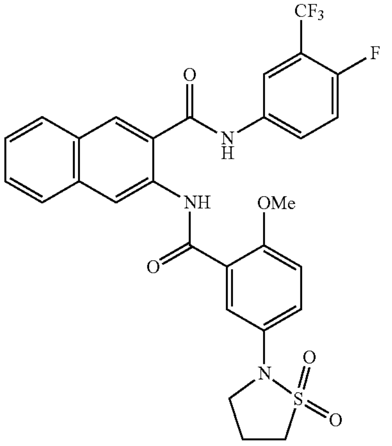 [SMILES: COc1ccc(N2CCCS2(=O)=O)cc1C(=O)Nc1cc2ccccc2cc1C(=O)Nc1ccc(F)c(C(F)(F)F)c1]

Example 11 (4 mg, 6 μmol, 10% yield) was prepared in a manner similar to Example 5 from intermediate 16-2. $^1$H NMR (500 MHz, DMSO-d6) δ 11.59 (s, 1H), 11.24-10.91 (m, 11H), 9.10 (s, 1H), 8.62-8.33 (m, 2H), 8.18-8.08 (m, 1H), 8.04 (d, J=8.2 Hz, 1H), 8.00 (d, J=3.1 Hz, 1H), 7.97 (d, J=8.5 Hz, 1H), 7.66 (t, J=7.2 Hz, 1H), 7.62-7.55 (m, 2H), 7.44 (dd, J=8.9, 3.1 Hz, 1H), 7.30 (d, J=9.2 Hz, 1H), 4.02 (s, 3H), 3.76 (t, J=6.6 Hz, 2H), 3.58-3.40 (m, 1H), 2.43 (quin, J=6.9 Hz, 2H); Analytical LC-MS: RT=2.44 min; MS (ESI) m/z=602.3 (M+H);$^+$ HPLC purity 92%; [Method B].

Example 12

N-(4-fluoro-3-(trifluoromethyl)phenyl)-3-(2-methoxy-5-(6-oxopyridazin-1(6H)-yl)benzamido)-2-naphthamide

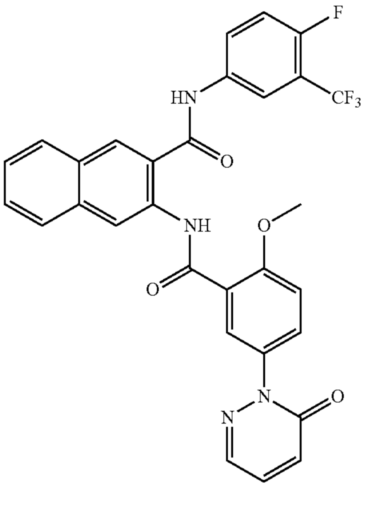 [SMILES: COc1ccc(-n2ncccc2=O)cc1C(=O)Nc1cc2ccccc2cc1C(=O)Nc1ccc(F)c(C(F)(F)F)c1]

Example 12 (5.6 mg, 10 μmol, 68% yield) was prepared in a manner similar to Example 5 from intermediate 11-2. $^1$H NMR (500 MHz, DMSO-d6) δ 11.60 (s, 1H), 11.14 (s, 1H), 9.05 (s, 1H), 8.46-8.43 (m, 1H), 8.40-8.37 (m, 1H), 8.23 (d, J=2.7 Hz, 1H), 8.14-8.06 (m, 2H), 8.06-8.00 (m, 1H), 7.95 (d, J=8.2 Hz, 1H), 7.81-7.75 (m, 1H), 7.67-7.54 (m, 3H), 7.50 (dd, J=9.5, 3.7 Hz, 1H), 7.39-7.33 (m, 1H), 7.09 (dd, J=9.5, 1.2 Hz, 1H), 4.07 (s, 3H). Analytical LC-MS: RT=2.24 min; MS (ESI) m/z=577.1 (M+H);+ HPLC purity 99%; [Method C].

Example 13

N-(4-fluoro-3-(trifluoromethyl)phenyl)-3-(5-(5-(hydroxymethyl)-3a,5,6,6a-tetrahydro-4H-cyclopenta[d]isoxazol-3-yl)-2-methoxybenzamido)-2-naphthamide. (Homochiral, Peak 4)

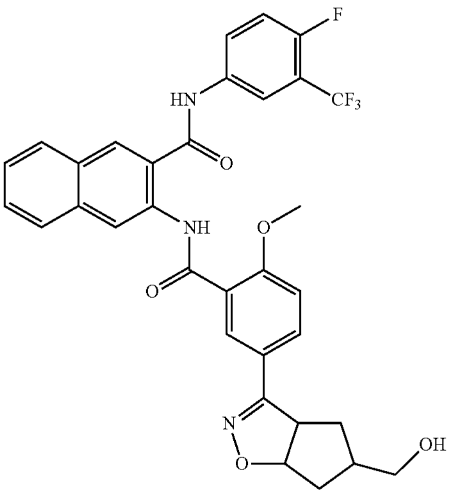 [SMILES: COc1ccc(C2=NOC3CC(CO)CC23)cc1C(=O)Nc1cc2ccccc2cc1C(=O)Nc1ccc(F)c(C(F)(F)F)c1]

Example 13 (6.2 mg, 0.009 mmol, 32% yield) was prepared in a manner similar to Example 5 from intermediate 6-10. $^1$H NMR (500 MHz, DMSO-d6) δ 11.57 (s, 1H), 11.14 (s, 1H), 9.09 (s, 1H), 8.45 (s, 1H), 8.40-8.35 (m, 2H), 8.13-8.09 (m, 1H), 8.03 (br d, J=7.9 Hz, 1H), 7.96 (br d, J=8.2 Hz, 1H), 7.87 (dd, J=8.5, 2.1 Hz, 1H), 7.66-7.55 (m, 3H), 7.33 (d, J=8.5 Hz, 1H), 5.19-5.14 (m, 1H), 4.17-4.11 (m, 1H), 4.06 (s, 3H), 2.27-2.11 (m, 3H), 1.68-1.62 (m, 1H), 1.50 (dt, J=12.8, 6.1 Hz, 1H). Analytical LC-MS: RT=2.35 min; MS (ESI) m/z=622.3 (M+H);+ HPLC purity 100%; [Method C].

Example 14

N-(4-fluoro-3-(trifluoromethyl)phenyl)-3-(5-(5-(hydroxymethyl)-3a,5,6,6a-tetrahydro-4H-cyclopenta[d]isoxazol-3-yl)-2-methoxybenzamido)-2-naphthamide. (Homochiral, Peak 3)

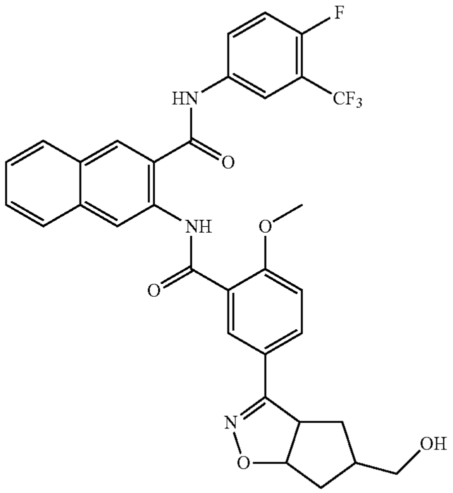 [SMILES: COc1ccc(C2=NOC3CC(CO)CC23)cc1C(=O)Nc1cc2ccccc2cc1C(=O)Nc1ccc(F)c(C(F)(F)F)c1]

Example 14 (6.6 mg, 0.01 mmol, 25% yield) was prepared in a manner similar to Example 5 from intermediate 6-8. $^1$H NMR (500 MHz, DMSO-d6) δ 11.57 (s, 1H), 11.14 (s, 1H), 9.09 (s, 1H), 8.47-8.44 (m, 1H), 8.41-8.34 (m, 2H), 8.14-8.10 (m, 1H), 8.03 (br d, J=7.9 Hz, 1H), 7.96 (br d, J=8.2 Hz, 1H), 7.87 (dd, J=8.5, 1.8 Hz, 1H), 7.94 (br s, 1H), 7.66-7.53 (m, 3H), 7.33 (d, J=8.9 Hz, 1H), 5.14 (br dd, J=8.7, 5.0 Hz, 1H), 4.53-4.47 (m, 1H), 4.23 (br t, J=8.7 Hz, 1H), 4.06 (s, 3H), 2.02-1.79 (m, 3H), 1.73-1.65 (m, 1H), 1.61-1.53 (m, 1H). Analytical LC-MS: RT=2.35 min; MS (ESI) m/z=622.3 (M+H);+ HPLC purity 95%; [Method C].

Example 15

N-(4-fluoro-3-(trifluoromethyl)phenyl)-3-(5-(5-hydroxy-3a,5,6,6a-tetrahydro-4H-cyclopenta[d]isoxazol-3-yl)-2-methoxybenzamido)-2-naphthamide. (Homochiral, Peak 1)

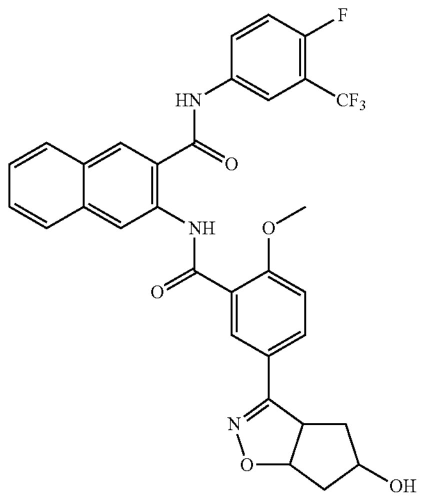 [SMILES: COc1ccc(C2=NOC3CC(O)CC23)cc1C(=O)Nc1cc2ccccc2cc1C(=O)Nc1ccc(F)c(C(F)(F)F)c1]

Example 15 (5.5 mg, 9.05 μmol, 21% yield) was prepared in a manner similar to Example 5 from intermediate 5-3. $^1$H NMR (400 MHz, DMSO-d6) δ 11.57 (s, 1H)), 11.14 (s, 1H), 9.09 (s, 1H), 8.45 (s, 1H), 8.38 (dd, J=6.6, 2.4 Hz, 1H), 8.36-8.34 (m, 11H), 8.15-8.09 (m, 1H), 8.03 (d, J=8.1 Hz, 1H), 7.97 (d, J=8.1 Hz, 1H), 7.86 (dd, J=8.7, 2.3 Hz, 1H), 7.67-7.54 (m, 3H), 7.33 (d, J=8.8 Hz, 1H), 5.16 (ddd, J=9.4, 6.1, 2.9 Hz, 1H), 4.25 (td, J=9.4, 4.2 Hz, 1H), 4.11 (quin, J=6.2 Hz, 1H), 4.06 (s, 3H), 2.03-1.88 (m, 3H), 1.83 (dt, J=12.7, 4.8 Hz, 1H). Analytical LC-MS: 1.02 min; MS (ESI) m, z=608.1 (M+H);$^+$ HPLC purity 100%; [Method A].

Example 16

N-(4-fluoro-3-(trifluoromethyl)phenyl)-3-(5-(5-hydroxy-3a,5,6,6a-tetrahydro-4H-cyclopenta[d]isoxazol-3-yl)-2-methoxybenzamido)-2-naphthamide. (Homochiral, Peak 4)

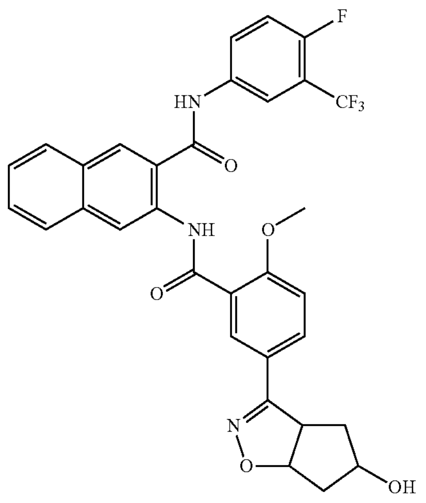 [SMILES: COc1ccc(C2=NOC3CC(O)CC23)cc1C(=O)Nc1cc2ccccc2cc1C(=O)Nc1ccc(F)c(C(F)(F)F)c1]

Example 16 (8.4 mg, 0.013 mmol, 32% yield) was prepared in a manner similar to Example 5 from intermediate 5-6. H NMR (500 MHz, DMSO-d6) δ 11.57 (s, 1H), 11.16-11.12 (m, 1H), 9.08 (s, 1H), 8.44 (s, 1H), 8.40-8.33 (m, 2H), 8.14-8.09 (m, 1H), 8.02 (br d, J=7.6 Hz, 1H), 7.96 (br d, J=7.9 Hz, 1H), 7.87-7.82 (m, 1H), 7.64 (br t, J=7.6 Hz, 1H), 7.61-7.53 (m, 2H), 7.32 (d, J=8.9 Hz, 1H), 5.15-5.09 (m, 1H), 4.18-4.10 (m, 2H), 4.05 (s, 3H), 2.15-2.06 (m, 2H), 1.93-1.88 (m, 1H), 1.80-1.74 (m, 1H). Analytical LC-MS: RT=2.27 min; MS (ESI) m/z=607.96 (M+H);$^+$ HPLC purity 100%; [Method B].

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (III):

(III)

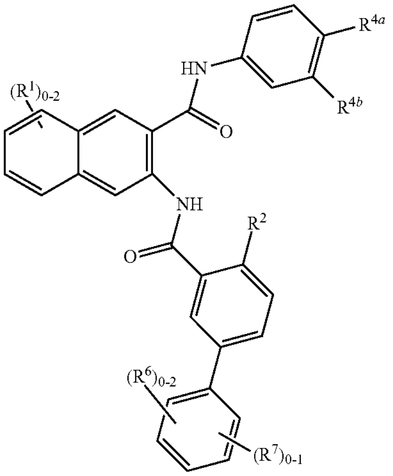

or a pharmaceutically acceptable salt thereof, wherein:

$R^1$ is Br or $CF_3$;

$R^2$ is —$OC_{1-4}$ alkyl substituted with 0-4 halo;

$R^{4a}$ is halo;

$R^{4b}$ is $C_{1-3}$ alkyl substituted with 0-4 F;

$R^6$ is halo, CN, $C_{1-3}$ alkyl, —OH, or —$OC_{1-4}$ alkyl;

$R^7$ is $C_{1-2}$ alkyl substituted with 0-1 $R^8$ and 0-1 $R^9$, $OR^b$, —$NR^aR^a$, —$NR^aC({=}O)R^b$, —$NR^aC({=}O)NR^aR^a$, —$NR^aS({=}O)_pR^c$, —$C({=}O)R^b$, —$C({=}O)OR^b$, —$C({=}O)NR^dR^a$, —$C({=}O)NR^aS({=}O)_pR^c$, —$OC({=}O)R^b$, —$S({=}O)_pR^c$, —$S({=}O)_pNR^aR^a$, or $C_{3-6}$ cycloalkyl;

$R^8$ is halo, —$C({=}O)OR^b$, —$C({=}O)NHR^a$, or $C_{1-3}$ alkyl substituted with 0-3 halo or OH;

$R^9$ is —$OR^b$, —$NR^aR^a$, —$NR^aC({=}O)R^b$, —$NR^aC({=}O)OR^b$, —$NR^aS({=}O)_pR^c$, —$OC({=}O)NR^aR^a$, —$OC({=}O)NR^aOR^b$, —$S({=}O)_pNR^aR^a$, or —$S(O)_pR^c$;

$R^a$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, —$(CH_2)_n$—$C_{3-10}$ carbocyclyl substituted with 0-4 $R^e$, or —$(CH_2)_n$-heterocyclyl substituted with 0-4 $R^e$; or $R^a$ and $R^a$ together with the nitrogen atom to which they are both attached form a heterocyclyl substituted with 0-4 $R^e$;

$R^b$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, —$(CH_2)_n$—$C_{3-10}$ carbocyclyl substituted with 0-4 $R^e$, or —$(CH_2)_n$-heterocyclyl substituted with 0-4 $R^e$;

$R^c$ is $C_{1-5}$ alkyl substituted with 0-4 $R^e$, $C_{2-3}$ alkenyl substituted with 0-4 $R^e$, $C_{2-5}$ alkynl substituted with 0-4 $R^e$, $C_{3-6}$ carbocyclyl, or heterocyclyl;

$R^d$ is H or $C_{1-2}$ alkyl;

$R^e$ is halo, CN, =O, $C_{1-5}$ alkyl substituted with 0-5 $R^g$, $C_{2-6}$ alkenyl substituted with 0-5 $R^g$, $C_{2-6}$ alkynyl substituted with 0-5 $R^g$, —$(CH_2)_n$—$C_{3-6}$ cycloalkyl, —$(CH_2)_n$-aryl, —$(CH_2)_n$-heterocyclyl, —$(CH_2)_nOR^f$, $S({=}O)_pR^f$, $C({=}O)NR^fR^f$, $C({=}O)OR^f$, $NR^fC({=}O)R^f$, $S({=}O)_pNR^fR^f$, $NR^fS({=}O)_pR^f$, $NR^fC({=}O)OR^f$, $OC({=}O)NR^fR^f$, or —$(CH_2)_nNR^fR^f$;

$R^f$ is H, $C_{1-6}$ alkyl, $C_{3-6}$ cycloalkyl, or aryl; or $R^f$ and $R^f$ together with the nitrogen atom to which they are both attached form a heterocyclyl;

$R^g$ is halo, CN, —OH, $C_{1-6}$alkyl, $C_{3-6}$ cycloalkyl, or aryl;

n is zero, 1, 2, or 3; and p is zero, 1, or 2.

2. The compound of claim 1, having Formula (IV):

(IV)

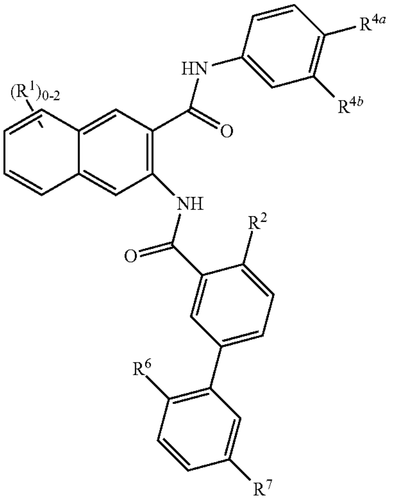

or a pharmaceutically acceptable salt thereof, wherein:

$R^1$ is Br;

$R^2$ is —$OC_{1-3}$ alkyl;

$R^{4a}$ is F;

$R^{4b}$ is $CF_3$;

$R^6$ is halo;

$R^7$ is $C_{1-2}$ alkyl substituted with 0-1 $R^8$ and 0-1 $R^9$, —$C({=}O)OR^b$, or —$C({=}O)NR^aR^a$;

$R^8$ is —$C({=}O)OR^b$, —$C({=}O)NHR^a$, or $C_{1-3}$ alkyl substituted with 0-3 halo or OH;

$R^9$ is —$OR^b$, —$NR^aR^a$, —$NR^aC({=}O)R^b$, or —$OC({=}O)NR^aR^a$;

$R^a$ is H, $C_{1-4}$ alkyl substituted with 0-3 $R^e$, —$(CH_2)_n$—$C_{3-6}$ cycloalkyl substituted with 0-3 $R^e$, phenyl substituted with 0-3 $R^e$;

$R^b$ is H or heterocyclyl substituted with 0-3 $R^e$;

$R^c$ is halo, CN, =O, or $C_{1-6}$ alkyl; and n is zero or 1.

3. A compound of formula (V):

(V)

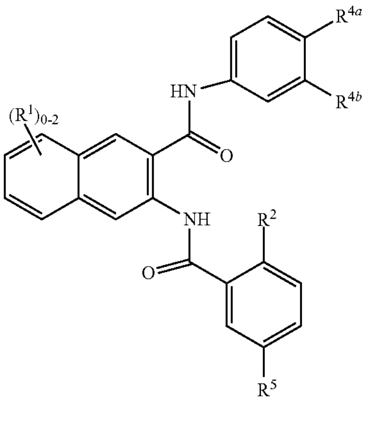

or a pharmaceutically acceptable salt thereof, wherein:

$R^1$ is halo or $C_{1-3}$ alkyl substituted with 0-5 halo;

$R^2$ is —$OC_{1-4}$ alkyl substituted with 0-4 halo;

$R^{4a}$ is halo;

$R^{4b}$ is $C_{1-3}$ alkyl substituted with 0-4 halo;

$R^5$ is a 3- to 12-membered heterocyclyl comprising 1-4 heteroatoms selected from O, S(═O)$_p$, N and $NR^{10}$ substituted with 0-3 $R^6$ and 0-1 $R^7$;

$R^6$ is halo, ═O, —OH, —$OC_{1-4}$ alkyl, or $C_{1-4}$ alkyl substituted with 0-2 halo or OH;

$R^7$ is $C_{1-2}$ alkyl substituted with 0-1 $R^8$ and 0-1 $R^9$, —$OR^b$, —$NR^aR^a$, —$NR^aC$(═O)$R^b$, —$NR^aC$(═O)$OR^b$, —$NR^aC$(═O)$NR^aR^a$, —$NR^aS$(═O)$_pR^c$, —C(═O)$R^b$, —C(═O)$OR^b$, —C(═O)$NR^aR^a$, —C(═O)$NR^aS$(═O)$_pR^c$, —OC(═O)$R^b$, —S(═O)$_pR^c$, —S(═O)$_pNR^aR^a$, $C_{3-6}$ cycloalkyl, or a 4- to 6-membered heterocyclyl comprising 1-4 heteroatoms selected from O, S(═O)$_p$, N and $NR^d$, and substituted with 0-4 $R^e$;

$R^8$ is —C(═O)$OR^b$, —C(═O)$NHR^a$, —C(═O)$NHOR^b$, or $C_{1-4}$ alkyl substituted with 0-3 halo or OH;

$R^9$ is —$OR^b$, —$NR^aR^a$, —$NR^aC$(═O)$R^b$, —$NR^aC$(═O)$OR^b$, —$NR^aS$(═O)$_pR^c$, —$NR^aS$(O)$_pNR^aR^a$, —OC(═O)$NR^aR^a$, —S(═O)$_pNR^aR^a$, or —S(O)$_pR^c$;

$R^{10}$ is H, $C_{1-4}$ alkyl substituted with 0-2 $R^{11}$, —C(═O)$R^b$, —C(═O)$OR^b$, —C(═O)$NR^aR^a$, $C_{3-6}$ cycloalkyl substituted with 0-5 $R^e$, or a 4- to 6-membered heterocyclyl comprising 1-4 heteroatoms selected from O, S(═O)$_p$, N and $NR^{12}$, and substituted with 0-5 $R^e$;

$R^{11}$ is —OH, —C(═O)OH, or aryl;

$R^{12}$ is H, $C_{1-3}$ alkyl, or aryl;

$R^a$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, —$(CH_2)_n$—$C_{3-10}$ carbocyclyl substituted with 0-4 $R^e$, or —$(CH_2)_n$-heterocyclyl substituted with 0-4 $R^e$; or $R^a$ and $R^a$ together with the nitrogen atom to which they are both attached form a heterocyclyl substituted with 0-4 $R^e$;

$R^b$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, —$(CH_2)_n$—$C_{3-10}$carbocyclyl substituted with 0-4 $R^e$, or —$(CH_2)_n$-heterocyclyl substituted with 0-4 $R^e$:

$R^c$ is $C_{1-5}$ alkyl substituted with 0-4 $R^e$, $C_{2-5}$ alkenyl substituted with 0-4 $R^e$, $C_{2-5}$ alkynyl substituted with 0-4 $R^e$, $C_{3-6}$ carbocyclyl, or heterocyclyl;

$R^d$ is H or $C_{1-3}$ alkyl;

$R^e$ is halo, CN, ═O, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, —$(CH_2)_n$—$C_{3-6}$ cycloalkyl, —$(CH_2)_n$-aryl, —$(CH_2)_n$-heterocyclyl, —$(CH_2)_nOR^f$, or —C(═O)$OR^f$;

$R^f$ is H or $C_{1-3}$ alkyl;

$R^g$ is halo, CN, OH, $C_{1-6}$ alkyl, $C_{3-6}$ cycloalkyl, or aryl;

n is zero, 1, 2, or 3; and p is zero, 1, or 2.

4. The compound of claim 3, or a pharmaceutically acceptable salt thereof, wherein:

$R^2$ is —$OCH_3$;

$R^{4a}$ is F;

$R^{4b}$ is $CF_3$;

$R^5$ is

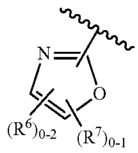
,
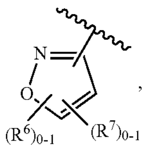
,
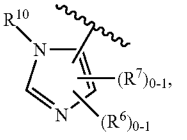
or
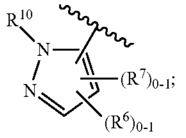

$R^6$ is halo, —OH, or $C_{1-4}$ alkyl substituted with 0-1 OH;

$R^7$ is $C_{1-2}$ alkyl substituted with 0-1 $R^8$ and 0-1 $R^9$;

$R^8$ is —C(═O)$OR^b$, —C(═O)$NHR^1$, or —C(═O)$NHOR^b$;

$R^9$ is —$OR^b$ or —$NR^aR^a$;

$R^{10}$ is H or $C_{1-3}$ alkyl;

$R^a$ is H or $C_{1-6}$ alkyl; and $R^b$ is H or $C_{1-6}$ alkyl.

5. The compound of claim 3, or pharmaceutically acceptable salt thereof, wherein:

$R^2$ is —$OCH_3$;

$R^{4a}$ is F;

$R^{4b}$ is $CF_3$;

$R^5$ is

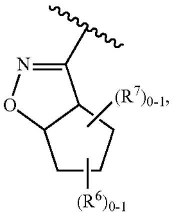
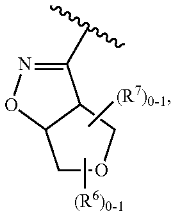
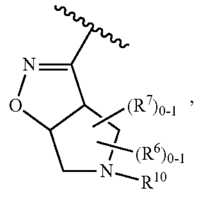
,
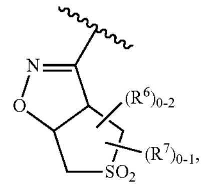
or
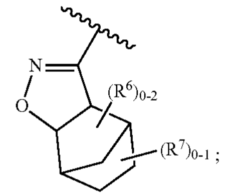

$R^6$ is halo, $C_{1-4}$ alkyl, —OH, or —$C_{1-4}$ alkyl;

$R^7$ is $C_{1-4}$ alkyl substituted with 0-1 $R^8$ and 0-1 $R^9$;

$R^8$ is —C(═O)$OR^b$;

$R^9$ is OH;

$R^{10}$ is H or $C_{1-3}$ alkyl; and $R^b$ is H or $C_{1-4}$ alkyl.

6. The compound of claim 3, or a pharmaceutically acceptable salt thereof, wherein:

$R^2$ is —$OCH_3$;

$R^{4a}$ is F;

$R^{4b}$ is $CF_3$;

$R^5$ is

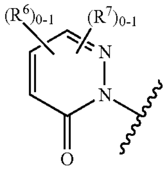, 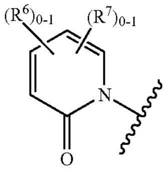, 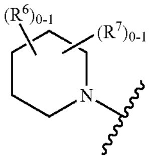,

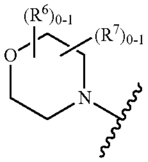, 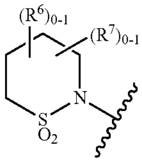, 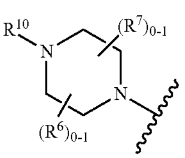,

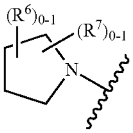, 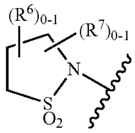, or 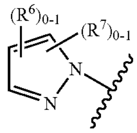;

$R^6$ is halo, CN, $C_{1-4}$ alkyl, $=$O, —OH, or —$OC_{1-4}$ alkyl;

$R^7$ is $C_{1-2}$ alkyl substituted with 0-1 $R^8$ and 0-1 $R^9$, —$NR^aR^a$, —$NR^aC(=O)R^b$, —$NR^aC(=O)OR^b$, or —$C(=O)OR^b$;

$R^8$ is —$C(=O)OR^b$, —$C(=O)NHR^a$, —$C(=O)NHOR^b$, or $C_{1-4}$ alkyl substituted with 0-3 halo or OH;

$R^9$ is —$NR^aC(=O)R^b$;

$R^{10}$ is H or $C_{1-3}$ alkyl;

$R^a$ is H or $C_{1-4}$ alkyl; and $R^b$ is H, or $C_{1-4}$ alkyl.

7. A compound of formula (VI):

(VI)

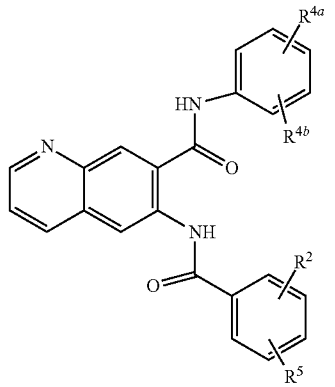

or a pharmaceutically acceptable salt thereof, wherein:

$R^2$ is —$OC_{1-3}$ alkyl;

$R^{4a}$ is halo;

$R^{4b}$ is $C_{1-4}$ alkyl substituted with 0-4 halo;

$R^5$ is $C_6$ aryl substituted with 0-3 $R^6$ and 0-2 $R^7$, or a 3- to 12-membered heterocyclyl comprising 1-4 heteroatoms selected from O, $S(=O)_p$, N and $NR^{10}$ substituted with 0-3 $R^6$ and 0-1 $R^7$;

$R^6$ is halo, $=$O, —OH, —$OC_{1-4}$ alkyl, or $C_{1-4}$ alkyl substituted with 0-2 halo or OH;

$R^7$ is $C_{1-3}$ alkyl substituted with 0-1 $R^8$ and 0-1 $R^9$, —$OR^b$, —$NR^aR^a$, —$NR^aC(=O)R^b$, —$NR^aC(=O)OR^b$, —$NR^aC(=O)NR^aR^a$, —$NR^3S(=O)_pR^c$, —$C(=O)R^b$, —$C(=O)OR^b$, —$C(=O)NR^aR^a$, —$C(=O)NR^aS(=O)_pR^c$, —$OC(=O)R^b$, —$S(=O)_pR^c$, —$S(=O)_pNR^aR^a$, $C_{3-6}$ cycloalkyl, or a 4- to 6-membered heterocyclyl comprising 1-4 heteroatoms selected from O, $S(=O)_p$, N and $NR^d$, and substituted with 0-5 $R^c$;

$R^8$ is halo, —$C(=O)OR^b$, —$C(=O)NHR^a$, —$C(=O)NHOR^b$, or $C_{1-4}$ alkyl substituted with 0-3 halo or OH;

$R^9$ is —$OR^b$, —$NR^aR^a$, —$NR^aC(=O)R^b$, —$NR^aC(=O)OR^b$, —$NR^aS(=O)_pR^c$, —$NR^aS(O)_pNR^aR^a$, —$OC(=O)NR^aR^a$, —$OC(=O)NR^aOR^b$, —$S(=O)_pNR^aR^a$, or —$S(O)_pR^c$;

$R^{10}$ is H, $C_{1-4}$ alkyl substituted with 0-2 $R^{11}$, —$C(=O)R^b$, —$C(=O)OR^b$, —$C(=O)NR^aR^a$, $C_{3-6}$ cycloalkyl substituted with 0-5 $R^e$, or a 4- to 6-membered heterocyclyl comprising 1-4 heteroatoms selected from O, $S(=O)_p$, N and $NR^2$, and substituted with 0-5 $R^e$, $R^{11}$ is —OH, —C(=O)OH, or aryl;

$R^{12}$ is H, $C_{1-3}$ alkyl, or aryl;

$R^a$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, —$(CH_2)_n$—$C_{3-10}$ carbocyclyl substituted with 0-5 $R^e$, or —$(CH_2)_n$-heterocyclyl substituted with 0-5 $R^e$; or $R^a$ and $R^a$ together with the nitrogen atom to which they are both attached form a heterocyclyl substituted with 0-5 $R^e$;

$R^b$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, —$(CH_2)_n$—$C_{3-10}$carbocyclyl substituted with 0-5 $R^e$, or —$(CH_2)_n$-heterocyclyl substituted with 0-5 $R^e$;

$R^c$ is $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $C_{3-6}$ carbocyclyl, or heterocyclyl;

$R^d$ is H or $C_{1-4}$ alkyl;

$R^e$ is halo, CN, $=$O, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, —$(CH_2)_n$—$C_{1-6}$ cycloalkyl, —$(CH_2)_n$-aryl, —$(CH_2)_n$-heterocyclyl, —$(CH_2)_nOR^f$, or —$C(=O)OR^f$;

$R^f$ is H or $C_{1-3}$ alkyl;

$R^g$ is halo, CN, OH, $C_{1-6}$alkyl, $C_{3-6}$ cycloalkyl, or aryl;

n is zero, 1, 2, or 3; and p is zero, 1, or 2.

8. A compound of formula (VII):

(VII)

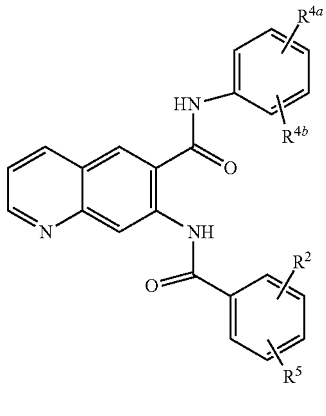

or a pharmaceutically acceptable salt thereof, wherein:

$R^2$ is $—OC_{1-3}$ alkyl;

$R^{4a}$ is halo;

$R^{4b}$ is $C_{1-4}$ alkyl substituted with 0-4 halo;

$R^5$ is $C_6$ aryl substituted with 0-3 $R^6$ and 0-2 $R^7$, or a 3- to 12-membered heterocyclyl comprising 1-4 heteroatoms selected from O, $S(=O)_p$, N and $NR^{10}$ substituted with 0-3 $R^6$ and 0-1 $R^7$;

$R^6$ is halo, =O, —OH, $—OC_{1-4}$ alkyl, or $C_{1-4}$ alkyl substituted with 0-2 halo or OH;

$R^7$ is $C_{1-3}$ alkyl substituted with 0-1 $R^8$ and 0-1 $R^9$, $—OR^b$, $—NR^aR^a$, $—NR^aC(=O)R^b$, $—NR^aC(=O)OR^b$, $—NR^aC(=O)NR^aR^a$, $—NR^aS(=O)_pR^c$, $—C(=O)R^b$, $—C(=O)OR^b$, $—C(=O)NR^aR^a$, $—C(=O)NR^aS(=O)_pR^c$, $—OC(=O)R^b$, $—S(=O)_pR^c$, $—S(=O)NR^aR^a$, $C_{3-6}$ cycloalkyl, or a 4- to 6-membered heterocyclyl comprising 1-4 heteroatoms selected from O, $S(=O)_p$, N and $NR^d$, and substituted with 0-5 $R^c$;

$R^8$ is halo, $—C(=O)OR^b$, $—C(=O)NHR^a$, $—C(=O)NHOR^b$, or $C_{1-4}$ alkyl substituted with 0-3 halo or OH;

$R^9$ is $—OR^b$, $—NR^aR^a$, $—NR^aC(=O)R^b$, $—NR^aC(=O)OR^b$, $—NR^aS(=O)_pR^c$, $—NR^aS(O)_pNR^aR^a$, $—OC(=O)NR^aR^a$, $—OC(=O)NR^aOR^b$, $—S(=O)_pNR^aR^a$, or $—S(O)_pR^c$;

$R^{10}$ is H, $C_{1-4}$ alkyl substituted with 0-2 $R^{11}$, $—C(=O)R^b$, $—C(=O)OR^b$, $—C(=O)NR^aR^a$, $C_{3-6}$ cycloalkyl substituted with 0-5 $R^e$, or a 4- to 6-membered heterocyclyl comprising 1-4 heteroatoms selected from O, $S(=O)_p$, N and $NR^{12}$, and substituted with 0-5 $R^e$;

$R^{11}$ is —OH, —C(=O)OH, or aryl;

$R^{12}$ is H, $C_{1-3}$ alkyl, or aryl;

$R^a$ is H, $C_{1-5}$ alkyl substituted with 0-5 $R^e$, $C_{2-5}$ alkenyl substituted with 0-5 $R^e$, $C_{2-3}$ alkynyl substituted with 0-5 $R^e$, $—(CH_2)_n—C_{3-10}$carbocyclyl substituted with 0-5 $R^e$, or $—(CH_2)_n$-heterocyclyl substituted with 0-5 $R^e$; or $R^a$ and $R^a$ together with the nitrogen atom to which they are both attached form a heterocyclyl substituted with 0-5 $R^e$;

$R^b$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $—(CH_2)_n—C_{3-10}$carbocyclyl substituted with 0-5 $R^e$, or $—(CH_2)_n$-heterocyclyl substituted with 0-5 $R^e$;

$R^c$ is $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $C_{3-6}$ carbocyclyl, or heterocyclyl;

$R^d$ is H or $C_{1-4}$ alkyl;

$R^e$ is halo, CN, =O, $C_{1-5}$ alkyl substituted with 0-5 $R^g$, $C_{2-6}$ alkenyl substituted with 0-5 $R^9$, $C_{2-6}$ alkynyl substituted with 0-5 $R^g$, $—(CH_2)_n—C_{3-6}$ cycloalkyl, $—(CH_2)_n$-aryl, $—(CH_2)_n$-heterocyclyl, $—(CH_2)_nOR^f$, or $—C(=O)OR^f$;

$R^f$ is H or $C_{1-3}$ alkyl;

$R^g$ is halo, CN, OH, $C_{1-6}$ alkyl, $C_{3-6}$ cycloalkyl, or aryl;

n is zero, 1, 2, or 3; and p is zero, 1, or 2.

9. A compound of formula (VIII):

(VIII)

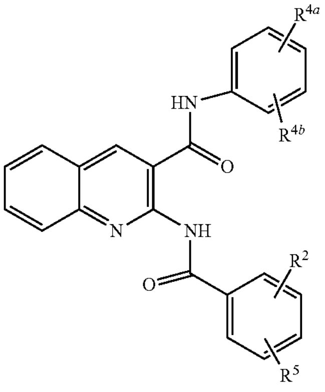

or a pharmaceutically acceptable salt thereof, wherein:

$R^2$ is $—OC_{1-3}$ alkyl;

$R^{4a}$ is halo;

$R^{4b}$ is $C_{1-4}$ alkyl substituted with 0-4 halo;

$R^5$ is $C_6$ aryl substituted with 0-3 $R^6$ and 0-2 $R^7$, or a 3- to 12-membered heterocyclyl comprising 1-4 heteroatoms selected from O, $S(=O)_p$, N and $NR^{10}$ substituted with 0-3 $R^6$ and 0-1 $R^1$;

$R^6$ is halo, =O, —OH, $—OC_{1-4}$ alkyl, or $C_{1-4}$ alkyl substituted with 0-2 halo or OH;

$R^7$ is $C_{1-3}$ alkyl substituted with 0-1 $R^8$ and 0-1 $R^9$, $—OR^b$, $—NR^aR^a$, $—NR^aC(=O)R^b$, $—NR^aC(=O)OR^b$, $—NR^aC(=O)NR^aR^a$, $—NR^aS(=O)_pR^c$, $—C(=O)R^b$, $—C(=O)OR^b$, $—C(=O)NR^aR^a$, $—C(=O)NR^aS(=O)_pR^c$, $—OC(=O)R^b$, $—S(=O)_pR^c$, $—S(=O)_pNR^aR^a$, $C_{3-6}$ cycloalkyl, or a 4- to 6-membered heterocyclyl comprising 1-4 heteroatoms selected from O, $S(=O)_p$, N and $NR^d$, and substituted with 0-5 $R^e$;

$R^8$ is halo, $—C(=O)OR^b$, $—C(=O)NHR^a$, $—C(=O)NHOR^b$, or $C_{1-4}$ alkyl substituted with 0-3 halo or OH;

$R^9$ is $—OR^b$, $—NR^aR^a$, $—NR^aC(=O)R^b$, $—NR^aC(=O)OR^b$, $—NR^aS(=O)_pR^c$, $—NR^aS(O)_pNR^aR^a$, $—OC(=O)NR^aR^a$, $—OC(=O)NR^aOR^b$, $—S(=O)_pNR^aR^a$, or $—S(O)_pR^c$;

$R^{10}$ is H, $C_{1-4}$ alkyl substituted with 0-2 $R^{11}$, $—C(=O)R^b$, $—C(=O)OR^b$, $—C(=O)NR^aR^a$, $C_{3-6}$ cycloalkyl substituted with 0-5 Rr, or a 4- to 6-membered heterocyclyl comprising 1-4 heteroatoms selected from O, $S(=O)_p$, N and $NR^{12}$, and substituted with 0-5 $R^e$;

$R^{11}$ is —OH, —C(=O)OH, or aryl;

$R^{12}$ is H, $C_{1-3}$ alkyl, or aryl;

$R^a$ is H, $C_{1-5}$ alkyl substituted with 0-5 $R^e$, $C_{2-5}$ alkenyl substituted with 0-5 $R^e$, $C_{2-3}$ alkynyl substituted with 0-5 $R^e$, $—(CH_2)_n—C_{3-10}$ carbocyclyl substituted with 0-5 $R^e$, or $—(CH_2)_n$-heterocyclyl substituted with 0-5 $R^e$; or $R^a$ and $R^a$ together with the nitrogen atom to which they are both attached form a heterocyclyl substituted with 0-5 $R^e$:

$R^b$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $—(CH_2)_n—C_{3-10}$ carbocyclyl substituted with 0-5 $R^e$, or $—(CH_2)_n$-heterocyclyl substituted with 0-5 $R^e$;

$R^c$ is $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $C_{3-6}$ carbocyclyl, or heterocyclyl;

$R^d$ is H or $C_{1-4}$ alkyl;

$R^e$ is halo, CN, =O, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, —$(CH_2)$—$C_{3-6}$ cycloalkyl, —$(CH_2)_n$-aryl, —$(CH_2)_n$-heterocyclyl, —$(CH_2)_nOR^f$, or —C(=O)$OR^f$;

$R^f$ is H or $C_{1-3}$ alkyl;

$R^g$ is halo, CN, OH, $C_{1-6}$ alkyl, $C_{3-6}$ cycloalkyl, or aryl;

n is zero, 1, 2, or 3; and p is zero, 1, or 2.

10. A composition comprising a compound of claim 1 or claim 3 or claim 7 or claim 8 or claim 9 or a pharmaceutically acceptable salt thereof, and a pharmaceutically acceptable carrier.

11. A method of treating a disease selected from the group consisting of angina pectoris, unstable angina, myocardial infarction, heart failure, acute coronary disease, cardiac iatrogenic damage, fibrosis, and wherein the treatment is relieving the disease-state comprising administering a therapeutically effective amount of the composition of claim 10 to a patient in need thereof.

12. The method of claim 11 wherein the disease heart failure is acute heart failure or chronic heart failure.

13. The method of claim 12 wherein the disease is heart failure.

14. The method of claim 11 wherein the disease is fibrosis.

* * * * *